(12) United States Patent
Burbank

(10) Patent No.: US 12,114,941 B2
(45) Date of Patent: *Oct. 15, 2024

(54) WRIST ARTICULATION BY LINKED TENSION MEMBERS

(71) Applicant: Intuitive Surgical Operations, Inc., Sunnyvale, CA (US)

(72) Inventor: William A. Burbank, Sandy Hook, CT (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 185 days.

This patent is subject to a terminal disclaimer.

(21) Appl. No.: 17/699,687

(22) Filed: Mar. 21, 2022

(65) Prior Publication Data

US 2022/0280250 A1 Sep. 8, 2022

Related U.S. Application Data

(63) Continuation of application No. 17/069,606, filed on Oct. 13, 2020, now Pat. No. 11,304,768, which is a
(Continued)

(51) Int. Cl.
*A61B 34/30* (2016.01)
*A61B 34/00* (2016.01)
(Continued)

(52) U.S. Cl.
CPC .............. *A61B 34/30* (2016.02); *A61B 34/35* (2016.02); *A61B 34/37* (2016.02); *A61B 34/71* (2016.02);
(Continued)

(58) Field of Classification Search
CPC ......... A61B 34/30; A61B 34/35; A61B 34/37; A61B 34/71; A61B 34/76;
(Continued)

(56) References Cited

U.S. PATENT DOCUMENTS

| 61,581 A | 1/1867 | Taylor et al. |
| 76,819 A | 4/1868 | Ross et al. |

(Continued)

FOREIGN PATENT DOCUMENTS

| CN | 1457747 A | 11/2003 |
| CN | 1534213 A | 10/2004 |

(Continued)

OTHER PUBLICATIONS

Communication Pursuant to Article 94(3) EPC mailed Jul. 12, 2013 for European Application No. 10781556.5 filed Nov. 12, 2010.
(Continued)

*Primary Examiner* — Michael J Lau
(74) *Attorney, Agent, or Firm* — Kilpatrick Townsend & Stockton LLP

(57) ABSTRACT

Methods of articulating and actuating an end effector of a surgical tool include equal rate rotation of an input shaft of the end effector via a drive shaft. A method includes supporting an end effector base of the end effector by an elongate shaft of the surgical tool via a wrist assembly of the surgical tool. Orientation of the end effector base relative to the elongate shaft is controlled via four tension members. An input shaft of a shaft driven mechanism of the end effector is rotated around an input shaft axis by rotating a drive shaft of the surgical tool around a drive shaft axis. A rate of rotation of the drive shaft and a rate of rotation of the input shaft are equal when the end effector base is pivoted relative to the elongate shaft.

11 Claims, 34 Drawing Sheets

Related U.S. Application Data continuation of application No. 16/238,404, filed on Jan. 2, 2019, now Pat. No. 10,835,331, which is a continuation of application No. 14/982,348, filed on Dec. 29, 2015, now Pat. No. 10,206,748, which is a continuation of application No. 12/945,730, filed on Nov. 12, 2010, now Pat. No. 9,259,275.

(60) Provisional application No. 61/260,919, filed on Nov. 13, 2009, provisional application No. 61/260,907, filed on Nov. 13, 2009, provisional application No. 61/260,910, filed on Nov. 13, 2009, provisional application No. 61/260,903, filed on Nov. 13, 2009, provisional application No. 61/260,915, filed on Nov. 13, 2009.

(51) Int. Cl.
*A61B 34/35* (2016.01)
*A61B 34/37* (2016.01)
*A61B 17/29* (2006.01)

(52) U.S. Cl.
CPC ...... *A61B 34/76* (2016.02); *A61B 2017/2927* (2013.01); *A61B 2034/302* (2016.02); *A61B 2034/305* (2016.02); *A61B 2034/715* (2016.02); *Y10T 29/49826* (2015.01)

(58) Field of Classification Search
CPC ...... A61B 2017/2927; A61B 2034/302; A61B 2034/305; A61B 2034/715; Y10T 29/49826
USPC .......................................................... 606/1
See application file for complete search history.

(56) References Cited

U.S. PATENT DOCUMENTS

| | | |
|---|---|---|
| 1,665,241 A | 4/1928 | Weiss |
| 2,067,286 A | 1/1937 | Pearce |
| 2,297,457 A | 9/1942 | Buchhart |
| 2,302,599 A | 11/1942 | Burney |
| 2,687,025 A | 8/1954 | Wildhaber |
| 3,017,755 A | 1/1962 | Miller |
| 3,324,683 A | 6/1967 | Schroter |
| 3,720,954 A | 3/1973 | Czyryk |
| 3,747,368 A | 7/1973 | Morin |
| 3,857,256 A | 12/1974 | Girguis et al. |
| 3,906,747 A | 9/1975 | Orain |
| 3,940,946 A | 3/1976 | Andersen |
| 4,606,695 A | 8/1986 | Lenz |
| 4,642,021 A | 2/1987 | Kikuchi |
| 4,686,866 A | 8/1987 | Rosheim |
| 4,790,225 A | 12/1988 | Moody et al. |
| 4,799,817 A | 1/1989 | Geisthoff |
| 4,892,300 A | 1/1990 | Svyatsky |
| 4,911,033 A | 3/1990 | Rosheim et al. |
| 4,969,533 A | 11/1990 | Holm et al. |
| 5,062,761 A | 11/1991 | Glachet |
| 5,069,569 A | 12/1991 | Lieser |
| 5,101,681 A | 4/1992 | Shpigel |
| 5,314,466 A | 5/1994 | Stern et al. |
| 5,507,773 A | 4/1996 | Huitema et al. |
| 5,710,870 A | 1/1998 | Ohm et al. |
| 5,740,699 A | 4/1998 | Ballantyne et al. |
| 5,792,135 A | 8/1998 | Madhani et al. |
| 5,797,900 A * | 8/1998 | Madhani ................ A61B 34/30 606/1 |
| 5,828,813 A | 10/1998 | Ohm |
| 5,887,778 A | 3/1999 | Maurer et al. |
| 5,954,259 A | 9/1999 | Viola et al. |
| 6,010,054 A | 1/2000 | Johnson et al. |
| 6,394,998 B1 | 5/2002 | Wallace et al. |
| 6,676,684 B1 | 1/2004 | Morley et al. |
| 6,685,698 B2 | 2/2004 | Morley et al. |
| 6,699,235 B2 | 3/2004 | Wallace et al. |
| 6,817,974 B2 | 11/2004 | Cooper et al. |
| 6,860,860 B2 | 3/2005 | Viola |
| 6,969,385 B2 | 11/2005 | Moreyra |
| 7,066,926 B2 | 6/2006 | Wallace et al. |
| 7,086,926 B2 | 8/2006 | Falla |
| 7,121,781 B2 | 10/2006 | Sanchez |
| 7,320,700 B2 | 1/2008 | Cooper et al. |
| 7,464,846 B2 | 12/2008 | Shelton et al. |
| 7,485,127 B2 | 2/2009 | Nistal |
| 7,641,671 B2 | 1/2010 | Crainich |
| 7,708,758 B2 | 5/2010 | Lee et al. |
| 7,918,230 B2 | 4/2011 | Whitman et al. |
| 8,640,788 B2 | 2/2014 | Dachs, II et al. |
| 8,852,174 B2 | 10/2014 | Burbank |
| 8,876,857 B2 | 11/2014 | Burbank |
| 9,101,381 B2 | 8/2015 | Burbank et al. |
| 9,226,761 B2 | 1/2016 | Burbank |
| 9,259,275 B2 | 2/2016 | Burbank |
| 9,763,740 B2 | 9/2017 | Dachs, II et al. |
| 10,045,823 B2 | 8/2018 | Burbank |
| 10,098,635 B2 | 10/2018 | Burbank |
| 10,206,748 B2 | 2/2019 | Burbank |
| 10,292,767 B2 | 5/2019 | Burbank et al. |
| 10,779,896 B2 | 9/2020 | Dachs, II et al. |
| 10,835,331 B2 | 11/2020 | Burbank |
| 10,898,188 B2 | 1/2021 | Burbank |
| 11,083,458 B2 | 8/2021 | Harris et al. |
| 11,090,119 B2 | 8/2021 | Burbank |
| 11,291,447 B2 | 4/2022 | Shelton, IV et al. |
| 11,304,696 B2 | 4/2022 | Shelton, IV et al. |
| 11,304,768 B2 | 4/2022 | Burbank |
| 11,317,917 B2 | 5/2022 | Shelton, IV et al. |
| 11,357,572 B2 | 6/2022 | Burbank et al. |
| 11,452,526 B2 | 9/2022 | Ross et al. |
| 11,523,859 B2 | 12/2022 | Shelton, IV et al. |
| 2001/0021859 A1 | 9/2001 | Kawai et al. |
| 2001/0023311 A1 | 9/2001 | Snow |
| 2002/0120265 A1 | 8/2002 | Fowler |
| 2002/0143346 A1 | 10/2002 | McGuckin, Jr. et al. |
| 2002/0188299 A1 | 12/2002 | Reiley et al. |
| 2003/0105478 A1 | 6/2003 | Whitman et al. |
| 2003/0114851 A1 | 6/2003 | Truckai et al. |
| 2003/0130677 A1 | 7/2003 | Whitman et al. |
| 2003/0158576 A1 | 8/2003 | Nagase et al. |
| 2003/0192391 A1 | 10/2003 | Uematsu et al. |
| 2003/0216667 A1 | 11/2003 | Viola |
| 2004/0011576 A1 | 1/2004 | Taniguchi et al. |
| 2004/0018909 A1 | 1/2004 | Hwa et al. |
| 2004/0193146 A1 | 9/2004 | Lee et al. |
| 2004/0260334 A1 | 12/2004 | Braun |
| 2005/0015356 A1 | 1/2005 | Ireland et al. |
| 2005/0043717 A1 | 2/2005 | Snow |
| 2005/0075664 A1 | 4/2005 | Nagase et al. |
| 2005/0163560 A1 | 7/2005 | Chene et al. |
| 2006/0048787 A1 | 3/2006 | Manzo et al. |
| 2006/0074415 A1 | 4/2006 | Scott et al. |
| 2006/0079884 A1 | 4/2006 | Manzo et al. |
| 2006/0089202 A1 | 4/2006 | Losi, Jr. |
| 2006/0111209 A1 | 5/2006 | Hinman et al. |
| 2006/0111210 A1 | 5/2006 | Hinman |
| 2006/0137888 A1 | 6/2006 | Soika et al. |
| 2006/0199999 A1 | 9/2006 | Ikeda et al. |
| 2007/0021738 A1 | 1/2007 | Hasser et al. |
| 2007/0023477 A1 | 2/2007 | Whitman et al. |
| 2007/0055219 A1 | 3/2007 | Whitman et al. |
| 2007/0221700 A1* | 9/2007 | Ortiz ..................... A61B 34/71 227/175.1 |
| 2007/0233052 A1 | 10/2007 | Brock |
| 2008/0039256 A1 | 2/2008 | Jinno et al. |
| 2008/0058776 A1 | 3/2008 | Jo et al. |
| 2008/0177283 A1 | 7/2008 | Lee et al. |
| 2008/0257935 A1 | 10/2008 | Viola et al. |
| 2008/0271906 A1 | 11/2008 | Walker |
| 2008/0312668 A1 | 12/2008 | Grace |
| 2009/0047061 A1 | 2/2009 | Chene et al. |
| 2009/0065549 A1 | 3/2009 | Viola |
| 2009/0090764 A1 | 4/2009 | Viola et al. |

(56) References Cited

U.S. PATENT DOCUMENTS

| | | |
|---|---|---|
| 2009/0112229 A1 | 4/2009 | Omori et al. |
| 2009/0173178 A1 | 7/2009 | Okazaki |
| 2009/0183887 A1 | 7/2009 | Baber et al. |
| 2009/0192519 A1 | 7/2009 | Omori |
| 2009/0198253 A1 | 8/2009 | Omori |
| 2009/0264931 A1 | 10/2009 | Miller et al. |
| 2010/0011900 A1 | 1/2010 | Burbank et al. |
| 2010/0011901 A1 | 1/2010 | Burbank |
| 2010/0016852 A1 | 1/2010 | Manzo et al. |
| 2010/0016853 A1 | 1/2010 | Burbank |
| 2011/0118708 A1 | 5/2011 | Burbank et al. |
| 2011/0152879 A1 | 6/2011 | Williams |
| 2019/0099231 A1 | 4/2019 | Bruehwiler et al. |
| 2019/0298453 A1 | 10/2019 | Burbank et al. |
| 2020/0382921 A1 | 12/2020 | Dachs, II et al. |
| 2021/0022813 A1 | 1/2021 | Burbank |
| 2021/0106330 A1 | 4/2021 | Burbank |
| 2021/0338332 A1 | 11/2021 | Burbank |

FOREIGN PATENT DOCUMENTS

| | | |
|---|---|---|
| CN | 101365391 A | 2/2009 |
| CN | 101495046 A | 7/2009 |
| EP | 0710089 B1 | 12/2001 |
| EP | 1782927 A2 | 5/2007 |
| EP | 1813200 A2 | 8/2007 |
| EP | 2036505 B1 | 11/2010 |
| EP | 2263568 A2 | 12/2010 |
| EP | 1585425 B1 | 8/2016 |
| FR | 38899 E | 8/1931 |
| FR | 1012165 A | 7/1952 |
| GB | 195353 A | 3/1924 |
| GB | 802506 A | 10/1958 |
| GB | 2294526 A | 5/1996 |
| JP | 58217823 A | 12/1983 |
| JP | H03501233 A | 3/1991 |
| JP | H07163574 A | 6/1995 |
| JP | 2000023996 A | 1/2000 |
| JP | 2001276091 A | 10/2001 |
| JP | 2002306496 A | 10/2002 |
| JP | 2005505309 A | 2/2005 |
| JP | 2006075376 A | 3/2006 |
| JP | 2007038003 A | 2/2007 |
| JP | 2007130471 A | 5/2007 |
| JP | 2007524451 A | 8/2007 |
| JP | 2008036219 A | 2/2008 |
| JP | 2009502352 A | 1/2009 |
| JP | 2009066400 A | 4/2009 |
| JP | 2009112538 A | 5/2009 |
| JP | 2009165504 A | 7/2009 |
| JP | 2009178230 A | 8/2009 |
| JP | 2009178506 A | 8/2009 |
| JP | 2010540041 A | 12/2010 |
| WO | WO-8902544 A1 | 3/1989 |
| WO | WO-9743942 A1 | 11/1997 |
| WO | WO-9743943 A1 | 11/1997 |
| WO | WO-03001987 A2 | 1/2003 |
| WO | WO-2006073581 A2 | 7/2006 |
| WO | WO-2006075153 A1 | 7/2006 |
| WO | WO-2007120353 A2 | 10/2007 |
| WO | WO-2007146987 A2 | 12/2007 |
| WO | WO-2009039506 A1 | 3/2009 |
| WO | WO-2009126955 A2 | 10/2009 |
| WO | WO-2011060315 A2 | 5/2011 |

OTHER PUBLICATIONS

Communication Pursuant to Article 94(3) EPC mailed Dec. 20, 2013 for European Application No. 10779428.1 filed Nov. 12, 2010.
Extended European Search Report for Application No. EP19203804 mailed on Feb. 3, 2020, 7 pages.
Extended European Search Report for Application No. 12162263.3, mailed on Oct. 26, 2016, 7 pages.
Extended European Search Report for Application No. 12162273.2, mailed on Oct. 26, 2016, 7 pages.
Extended European Search Report for Application No. 13151922.5, mailed on Oct. 26, 2016, 7 pages.
Extended European Search Report for Application No. 18171951.9, mailed on Aug. 7, 2018, 7 pages.
Extended European Search Report for Application No. 18198026.9, mailed on Dec. 3, 2018, 8 pages.
Extended European Search Report for Application No. EP18170942.9, mailed on Aug. 6, 2018, 9 pages.
Extended European Search Report for Application No. EP19206336 mailed on Feb. 11, 2020, 9 pages.
Extended European Search Report for Application No. EP20187989.7 mailed on Dec. 4, 2020, 08 pages.
Office Action mailed Jul. 2, 2014 for Chinese Application No. 201080051475.3 filed Nov. 12, 2010.
Office Action mailed May 2, 2014 for Japanese Application No. 2012539033 filed Nov. 12, 2010.
Office Action mailed May 8, 2014 for Japanese Application No. 2012539037 filed Nov. 12, 2010.
Office Action mailed Aug. 13, 2014 for Japanese Application No. 2012539035 filed Nov. 13, 2009.
Office Action mailed Jun. 17, 2015 for Japanese Application No. 2013200054 filed Sep. 26, 2013, 10 pages.
Office Action mailed Aug. 26, 2014 for Japanese Application No. 2013200054 filed Sep. 26, 2013.
Office Action mailed Aug. 29, 2014 for Japanese Application No. 2013200053 filed Sep. 26, 2013.
Office Action mailed May 6, 2014 for Chinese Application No. 201080051059.3 filed Nov. 12, 2010.
PCT/US10/56601 International Search Report and Written Opinion of the International Searching Authority, mailed Jul. 6, 2011, 18 pages.
PCT/US10/56607 Invitation to Pay Additional Fees and Results of the Partial International Search, mailed Mar. 21, 2011, 5 pages.
PCT/US10/56610 International Search Report and Written Opinion of the International Searching Authority, mailed Feb. 18, 2011, 16 pages.
PCT/US2010/056607 International Search Report and Written Opinion of the International Searching Authority, mailed Jun. 15, 2011, 20 pages.
Rosheim, Mark E., Chapter 5: "Pitch-Yaw-Roll Wrists," Robot Wrist Actuators, Wiley & Sons, New York, 1989, pp. 95-206.
Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.
Extended European Search Report for Application No. EP22170371.3, mailed on Jul. 29, 2022, 09 pages.

* cited by examiner

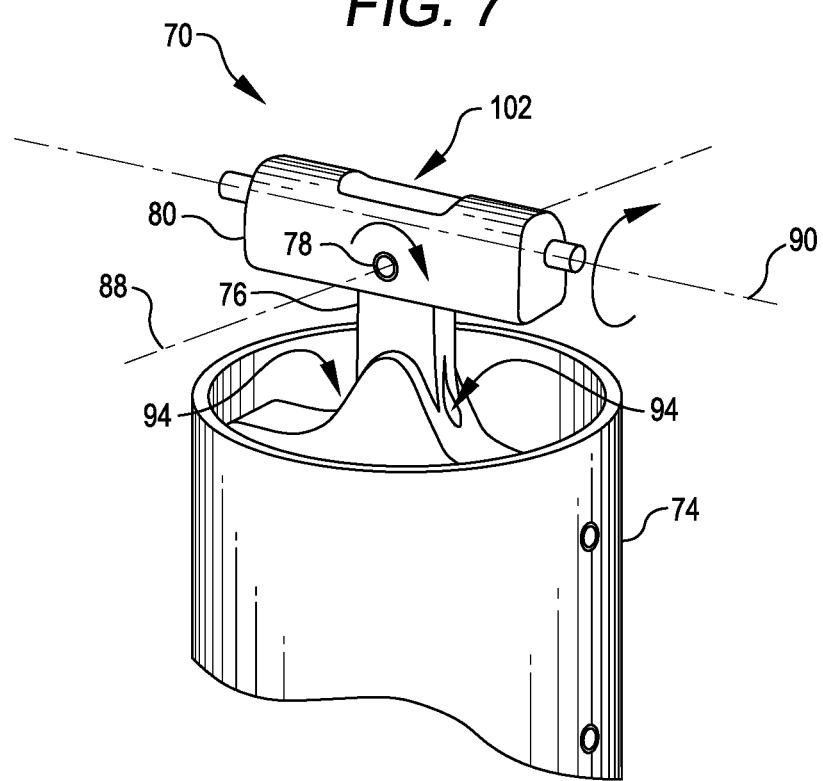

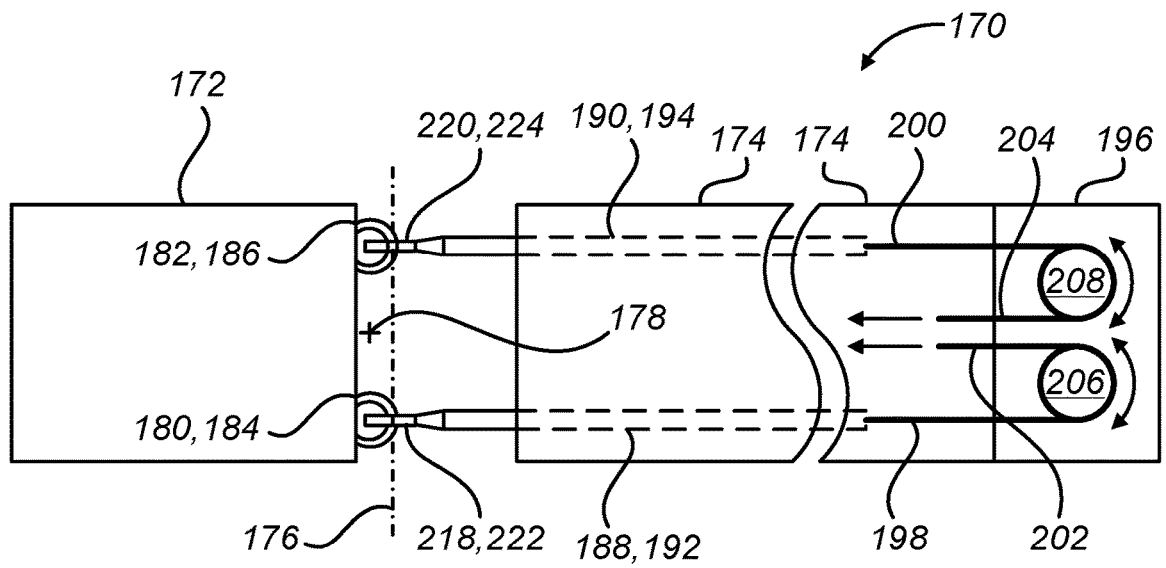
FIG. 13a
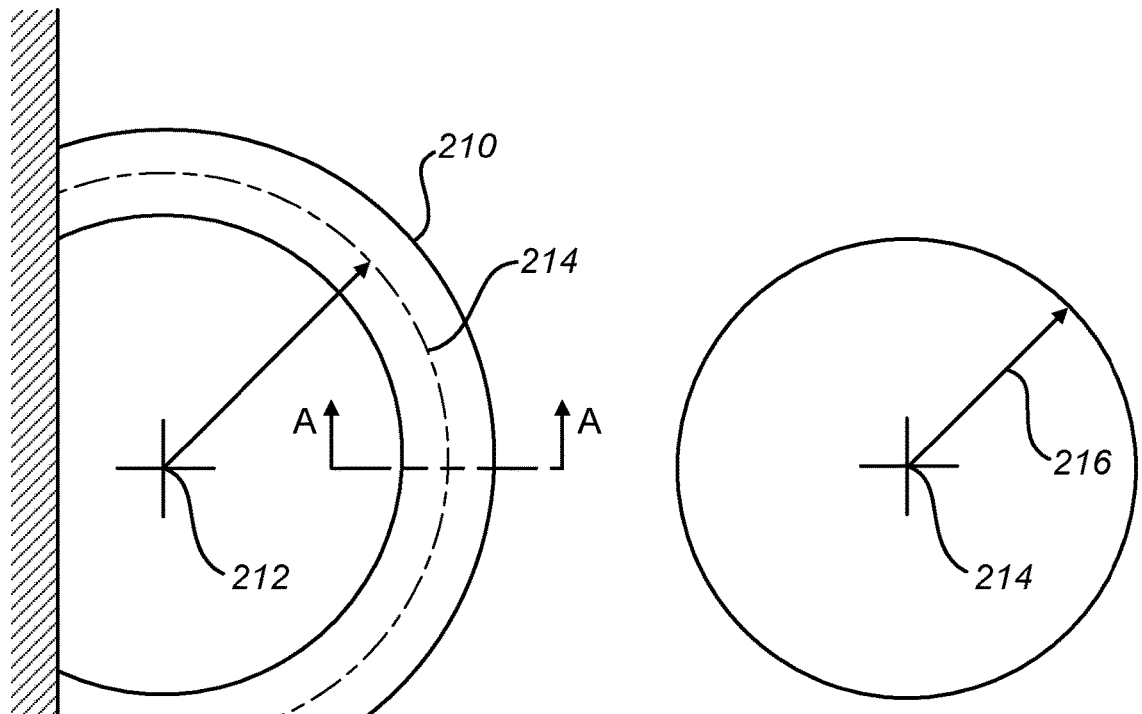
FIG. 13b
FIG. 13c 30 deg. Yaw

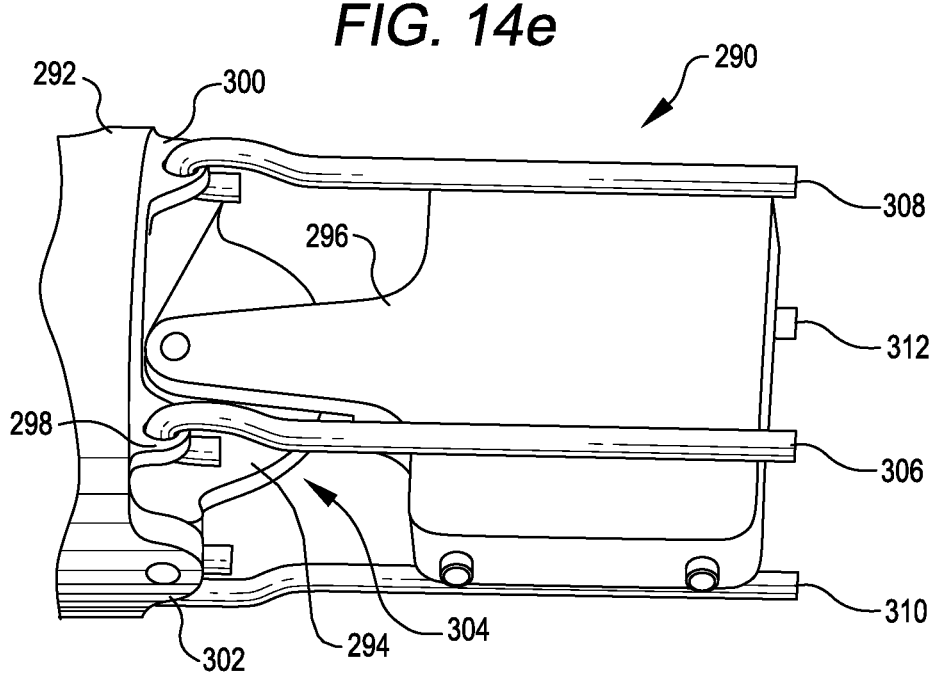

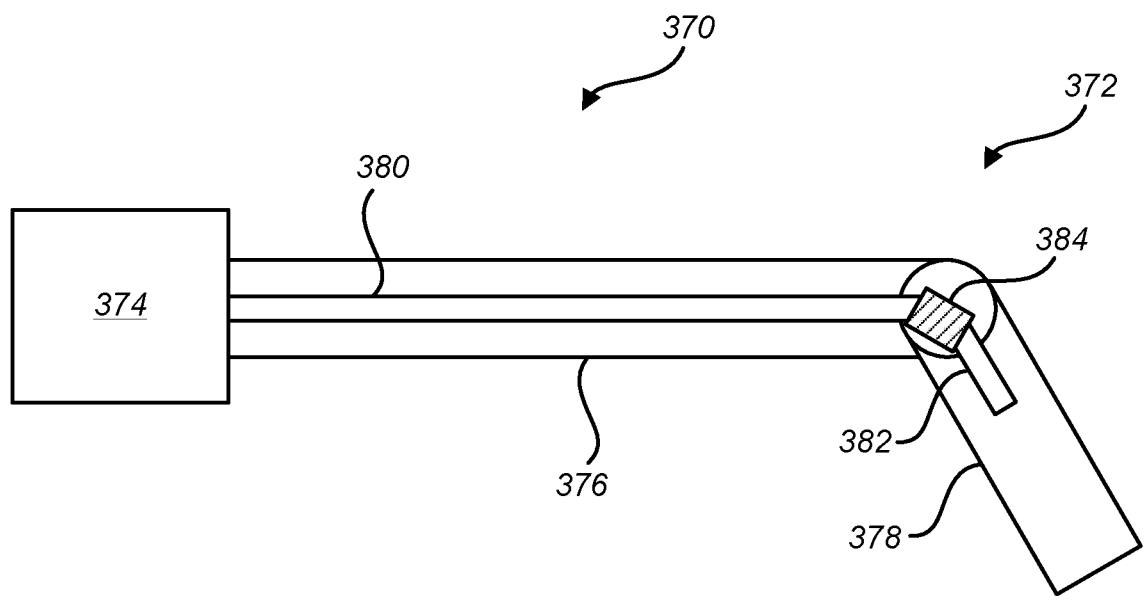
FIG. 17
FIG. 18
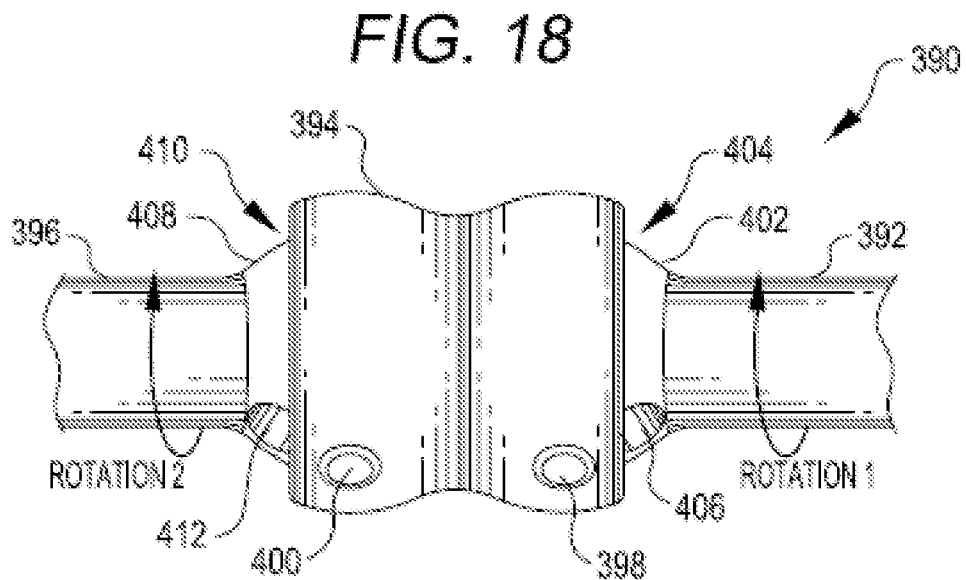

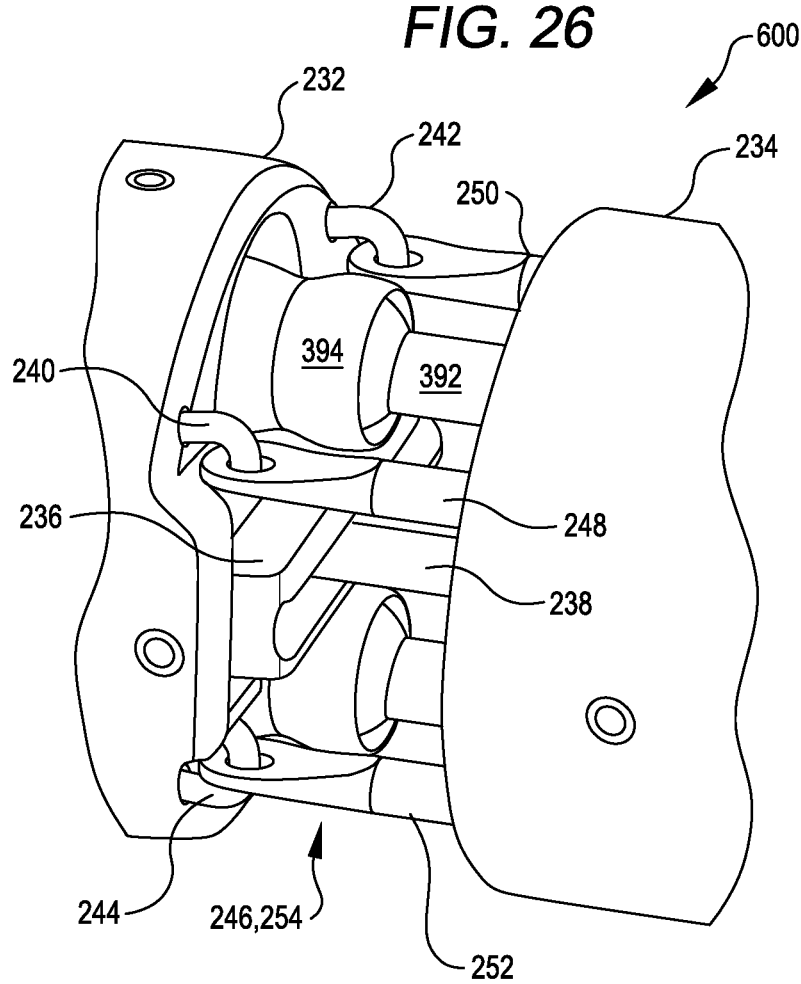

WRIST ARTICULATION BY LINKED TENSION MEMBERS

CROSS-REFERENCES TO RELATED APPLICATIONS

The present application is a Continuation of U.S. patent application Ser. No. 17/069,606 filed Oct. 13, 2020 (now U.S. Pat. No. 11,304,768); which is a Continuation of U.S. patent application Ser. No. 16/238,404 filed Jan. 2, 2019 (now U.S. Pat. No. 10,835,331); which is a Continuation of U.S. Patent Appln Ser. No. 14/982,348 filed Dec. 29, 2015 (now U.S. Pat. No. 10,206,748); which is a Continuation of U.S. Patent Application Ser. No. 12/945,730 filed Nov. 12, 2010 (now U.S. Pat. No. 9,259,275); which claims the benefit of U.S. Provisional Appln Nos. 61/260,903, 61/260,910, 61/260,915, 61/260,907, and 61/260,919, all of which were filed Nov. 13, 2009; the full disclosures which are incorporated herein by reference in their entirety for all purposes.

BACKGROUND

Minimally invasive surgical techniques are aimed at reducing the amount of extraneous tissue that is damaged during diagnostic or surgical procedures, thereby reducing patient recovery time, discomfort, and deleterious side effects. As a consequence, the average length of a hospital stay for standard surgery may be shortened significantly using minimally invasive surgical techniques. Also, patient recovery times, patient discomfort, surgical side effects, and time away from work may also be reduced with minimally invasive surgery.

A common form of minimally invasive surgery is endoscopy, and a common form of endoscopy is laparoscopy, which is minimally invasive inspection and/or surgery inside the abdominal cavity. In standard laparoscopic surgery, a patient's abdomen is insufflated with gas, and cannula sleeves are passed through small (approximately one-half inch or less) incisions to provide entry ports for laparoscopic instruments.

Laparoscopic surgical instruments generally include an endoscope (e.g., laparoscope) for viewing the surgical field and tools for working at the surgical site. The working tools are typically similar to those used in conventional (open) surgery, except that the working end or end effector of each tool is separated from its handle by an extension tube (also known as, e.g., an instrument shaft or a main shaft). The end effector can include, for example, a clamp, grasper, scissor, stapler, cautery tool, linear cutter, or needle holder.

To perform surgical procedures, the surgeon passes working tools through cannula sleeves to an internal surgical site and manipulates them from outside the abdomen. The surgeon views the procedure from a monitor that displays an image of the surgical site taken from the endoscope. Similar endoscopic techniques are employed in, for example, arthroscopy, retroperitoneoscopy, pelviscopy, nephroscopy, cystoscopy, cisternoscopy, sinoscopy, hysteroscopy, urethroscopy, and the like.

Minimally invasive telesurgical robotic systems are being developed to increase a surgeon's dexterity when working on an internal surgical site, as well as to allow a surgeon to operate on a patient from a remote location (outside the sterile field). In a telesurgery system, the surgeon is often provided with an image of the surgical site at a control console. While viewing a three dimensional image of the surgical site on a suitable viewer or display, the surgeon performs the surgical procedures on the patient by manipulating master input or control devices of the control console. Each of the master input devices controls the motion of a servo-mechanically actuated/articulated surgical instrument. During the surgical procedure, the telesurgical system can provide mechanical actuation and control of a variety of surgical instruments or tools. Many of the telesurgical tools have jaws or other articulatable end effectors that perform various functions for the surgeon, for example, holding or driving a needle, grasping a blood vessel, dissecting tissue, or the like, in response to manipulation of the master input devices. Tools having distal wrist joints allow the surgeon to orient the tool within the internal surgical site, greatly enhancing the freedom with which the surgeon can interact with (and treat) the tissue in real time.

Telesurgical systems are finding increasing applications by surgeons for growing variety of therapies. New tools would help to continue this growth, and particularly tools such as staplers, linear cutters, and the like (which are capable of imposing significant clamping and other forces against the internal tissues). Unfortunately, it can be challenging to transmit the desired telesurgical end effector forces through known tool wrists, particularly while retaining the response time, precision, flexibility, and reliability in the tool that is desired for telesurgical tasks.

For example, non-robotic surgical tools comprising linear clamping, cutting, and stapling devices have been employed in many different surgical procedures. Such a tool can be used to resect a cancerous or anomalous tissue from a gastro-intestinal tract. Unfortunately, many known surgical tools, including known linear clamping, cutting, and stapling tools, lack the ability to transmit desired torques (e.g., tissue clamping torque) or forces (e.g., staple firing force) across a compact articulated wrist, which may reduce the effectiveness of the surgical tool. Alternative tools with a shaft driven clamping mechanism also fail to provide rotational movement of an end effector to mimic the natural action of a surgeon's wrist.

For the reasons given above, it is desirable to provide improved surgical and/or robotic wrist structures. It would also be desirable to provide improved minimally invasive surgical tools that include a wrist mechanism that mimics the natural action of a surgeon's wrist, while allowing enhanced end effector forces and a response time suitable for telesurgical control.

BRIEF SUMMARY

Surgical tools with a two degree-of-freedom wrist, and related methods, are provided. The disclosed surgical tools may be particularly beneficial when used in minimally invasive surgery. In many embodiments, an intermediate wrist member is pivotally coupled with a distal end of an instrument shaft so as to rotate about a first axis transverse to the shaft, and an end effector body is pivotally coupled to the intermediate member so as to rotate about a second axis transverse to the first axis. Such a two degree-of-freedom wrist can be used to articulate the end effector body in a way that mimics the natural action of a surgeon's wrist, thereby providing a desirable amount of maneuverability for the end effector body. In many embodiments, the intermediate member has an elongate shape. An elongate shape leaves adjacent areas free for the routing of actuation components, for example, actuation components that articulate the end effector body relative to the instrument shaft, and actuation components (e.g., control cables, drive shafts) that articulate one or more end effector features relative to the end effector body. In many embodiments, the two degree-of-freedom wrist includes internal passages for guiding control cables. Such internal passages can be configured to inhibit altering control cable tensions during pivoting about the first and second axes.

Exemplary embodiments provide wrist articulation via linked tension members. In many embodiments, an end effector is coupled with a distal end of an elongate shaft via a two degree-of-freedom joint so as to allow the end effector to be oriented within an internal surgical space. In the exemplary embodiments, opposed movements of tension members angularly orient the end effector relative to the shaft, and sliding interface surfaces between the tension members and the end effector vary positions of the tension members in correlation with the orientation of the end effector to inhibit undesirable changes in tension of the tension members. By inhibiting such changes in tension of the tension members, detrimental control cable slack and/or overstressing of surgical tool components may be avoided when the tension members are used as linked pairs, for example, with opposed tension members sharing a common linear drive mechanism (e.g., a motor driven capstan). Actuating the tension members in linked pairs may provide for smooth and responsive articulation of the end effector relative to the shaft. Wrist articulation by linked tension members can also be used to reduce the length of the surgical tool distal of the shaft, which may improve access in a confined body space, angle of access to body structures, and visibility of body structures.

Mechanisms for transmitting torque through an angle, minimally invasive surgical tools comprising a mechanism for transmitting torque through an angle, and related methods are also provided. The disclosed mechanisms can be used, for example, to transmit torque to a shaft driven actuation mechanism of a surgical end effector that is mounted to an instrument shaft via a two degree-of-freedom wrist. In many surgical applications (e.g., many minimally invasive surgical applications) it may be beneficial to use a surgical tool comprising a surgical end effector mounted to the distal end of an instrument shaft via a two degree-of-freedom wrist so as to mimic the (often relatively rapid) natural action of a surgeon's wrist. By actuating the end effector with a rotational shaft drive, a high level of force can be applied to tissues through a narrow shaft. For example, such a shaft driven mechanism can be used to articulate a clamping jaw of the end effector so as to generate a high clamping force. Exemplary embodiments can transmit sufficient torque through the angled wrist of a minimally invasive surgical tool using a relatively simple dual ball-and-socket joint system in which the ball ends are coupled together to constrain the socket angle, and in which pins traversing the sockets transfer torque. This simple arrangement lends itself to miniaturization for use in, for example, a surgical instrument. This simple arrangement may also improve the reliability of tools that transmit torque through angles exceeding 60 degrees, thereby allowing substantial reorientation of an end effector relative to an instrument shaft. In many embodiments, a rate of rotation of a drive shaft and a driven shaft are substantially equal even when the drive shaft and the driven shaft are non-parallel, which may help provide smooth transmission of torque through the angle.

In a first aspect, a minimally invasive surgical tool is provided. The surgical tool includes a tubular instrument shaft having a proximal end and a distal end with a bore there between, an end effector including an end effector body; an intermediate wrist member pivotally coupled with the distal end of the shaft and pivotally coupled with the end effector body; and an actuation system extending distally through the bore of the shaft so as to orient the end effector body and actuate the end effector. The instrument shaft has an instrument-shaft axis. Pivoting of the intermediate body relative to the shaft orients intermediate member about a first axis relative to the shaft. Pivoting of the end effector body relative to the intermediate member orients the end effector body about a second axis relative to the intermediate member. The first axis is transverse to the shaft axis. The second axis is transverse to the first axis. The intermediate member has an exterior width along the first axis and an exterior length along the second axis. The length is significantly different than the width so that the intermediate member has an elongate cross section. A portion of the actuation system is laterally separated from the elongate cross section of the intermediate member between the shaft and the end effector body.

The intermediate member can include one or more additional features and/or characteristics. For example, the width of the intermediate member can be less than one-fourth the length of the intermediate member. The first axis and the second axis can be within 2 mm of being coplanar. The first axis and the second axis can be coplanar. The intermediate member can include internal passages for guiding control cables of the actuation system between the instrument shaft and the end effector body.

The surgical tool can include one or more additional features and/or characteristics. For example, the surgical tool can include a first joint pivotally coupling the shaft to the intermediate member and a second joint pivotally coupling the intermediate member to the end effector body. The first joint can include a single pivot shaft extending along the first axis within the width of the intermediate member so that the first joint is disposed within a central region between the shaft and the end effector body clear of the laterally separated portion of the actuation system. The second joint can include first and second coaxial pivot shafts separated along the second axis. The intermediate member can include internal passages for guiding control cables of the actuation system between the instrument shaft and the end effector body and between the coaxial pivot shafts of the second joint. The surgical tool can include a support member fixedly coupled with the instrument shaft and pivotally coupled with the intermediate member for rotation about the first axis. The support member can include internal passages for guiding control cables of the actuation system routed between a bore of the instrument shaft and the end effector body. The guide surfaces can constrain the control cables so as to inhibit altering cable tensions during pivoting about the first and second axes.

The actuation system can include one or more additional features and/or characteristics. For example, the laterally separated portion of the actuation system can include a first rotatable drive shaft for driving a first actuation mechanism of the end effector. The first drive shaft can be routed between the end effector body and the bore so as to pass adjacent to a first side of the intermediate member. The laterally separated portion of the actuation system can include a second rotatable drive shaft for driving a second actuation mechanism of the end effector. The second drive shaft can be routed between the end effector body and the bore so as to pass adjacent to a second side of the intermediate member, the second side being opposite the first side. An orientation portion of the actuation system can be operable to vary the orientation of the end effector body relative to the instrument shaft about the first and second axes. The orientation portion can be back drivable so that forces applied to the end effector body so as to alter its orientation are transmitted proximally through the bore by the actuation system. An actuation of the end effector can include articulation of a joint of the end effector.

In another aspect, a method for manufacturing a minimally invasive surgical tool is provided. The method includes pivotally coupling an intermediate member to an instrument shaft for rotation about a first axis oriented non-parallel to an elongate direction of the instrument shaft, pivotally coupling an end effector to the intermediate member for rotation about a second axis oriented non-parallel to the first axis and the elongate direction, and coupling an actuation mechanism with the end effector. The actuation mechanism is operable to vary the orientation of the end effector relative to the elongate direction in two dimensions. At least a portion of the actuation mechanism is routed between the end effector and a bore of the instrument shaft so as to pass outside of and separated from at least one side of the intermediate member.

In the method for manufacturing a minimally invasive surgical tool, the intermediate member coupled to the instrument shaft, and to which the end effector is coupled, can include one or more additional features and/or characteristics. For example, the first axis can be normal to the second axis. At least one of the first axis or the second axis can be normal to the instrument-shaft elongate direction. The intermediate member can have an exterior width in the first-axis direction and a maximum exterior length in the second-axis direction that is greater than the width in the first-axis direction. The intermediate member can have a maximum exterior width in the first-axis direction that is less than one-third of the exterior length. In intermediate member can include internal passages for guiding control cables routed between the end effector and a bore of the instrument shaft. The guide surfaces can constrain the control cables so as to inhibit altering cable tensions during pivoting about the first and second axes.

The method can include further steps. For example, the method can further include routing end effector control cables through intermediate-member internal passages. The method can further include back driving the actuation mechanism by varying the orientation of the end effector relative to the instrument shaft so that forces applied to the end effector so as to alter its orientation are transmitted proximally through the bore by the actuation system. Actuation of the end effector can include articulating a joint of the end effector.

In another aspect, a minimally invasive surgical method is provided. The method includes inserting a surgical end effector of a tool to an internal surgical site via a minimally invasive aperture or natural orifice, pivoting an intermediate member of the tool relative to a shaft of the tool about a first joint so as to orient the intermediate member about a first axis relative to the shaft of the tool supporting the end effector, pivoting the end effector relative to the intermediate member about a second joint so as to orient the end effector about a second axis relative to the intermediate member, mechanically actuating the end effector with an actuation-system component that passes between the bore and the end effector laterally offset from a central joint. One of the first joint and the second joint includes the central joint, which is a centrally located joint disposed within a central portion of a cross section of the tool. In the method, an actuation of the end effector can include articulating a joint of the end effector.

In another aspect, a minimally invasive surgical tool is provided. The surgical tool includes an elongate first link, a second link, four attachment features disposed on the second link, and four tension members. The elongate first link has a distal end, a proximal end, and a first link axis defined there between. The first link has an axial bore. The second link is pivotally coupled with the distal end of the first link so as to orient the second link about a first axis and a second axis. The first and second axes are nonparallel to the first link axis. The first axis is nonparallel to the second axis. The four tension members extend distally from within the bore of the first link to the attachment features so that opposed axial movement of the tension members angularly orients the second link relative to the first link about the first and second axes. Interface surfaces between the tension members and the attachment features vary the positions of the tension members relative to the second link in correlation with angular orientations of the second link relative to the first link so as to inhibit changes in tension of the tension members.

The first and second axes can have one or more additional characteristics. For example, the first and second axes can be non-intersecting. The first and second axes can be separated by various distances, for example, by 2 mm or less. The first axis can be transverse to the first link axis and the second axis can be transverse to the first axis.

Each of the tension members can interact with a corresponding attachment feature so as to selectively constrain the motion of the tension member. For example, each of the tension members can pivot about a first associated center relative to one of the attachment features when the second link pivots about the first axis. Each of the tension members can pivot about a second associated center relative to one of the attachment features when the second link pivots about the second axis. The tension members can slidingly engage the attachment features. The interface surfaces can include curving cylindrical surfaces having circular cross-sections and curving interface axes, the circular cross-sections defining cross-sectional centers and the curving interface axes defining centers of curvature. Each of the first and second associated centers can correspond to a cross-sectional center or a center of curvature.

The attachment features can comprise a curved portion. For example, each of the attachment features can comprise a curved portion. Each of the tension members can comprise an attachment lug configured to slidingly receive one of the curved portions so as to slide against and along the curved portion when the second link pivots about one of the first and second axes. Each of the curved portions can comprise a centerline that lies in a plane perpendicular to the first axis or the second axis. Each of the curved portions can have a first radius of curvature about its curved centerline and a fixed center of curvature for its curved centerline. Each of the fixed centers of curvature can lie in a plane containing at least one of the first axis or the second axis. Each of the curved portion centerlines can be tangent to a plane containing at least one of the first axis or the second axis.

The attachment features can comprise an attachment lug. For example, each of the attachment features can comprise an attachment lug. Each of the tension members can comprise a curved portion configured to be slidingly received by one of the attachment lugs so that the curved portion slides within the attachment lug when the second link pivots about one of the first and second axes. Each of the attachment lugs can have a connection hole axis oriented parallel to the first axis or the second axis. Each connection hole axis can lie in a plane containing at least one of the first axis or the second axis. Each of the curved portions can comprise a curved centerline that lies in a plane perpendicular to the first axis or the second axis. Each of the curved portions can have a first radius of curvature about its curved centerline and a fixed center of curvature for its curved centerline. Each of the fixed centers of curvature can lie in a plane containing at least one of the first axis or the second axis. Each of the curved portion centerlines can be tangent to a plane containing at least one of the first axis or the second axis.

Diagonally opposed tension members can be paired together and actuated in common. For example, each of the attachment features can be offset from the first and second axes when viewed along the first link axis, with one of the attachment features being disposed in each quadrant defined by the first and second axes when viewed along the first link axis. A first diagonally opposed pair of the tension members can be actuated by at least one cable extending from a first tension member of the first diagonally opposed pair to a second tension member of the first diagonally opposed pair, with the at least one cable being wrapped around a first capstan. Varying positions of the first diagonally opposed pair of the tension members relative to the second link can inhibit variations in tension of the at least one cable which would be imposed if the tension members were coupled to the attachment features with spherical center joints. A second diagonally opposed pair of the tension members can be actuated by at least one cable extending from a first tension member of the second diagonally opposed pair to a second tension member of the second diagonally opposed pair, with the at least one cable being wrapped around a second capstan. Varying positions of the second diagonally opposed pair of the tension members relative to the second link can inhibit variations in tension of the at least one cable which would be imposed if the tension members were coupled to the attachment features with spherical center joints. The first diagonally opposed pair of the tension members is different from the second diagonally opposed pair of the tension members, and the second capstan is different from the first capstan.

In another aspect, a surgical tool is provided. The surgical tool comprises an elongate first link, a plurality of control cables, a second link, and a plurality of interface assemblies. The elongate first link has a distal end, a proximal end, and a first link axis defined there between. The first link has an axial bore. The plurality of control cables extends distally within the bore of the first link from a control cable actuation assembly disposed adjacent the proximal end of the first link. The second link is pivotally coupled with the distal end of the first link so as to orient the second link about a first axis and a second axis. The first and second axes are nonparallel to the first link axis. The first axis is nonparallel to the second axis. Each interface assembly couples one of the control cables with the second link so that axial movement of the control cables angularly orients the second link relative to the first link about the first and second axes. One of the interface assemblies comprises a length of curved portion and an attachment lug having an attachment lug hole sized to slidingly receive the curved portion. The attachment lug rotates about the curved portion when the second link rotates about the first axis and slides against and along the curved portion when the second link rotates about the second axis.

In many embodiments, the plurality of control cables comprises four control cables. Each of the interface assemblies can comprise a length of curved portion and an attachment lug having an attachment lug hole sized to slidingly receive the curved portion such that the attachment lug rotates about the curved portion when the second link rotates about the first axis and slides against and along the curved portion when the second link rotates about the second axis.

In another aspect, a method for manufacturing a surgical tool is provided. The method comprises pivotally coupling a second link to a first link to rotate about a first axis oriented non-parallel to an elongate direction of the first link and to rotate about a second axis oriented non-parallel to both the elongate direction of the first link and the first axis, coupling a tension member with each of four attachment features disposed on the second link, and coupling each of the tension members with an actuation mechanism operable to control the angular orientation of the second link relative to the first link in two dimensions by actuating the tension members. Each of the attachment features is offset from the first and second axes when viewed along the elongate direction of the first link. One of the attachment features is disposed in each quadrant defined by the first and second axes when viewed along the elongate direction of the first link. Each of the tension members extends distally from within the bore of the first link to one of the attachment features of the second link so that axial movement of the tension members angularly orients the second link relative to the first link about the axes. Interface surfaces between the tension members and the attachment features vary a position of the tension members relative to the second link in correlation with the angular orientation of the second link relative to the first link so as to inhibit changes in tension of the tension members.

Coupling each of the tension members with an actuation mechanism can comprise additional steps, for example, coupling a first tension member of the tension members with a first control cable. A second tension member of the tension members can be coupled with a second control cable, where the second tension member is diagonally opposite to the first tension member. The first and second control cables can be coupled with a first capstan of the actuation mechanism. A third tension member of the tension members can be coupled with a third control cable. A fourth tension member of the tension members can be coupled with a fourth control cable, where the fourth tension member is diagonally opposite to the third tension member. The third and fourth control cables can be coupled with a second capstan of the actuation mechanism.

In another aspect, a surgical instrument is provided. The surgical instrument comprises a first link, a second link comprising an attachment feature, a joint that couples the first and second links, and a tension member comprising an attachment lug. The attachment feature comprises a curved portion. The joint rotates around a first axis defined in a first plane and around a second axis defined in a second plane. The first and second planes are parallel to and offset from one another. The attachment lug is coupled to the attachment feature. The attachment lug rotates around the curved portion when the tension member rotates the joint around the first axis. The attachment lug slides against and along the curved portion when the actuation member rotates the joint around the second axis.

In another aspect, a mechanism for transmitting torque through an angle is provided. The mechanism includes a coupling member comprising a first end and a second end with a coupling axis defined there between, a coupling pin, a drive shaft having a drive axis and a distal end, and a driven shaft having a proximal end and a driven axis. The first end of the coupling member comprises a receptacle. The coupling pin extends across the receptacle. The drive shaft distal end is received within the receptacle. The drive shaft distal end comprises a slot receiving the coupling pin throughout a range of angles between the coupling axis and the drive axis so that rotation of the drive shaft produces rotation of the coupling member via the coupling pin. The proximal end of the driven shaft coupled with the second end of the coupling member so that rotation of the coupling member about the coupling axis produces rotation of the driven shaft about the driven axis. The drive shaft is coupled with the driven shaft so as to maintain corresponding angles between the drive axis and the coupling axis, and the driven axis and the coupling axis when an angle between the drive axis and the driven axis varies during rotation of the shafts.

A mechanism for transmitting torque through an angle can include one or more additional features and/or can have one or more additional characteristics. For example, the mechanism can further comprise a cross pin to couple the drive shaft with the coupling pin. The cross pin can be oriented transverse to the coupling pin and mounted for rotation relative to the drive shaft. An outer surface of the drive shaft distal end can comprise a spherical surface. The outer surface of the drive shaft can interface with the receptacle of the coupling member so as to axially constrain the drive shaft and receptacle relative to each other during spherical pivoting there between. The receptacle can comprise a spherical surface that interfaces with the drive shaft spherical surface. The drive shaft distal end can comprise a set of spherical gear teeth and the driven shaft proximal end can comprise a set of spherical gear teeth interfacing with the drive shaft gear teeth so as to maintain substantially equivalent angles between the drive axis and the coupling axis, and the driven axis and the coupling axis. In many embodiments, at least one of the drive shaft and the drive shaft gear teeth or the driven shaft and the driven shaft gear teeth are integrally formed. In many embodiments, the mechanism is operable to transmit torque through an angle exceeding 60 degrees.

In another aspect, a mechanism for transmitting torque through an angle is provided. The mechanism includes a drive shaft having a distal end and a drive axis, a driven shaft having a proximal end and a driven axis, and a coupling member coupled with each of the drive shaft distal end and the driven shaft proximal end so that rotation of the drive shaft about the drive axis produces rotation of the driven shaft about the driven axis. At least one of the drive shaft distal end or the driven shaft proximal end comprises a protrusion. The coupling member comprises a tubular structure defining a drive receptacle and a driven receptacle with a coupling axis defined there between. At least one of the drive receptacle or the driven receptacle comprises a slot configured to receive the at least one protrusion and accommodate the at least one protrusion through a range of angles between the drive shaft and the driven shaft. The protrusion interacts with the slot so as to transfer rotational motion between the drive shaft and the driven shaft. The drive shaft distal end engages the driven shaft proximal end so as to maintain corresponding angles between the drive axis and the coupling axis, and the driven axis and the coupling axis when an angle between the drive axis and the driven axis varies during rotation of the shafts. In many embodiments, the mechanism is operable to transmit torque through an angle exceeding 60 degrees.

In many embodiments, the drive shaft and the driven shaft interface with the coupling member so that the drive shaft and the driven shaft are constrained relative to the coupling member. For example, each of the drive shaft distal end and the driven shaft proximal end can comprise an outer surface interfacing with the drive receptacle and the driven receptacle, respectively, such that, for each shaft, an intersection point defined between the shaft axis and the coupling axis is axially affixed along the shaft axis and along the coupling axis. The outer surfaces of the drive shaft distal end and the driven shaft proximal end can comprise a spherical surface. The drive receptacle and the driven receptacle can comprise a spherical surface.

In many embodiments, the drive shaft distal end and the driven shaft proximal end comprise interfacing gear teeth. For example, the drive shaft distal end can comprise a drive shaft gear tooth surface extending around the drive axis, the driven shaft proximal end can comprise a driven shaft gear tooth surface extending around the driven axis, and the drive shaft gear tooth surface can engage the driven shaft gear tooth surface so as maintain correspondence between the angles. In many embodiments, at least one of the drive shaft and the drive shaft gear tooth surface or the driven shaft and the driven shaft gear tooth surface are integrally formed. In many embodiments, the drive shaft gear tooth surface is defined by a drive shaft gear tooth profile extending radially from the drive axis, the driven shaft gear tooth surface is defined by a driven shaft gear tooth profile extending radially from the driven axis, and the drive shaft gear tooth surface engages the driven shaft gear tooth surface so as maintain substantial equivalence between the drive/coupler angle and the driven/coupler angle. In many embodiments, the drive shaft gear tooth surface comprises a revolute surface defined by rotating the drive shaft gear tooth profile about the drive axis, and the driven shaft gear tooth surface comprises a revolute surface defined by rotating the driven shaft gear tooth profile about the driven axis.

In another aspect, a minimally invasive surgical tool is provided. The surgical tool includes an instrument shaft, a drive shaft having a distal end and a drive axis, a driven shaft having a proximal end and a driven axis, a coupling member coupling the drive shaft with the driven shaft so that a rate of rotation of the drive and driven shafts are substantially equal when the drive axis and the driven axis are non-parallel, and an end effector coupled with the instrument shaft so that an orientation of the end effector can be varied in two dimensions relative to the instrument shaft. The drive shaft is mounted for rotation within the instrument shaft. The end effector comprises an articulated feature coupled with the driven shaft so that a rotation of the driven shaft about the driven axis produces an articulation of the feature.

In many embodiments, the drive shaft is axially and rotationally coupled with the coupling member, the driven shaft is axially and rotationally coupled with the coupling member, and the drive shaft engages the driven shaft. For example, the coupling member can comprise a first end and a second end with a coupling axis defined there between and the drive shaft distal end can be axially and rotationally coupled with the coupling member first end so that rotation of the drive shaft about the drive axis produces rotation of the coupling member about the coupling axis. The driven shaft proximal end can be axially and rotationally coupled with the coupling member second end so that rotation of the coupling member about the coupling axis produces rotation of the driven shaft about the driven axis. The drive shaft distal end can engage the driven shaft proximal end so as to maintain corresponding angles between the drive axis and the coupling axis, and the driven axis and the coupling axis when an angle between the drive axis and the driven axis varies during rotation of the shafts. The drive shaft distal end can comprise spherical gear teeth and the driven shaft proximal end can comprise spherical gear teeth engaging the drive shaft gear teeth. In many embodiments, at least one of the drive shaft and the drive shaft gear teeth or the driven shaft and the driven shaft gear teeth are integrally formed.

In many embodiments, the tool further comprises a coupling pin coupling the coupling member with the drive shaft so as to transfer rotational motion between the drive shaft and the coupling member. For example, the tool can further comprise a coupling member first end receptacle, a coupling pin crossing the receptacle, a drive shaft distal end outer surface interfacing with the receptacle, and a drive shaft distal end slot receiving the coupling pin throughout a range of angles between the coupling axis and the drive axis. Interaction between the coupling pin and the slot can couple the drive shaft with the coupling member so that rotation of the drive shaft produces rotation of the coupling member. The mechanism can further comprise a cross pin to couple the drive shaft with the coupling pin. The cross pin can be oriented transverse to the coupling pin and mounted for rotation relative to the drive shaft.

In many embodiments, at least one of the drive shaft distal end or the driven shaft proximal end comprises a protrusion. The coupling member can comprise a tubular structure defining a drive receptacle and a driven receptacle along the coupling axis and at least one of the drive receptacle or the driven receptacle can comprise a slot configured to receive the protrusion and accommodate the protrusion through a range of angles between the drive axis and the driven axis. The protrusion can interact with the slot so as to transfer rotational motion between at least one of the drive shaft or the driven shaft and the coupling member.

For a fuller understanding of the nature and advantages of the present invention, reference should be made to the ensuing detailed description and accompanying drawings. Other aspects, objects and advantages of the invention will be apparent from the drawings and detailed description that follows.

BRIEF DESCRIPTION OF THE DRAWINGS

FIG. 7 is a perspective view of the two degree-of-freedom wrist of FIG. 6, illustrating rotational degrees of freedom between an intermediate member of the wrist and a support member of the wrist, and between the intermediate member and the end effector body, in accordance with many embodiments.

FIG. 13a is a simplified diagrammatic illustration of a surgical tool having a second link coupled with a first link via a two degree-of-freedom joint, the second link comprising curved portion attachment features that are coupled with linked tension members, the view direction being parallel with a second axis of the two degree-of-freedom joint, in accordance with many embodiments.

FIG. 13b diagrammatically illustrates an attachment feature having a curved portion with a fixed center-of-curvature for its ordinary centerline, in accordance with many embodiments.

FIG. 13c shows section A-A of FIG. 13b.

FIG. 14e is a perspective view of a surgical tool having a second link coupled with a first link via a two degree-of-freedom joint, the second link comprising attachment lugs that are coupled with linked tension members having curved portion ends, in accordance with many embodiments.

FIG. 17 is a simplified diagrammatic illustration of a tool assembly having a mechanism for transmitting torque through an angle, in accordance with many embodiments.

FIG. 18 is a side view of a mechanism for transmitting torque through an angle in an inline configuration between a drive shaft and a driven shaft, in accordance with many embodiments.

FIG. 26 illustrates a compact wrist design, in accordance with many embodiments, having a two degree-of-freedom wrist that is articulated by linked tension members, and double universal joints to transmit torque through an angle across the wrist.

DETAILED DESCRIPTION

Figure 1:
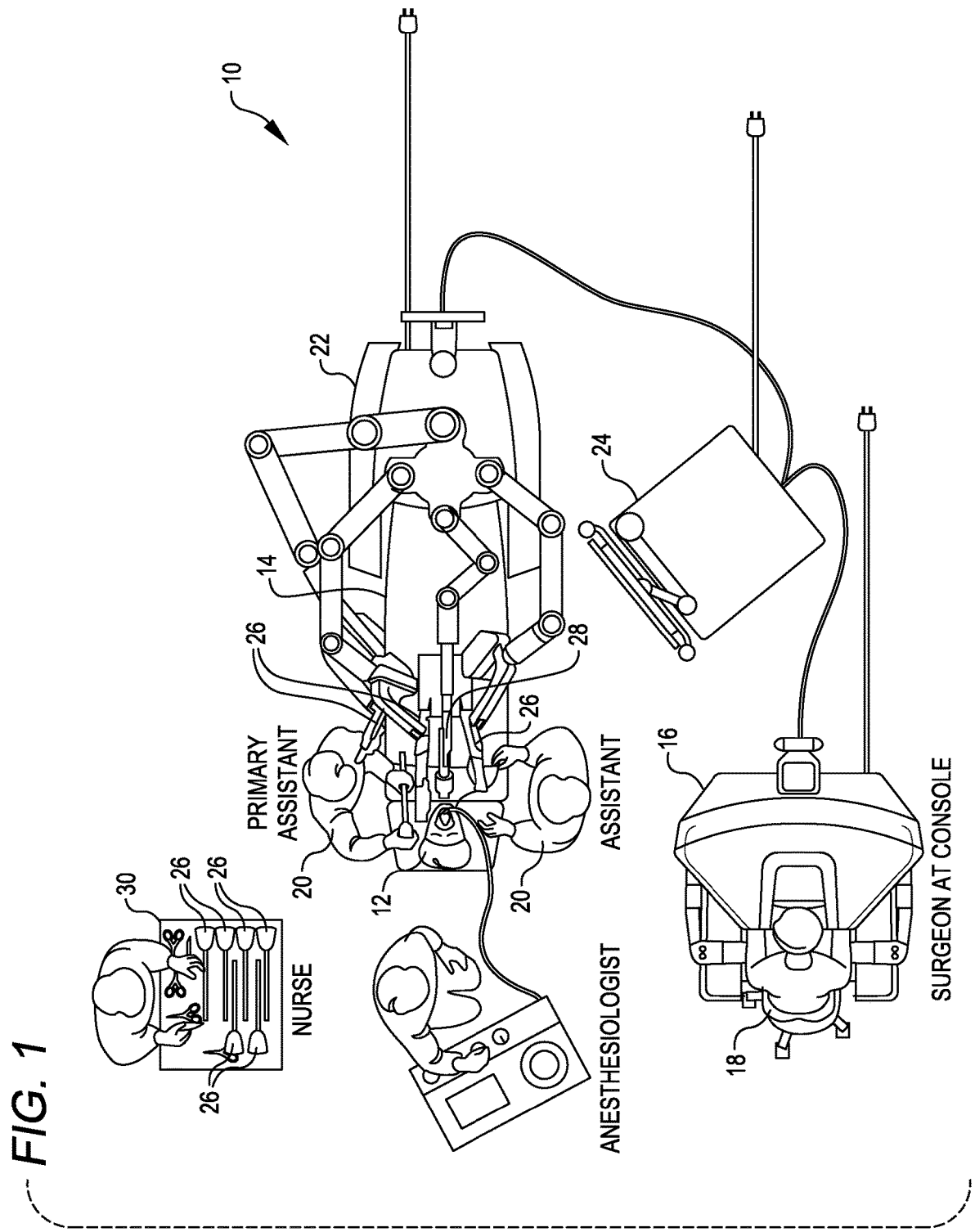
FIG. 1 is a plan view of a minimally invasive robotic surgery system being used to perform a surgery, in accordance with many embodiments.

In the following description, various embodiments of the present invention will be described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described.

Surgical tools with a two degree-of-freedom wrist mechanism, and related methods, are provided. In many embodiments, a two degree-of-freedom wrist includes an elongated intermediate wrist member that is pivotally coupled with both a distal end of an instrument shaft and an end effector body. The intermediate member can be pivotally coupled with the instrument shaft to rotate about a first axis that is transverse to an elongate direction of the instrument shaft. The end effector body can be pivotally coupled with the intermediate member so as to rotate about a second axis that is transverse to the first axis. Pivoting the intermediate member relative to the instrument shaft about the first axis, combined with pivoting an end effector body relative to the intermediate body about the second axis, can be used to reorient the end effector body relative to the instrument shaft in two dimensions. The ability to reorient the end effector body in two dimensions can be used to mimic the natural action of a surgeon's wrist, thereby providing a desirable amount of maneuverability for the end effector body.

In many embodiments, a two degree-of-freedom wrist is advantageously integrated within a minimally invasive surgical tool. For example, the intermediate wrist member can have a length that is roughly equivalent to the diameter of an instrument shaft and a width that is significantly less than the length, for example, a width that is less than one-third of the length; the width often being less than one-half the length, and in some cases the width being less than one-quarter the length. In many embodiments, a centrally located pivot is used that provides for rotation of the intermediate member relative to the shaft or the end effector body about an axis oriented transverse to the elongate direction of the intermediate body, and two co-axial peripherally located pivots are used that provide for rotation of the intermediate member relative to the shaft or the end effector body about an axis oriented parallel to the elongate direction of the intermediate body. The dimensions and the resulting motion of the intermediate member leaves adjacent areas open for routing end effector articulation and actuation components. Advantageously, articulation components can be routed so as to be spaced apart from the first and second axes while still being within a cross section of the minimally invasive tool, thereby allowing the use of axial force articulation components, for example, tensile force articulation components. Exemplary embodiments may employ both cables and rotational drive shafts that are offset from the intermediate wrist member, while an outer diameter of the tool (including the articulation components, end effector, and wrist joint system) will preferably be less than 1 inch, and often being approximately one-half inch. The intermediate wrist member can include routing provisions with guidance features to route one or more control cables through the intermediate wrist member. The wrist can be configured to transmit roll axis torque (e.g., 0.33 N m) across the wrist. The wrist can be configured with hard stops to limit the range of motion of the instrument to protect other components from damage due to angular over travel. The wrist can have a compact length, with pitch axis to yaw axis distance adjustable down to zero offset.

In many embodiments, a two degree-of-freedom wrist includes internal passages for guiding control cables. The internal passages can be configured to inhibit altering control cable tensions during pivoting about the first and second axes.

Improved surgical and/or robotic wrist structures with wrist articulation by linked tension members are also provided. In many embodiments, linked tension members are used to articulate a second link that is coupled with a first link via a two degree-of-freedom joint. The linked tension members can be coupled with the second link via attachment features disposed on the second link. The geometries of the two degree-of-freedom joint, the linked tension members, and the attachment features can be selected so that opposed axial movement of the tension members angularly orients the second link relative to the first link so as to inhibit changes in tension in the tension members. In many embodiments, diagonally opposed tension members are paired and actuated by an actuation mechanism. For example, diagonally opposed tension members can be coupled with at least one control cable, and the at least one control cable can be actuated by a motor driven capstan.

The disclosed wrist articulation via linked tension members may be advantageously employed in surgical tools having a second link coupled with an elongate first link via a two degree-of-freedom joint. The disclosed wrist articulation may be particularly advantageous when employed in a minimally invasive surgical tool. Minimally invasive surgical tools that are reliable and that have smooth operational characteristics are desirable. By inhibiting changes in tension of the linked tension members, detrimental control cable slack and/or overstressing of tool components may be avoided. Actuating linked tension members via a linear drive mechanism, for example, a motor driven capstan, may provide smooth operational characteristics. The disclosed wrist articulation also enables surgical tools with reduced length distal of the first link, which improves access in a confined body space, angle of access to body structures, and visibility of body structures. The disclosed wrist articulation enables wrist articulation without interference with additional mechanisms passing through the wrist, for example, drive shafts. The disclosed wrist articulation may also provide increased longevity by avoiding the use of stranded cables in the wrist. The disclosed wrist articulation can also be used to provide 60 degrees of wrist articulation angle. The disclosed wrist articulation can also employ small diameter (e.g., hypodermic) tubing, which is advantageous for being readily attachable to flexible cables driven by motor driven capstans.

In many embodiments, a minimally invasive surgical tool having wrist articulation via linked tension members can include a second link pivotally mounted to a first link via a two degree-of-freedom joint. The joint can have a first axis of rotation transverse to the first link and a second axis of rotation transverse to the first axis of rotation. The second link can be coupled with four linked tension members so as to articulate the second link relative to the first link. The four tension members can be spaced apart from the two axes of the two degree-of-freedom joint by locating one tension member in each quadrant defined by the two axes while still being within the cross section of the minimally invasive tool. In exemplary embodiments, an outer diameter of the tool (including the linked tension members, other end effector actuation components such as control cables and drive shafts, the end effector, and the wrist joint system) will preferably be less than 1 inch, and often approximately one-half inch.

Mechanisms for transmitting torque through an angle, minimally invasive surgical tools comprising a mechanism for transmitting torque through an angle, and related methods are also provided. Such mechanisms have a relatively simple design, which may increase the reliability of the mechanism by reducing the number of possible failure points. For example, in many embodiments, a mechanism for transmitting torque through an angle may have a reduced part count as compared to existing mechanisms.

The disclosed mechanisms may provide for a smooth transmission of torque through a range of angles. In many embodiments, a mechanism for transmitting torque through an angle is operable to transmit torque through an angle exceeding 60 degrees. In many embodiments, the rotational speed of an output shaft (e.g., a driven shaft) is substantially equal to the rotational speed an input shaft (e.g., a drive shaft), even when the input and output shafts are non-parallel, which may provide for a smooth transmission of torque through an angle by avoiding the generation of vibration forces associated with non-equivalent rotational speeds. The outer diameter of the mechanism (including the shafts, end effector, and joint system) will preferably be less than 1 inch, often being less than ½ inch, and ideally being no more than 8 mm (or in some cases, no more than 5 mm). To allow multiple shaft drive systems to fit within a single wrist, the drive shafts, driven shafts, and couplers of the mechanisms described herein will preferably fit within a diameter of no more than 5 mm, and ideally within a diameter of no more than 3 mm. The torque transmitted across the joint will often be more than 0.2 N m, and ideally being more than 0.3 N m. To produce the desired work by the end effector in the desired amount of time, the shafts and joint system will typically be rotatable at speeds of at least 100 rpm, and ideally being at least several thousand rpm. The joints will preferably have a life of at least several minutes of operation when driven at maximum torque and wrist angle, and ideally of at least several hours. The exemplary drive shaft to driven shaft joint assembly, excluding the shafts themselves, includes fewer than 10 separately fabricated and/or machined parts, and in many embodiments only 3 separately fabricated and/or machined parts.

Available materials can be used to fabricate components of the disclosed mechanisms. In many embodiments, the drive shaft, driven shaft, and coupler can be fabricated from, for example, 465 stainless steel, condition H950. The drive and driven shaft ends can be integral to the shafts. The cross pins can be fabricated from, for example, Nitronic 60 stainless steel, 30 percent cold worked.

The disclosed mechanisms may be particularly beneficial when used as part of a minimally invasive surgical tool. As discussed above, minimally invasive surgical tools are typically introduced into a patient through a cannula sleeve, which constrains the diameter of the tool. The relatively simple design of the disclosed mechanisms can be sized for use within a minimally invasive surgical tool. The relatively simple design also may reduce possible failure points, a reduction which may increase the reliability of a minimally invasive surgical tool. The ability to configure the disclosed mechanisms to transmit torque through an angle exceeding 60 degrees enables the use of a relatively large amount of articulation between an end effector and an instrument shaft of a minimally invasive surgical tool. The ability of the disclosed mechanisms to smoothly transmit torque through an angle through the use of equivalent rotational speeds may also be beneficial by avoiding harm to the patient and/or the surgical tool that may result from the generation of vibration movements and/or forces.

Referring now to the drawings, in which like reference numerals represent like parts throughout the several views, in accordance with many embodiments, FIG. 1 through FIG. 5b illustrate aspects of minimally invasive robotic surgery systems, FIG. 6 through FIG. 12 illustrate aspects of two degree-of-freedom wrists, FIG. 13a through FIG. 16 illustrate aspects of wrist articulation by linked tension members, and FIG. 17 through FIG. 25b illustrate aspects of mechanisms for transmitting torque through an angle. As can be appreciated, the foregoing features can be utilized individually, or in any combination. For example, FIGS. 10, 13g, 13h, 13i, and 26 illustrates a compact wrist design having a two degree-of-freedom wrist that is articulated by linked tension members as disclosed herein, as well as the use of double universal joints to transmit torques through an angle across the two degree-of-freedom wrist.

Minimally Invasive Robotic Surgery

FIG. 1 is a plan view illustration of a Minimally Invasive Robotic Surgical (MIRS) system 10, typically used for performing a minimally invasive diagnostic or surgical procedure on a Patient 12 who is lying down on an Operating table 14. The system can include a Surgeon's Console 16 for use by a Surgeon 18 during the procedure. One or more Assistants 20 may also participate in the procedure. The MIRS system 10 can further include a Patient-Side Cart 22 (surgical robot), and an Electronics Cart 24. The Patient-Side Cart 22 can manipulate at least one removably coupled tool assembly 26 (hereinafter simply referred to as a "tool") through a minimally invasive incision in the body of the Patient 12 while the Surgeon 18 views the surgical site through the Console 16. An image of the surgical site can be obtained by an endoscope 28, such as a stereoscopic endoscope, which can be manipulated by the Patient-Side Cart 22 so as to orient the endoscope 28. The Electronics Cart 24 can be used to process the images of the surgical site for subsequent display to the Surgeon 18 through the Surgeon's Console 16. The number of surgical tools 26 used at one time will generally depend on the diagnostic or surgical procedure and the space constraints within the operating room among other factors. If it is necessary to change one or more of the tools 26 being used during a procedure, an Assistant 20 may remove the tool 26 from the Patient-Side Cart 22, and replace it with another tool 26 from a tray 30 in the operating room.

Figure 2:
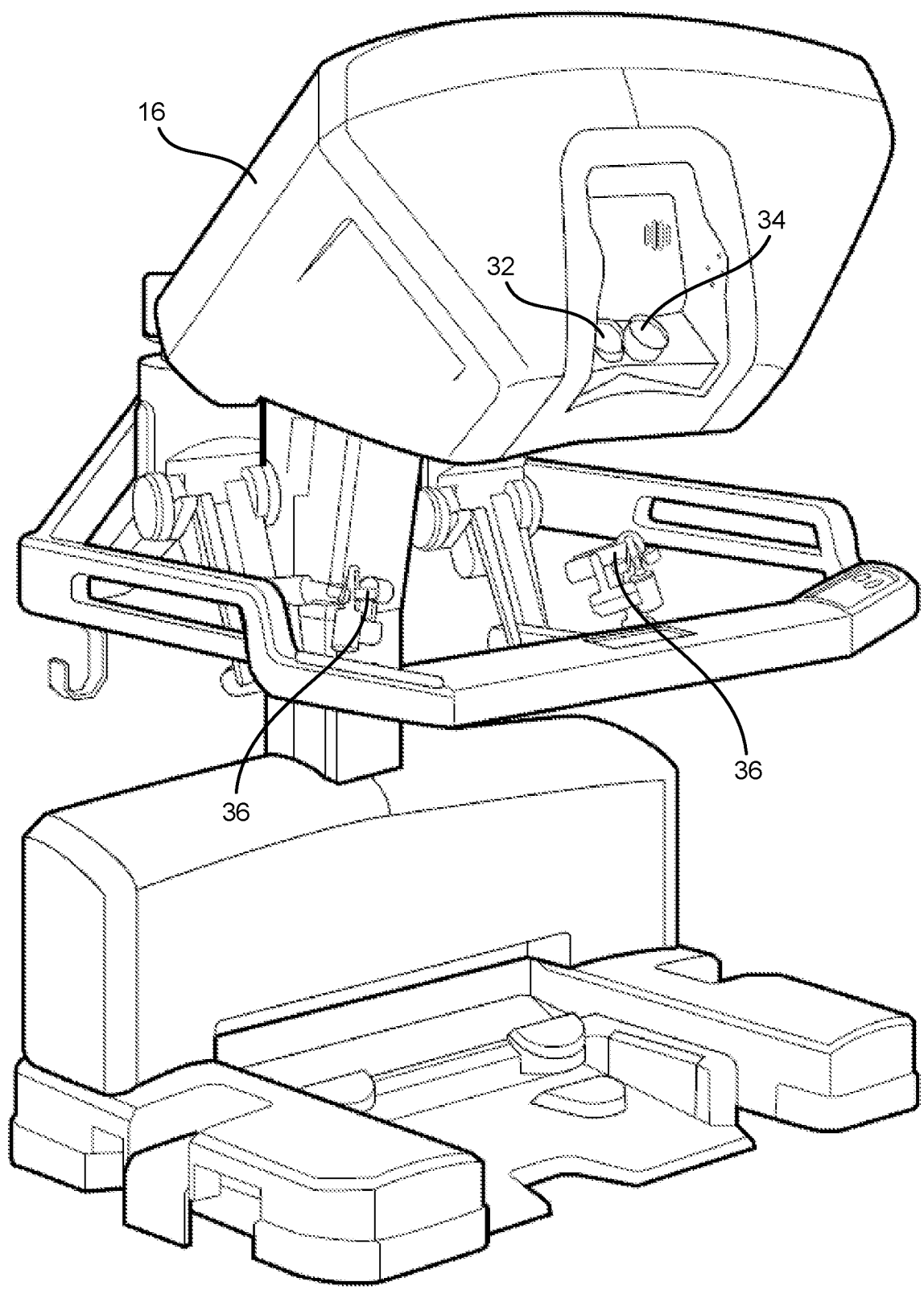
FIG. 2 is a perspective view of a surgeon's control console for a robotic surgery system, in accordance with many embodiments.

FIG. 2 is a perspective view of the Surgeon's Console 16. The Surgeon's Console 16 includes a left eye display 32 and a right eye display 34 for presenting the Surgeon 18 with a coordinated stereo view of the surgical site that enables depth perception. The Console 16 further includes one or more input control devices 36, which in turn cause the Patient-Side Cart 22 (shown in FIG. 1) to manipulate one or more tools. The input control devices 36 will provide the same degrees of freedom as their associated tools 26 (shown in FIG. 1) so as to provide the Surgeon with telepresence, or the perception that the input control devices 36 are integral with the tools 26 so that the Surgeon has a strong sense of directly controlling the tools 26. To this end, position, force, and tactile feedback sensors (not shown) may be employed to transmit position, force, and tactile sensations from the tools 26 back to the Surgeon's hands through the input control devices 36.

The Surgeon's Console 16 is usually located in the same room as the patient so that the Surgeon may directly monitor the procedure, be physically present if necessary, and speak to an Assistant directly rather than over the telephone or other communication medium. However, the Surgeon can be located in a different room, a completely different building, or other remote location from the Patient allowing for remote surgical procedures (i.e., operating from outside the sterile field).

Figure 3:
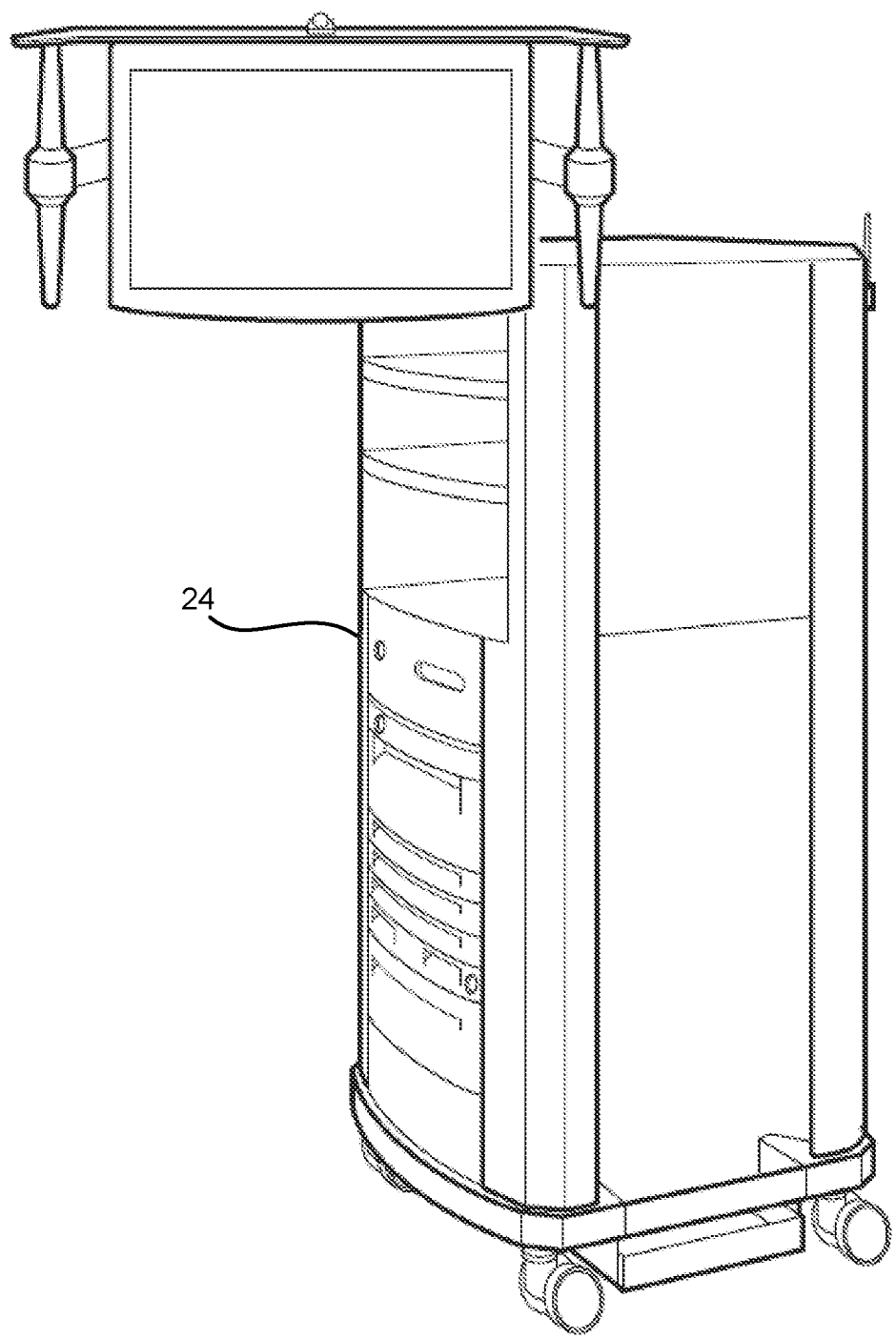
FIG. 3 is a perspective view of a robotic surgery system electronics cart, in accordance with many embodiments.

FIG. 3 is a perspective view of the Electronics Cart 24. The Electronics Cart 24 can be coupled with the endoscope 28 and can include a processor to process captured images for subsequent display, such as to a Surgeon on the Surgeon's Console, or on any other suitable display located locally and/or remotely. For example, where a stereoscopic endoscope is used, the Electronics Cart 24 can process the captured images so as to present the Surgeon with coordinated stereo images of the surgical site. Such coordination can include alignment between the opposing images and can include adjusting the stereo working distance of the stereoscopic endoscope. As another example, image processing can include the use of previously determined camera calibration parameters so as to compensate for imaging errors of the image-capture device, such as optical aberrations.

Figure 4:
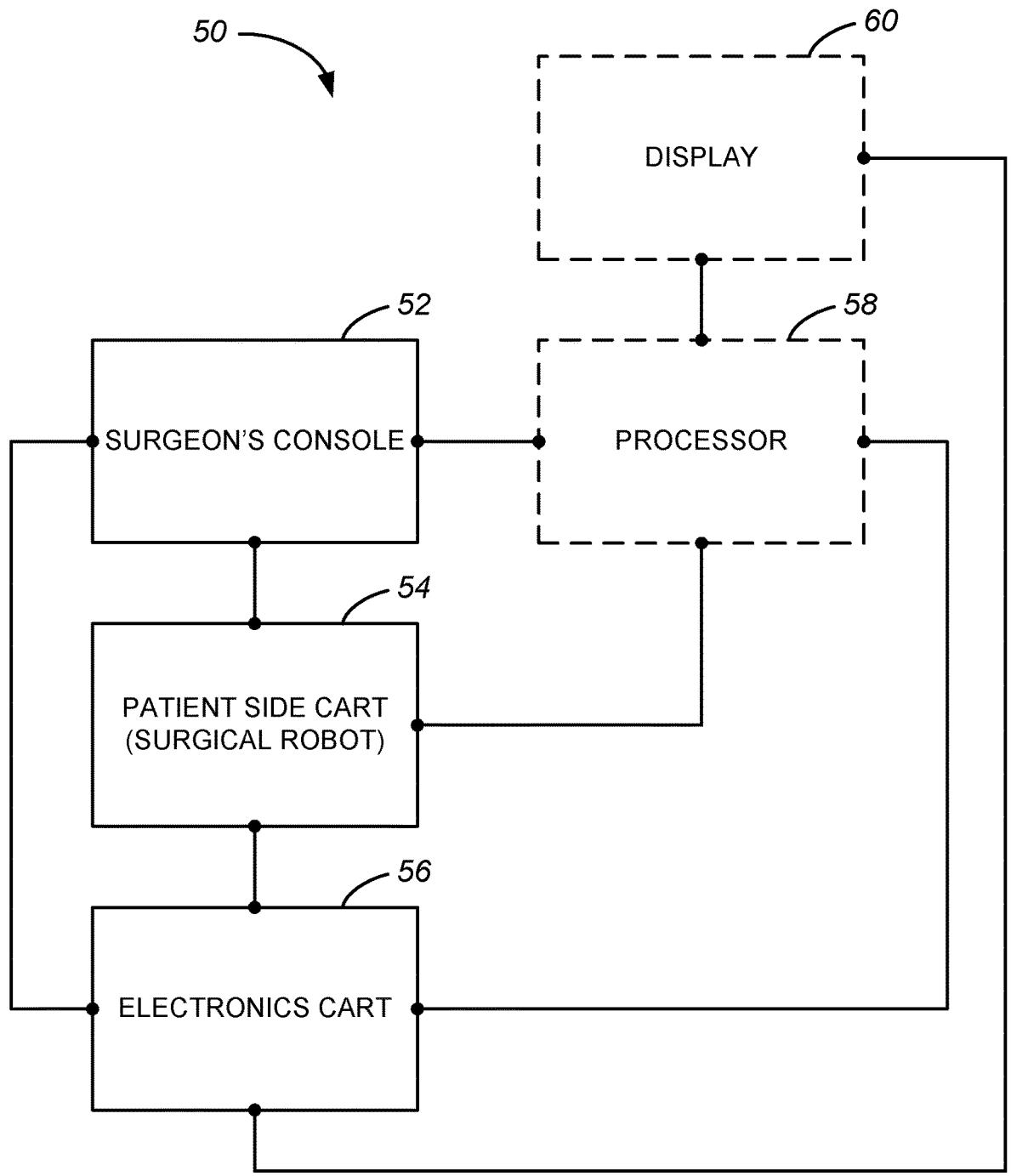
FIG. 4 is a simplified diagrammatic illustration of a robotic surgery system, in accordance with many embodiments.

FIG. 4 diagrammatically illustrates a robotic surgery system 50 (such as MIRS system 10 of FIG. 1). As discussed above, a Surgeon's Console 52 (such as Surgeon's Console 16 in FIG. 1) can be used by a Surgeon to control a Patient-Side Cart (Surgical Robot) 54 (such as Patient-Side Cart 22 in FIG. 1) during a minimally invasive procedure. The Patient-Side Cart 54 can use an imaging device, such as a stereoscopic endoscope, to capture images of the procedure site and output the captured images to an Electronics Cart 56 (such as the Electronics Cart 24 in FIG. 1). As discussed above, the Electronics Cart 56 can process the captured images in a variety of ways prior to any subsequent display. For example, the Electronics Cart 56 can overlay the captured images with a virtual control interface prior to displaying the combined images to the Surgeon via the Surgeon's Console 52. The Patient-Side Cart 54 can output the captured images for processing outside the Electronics Cart 56. For example, the Patient-Side Cart 54 can output the captured images to a processor 58, which can be used to process the captured images. The images can also be processed by a combination the Electronics Cart 56 and the processor 58, which can be coupled together so as to process the captured images jointly, sequentially, and/or combinations thereof. One or more separate displays 60 can also be coupled with the processor 58 and/or the Electronics Cart 56 for local and/or remote display of images, such as images of the procedure site, or any other related images.

Figure 5B:
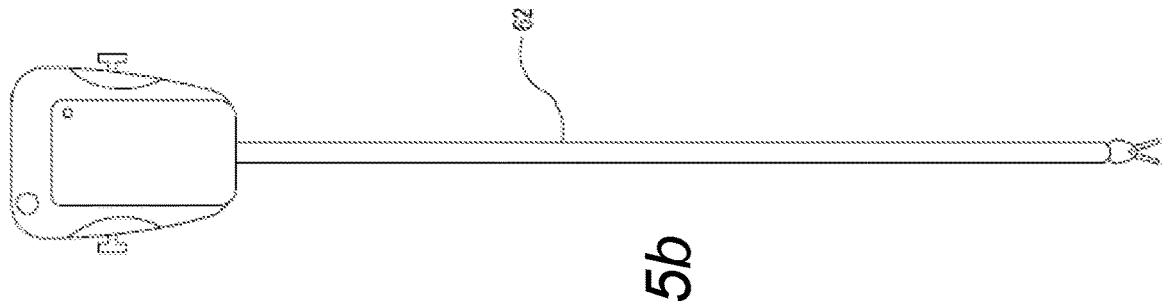
FIG. 5b is a front view of a robotic surgery tool.
Figure 5A:
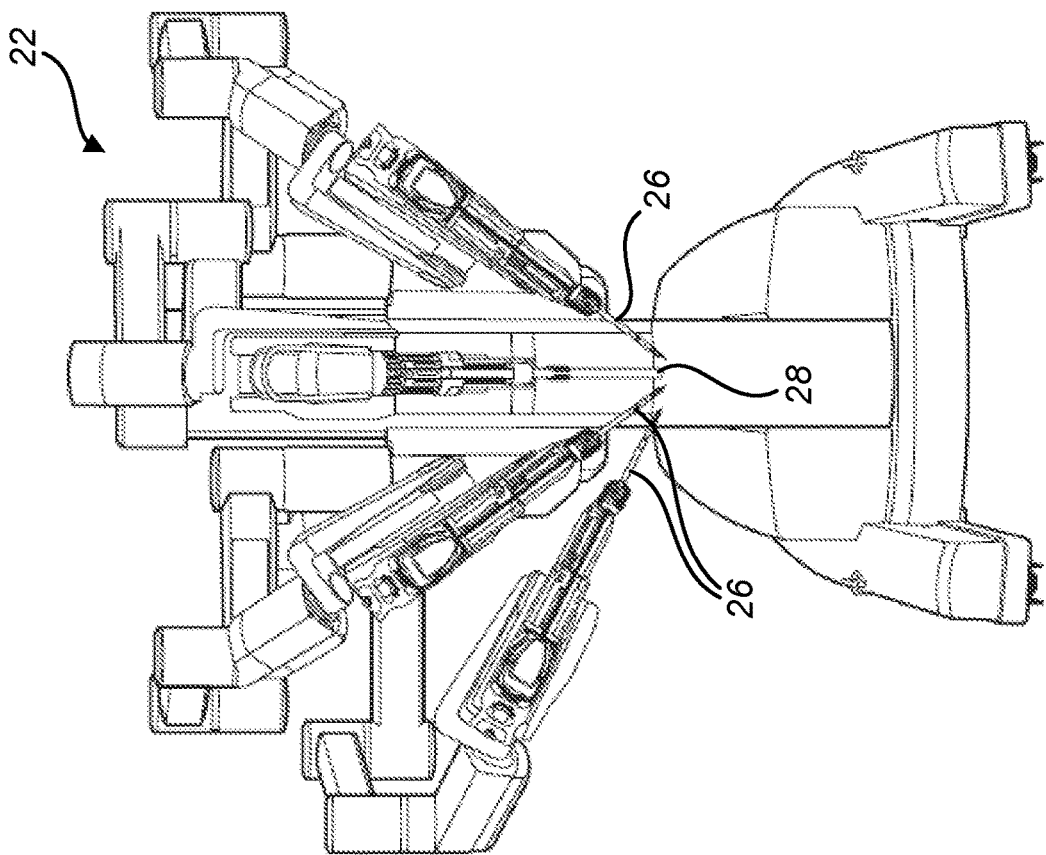
FIG. 5a is a front view of a patient-side cart (surgical robot) of a robotic surgery system, in accordance with many embodiments.

FIGS. 5a and 5b show a Patient-Side Cart 22 and a surgical tool 62, respectively. The surgical tool 62 is an example of the surgical tools 26. The Patient-Side Cart 22 shown provides for the manipulation of three surgical tools 26 and an imaging device 28, such as a stereoscopic endoscope used for the capture of images of the site of the procedure. Manipulation is provided by robotic mechanisms having a number of robotic joints. The imaging device 28 and the surgical tools 26 can be positioned and manipulated through incisions in the patient so that a kinematic remote center is maintained at the incision so as to minimize the size of the incision. Images of the surgical site can include images of the distal ends of the surgical tools 26 when they are positioned within the field-of-view of the imaging device 28.

Two Degree-of-Freedom Wrist

Figure 6:
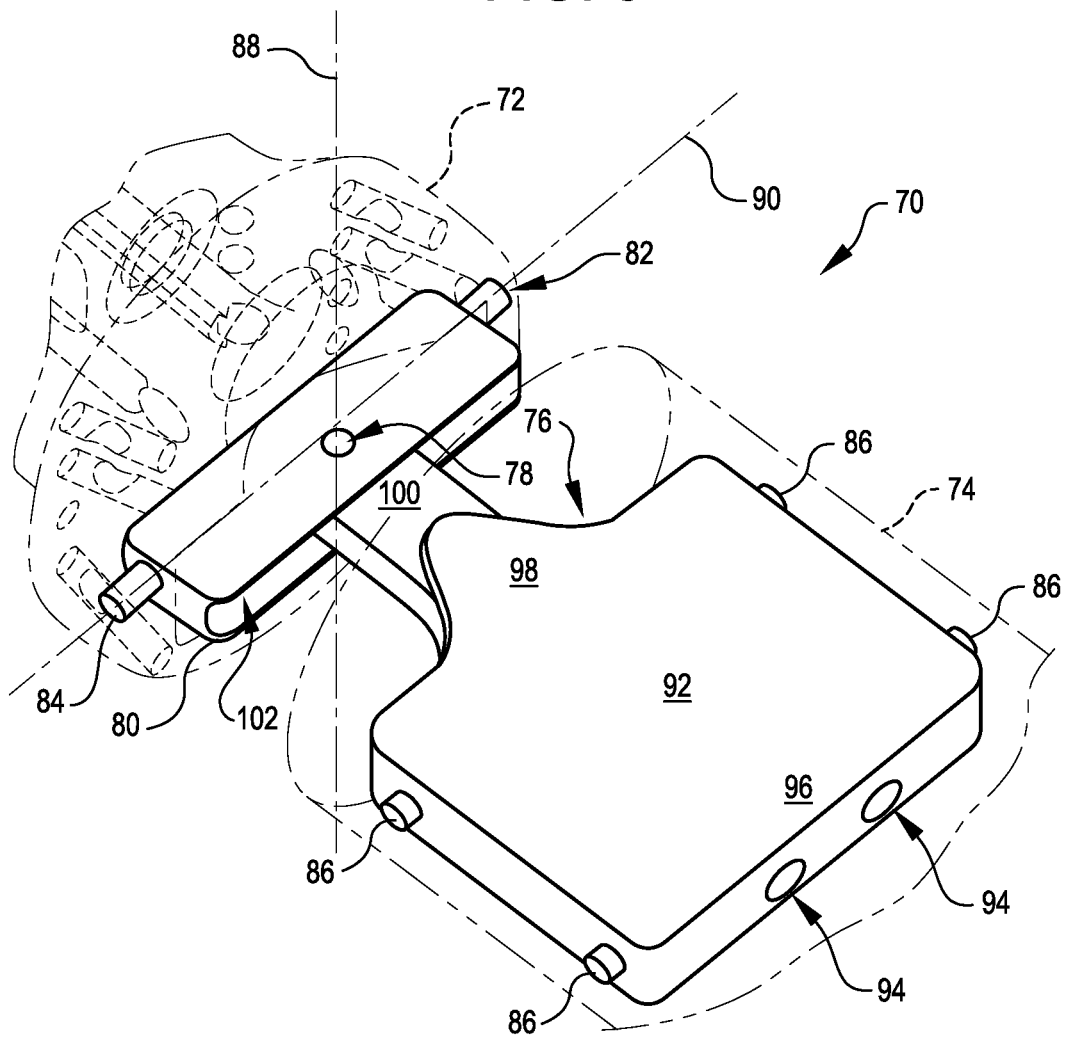
FIG. 6 is a perspective view of a two degree-of-freedom wrist coupling an end effector body with an instrument shaft, in accordance with many embodiments.

FIG. 6 is a perspective view of a two degree-of-freedom wrist 70 coupling an end effector body 72 with an instrument shaft 74, in accordance with many embodiments. The wrist 70 includes a support member 76, a first hinge point 78, an intermediate member 80, a second hinge point 82, and a third hinge point 84. The support member 76 is fixedly mounted to the instrument shaft 74 via four attachment features 86 (e.g., mechanical fasteners) so as to be positioned within a bore of the instrument shaft 74 as illustrated. The intermediate member 80 is pivotally coupled with the support member 76 for rotation about a first axis 88 via the centrally-located first hinge point 78. The end effector body 72 is pivotally coupled with the intermediate member 80 for rotation about a second axis 90 via the peripherally-located second hinge point 82 and the peripherally-located third hinge point 84. The second hinge point 82 and the third hinge point 84 are coaxial and aligned with the second axis 90. The second axis 90 pivots with the intermediate member about the first axis 88.

The first axis 88 and the second axis 90 can be positioned to provide a compact two degree-of-freedom wrist with desired kinematics and/or spatial characteristics. For example, the first axis 88 and the second axis 90 can be coplanar, and thereby provide a compact wrist member with ball-joint like kinematics. In many embodiments, the first axis 88 and the second axis 90 are separated by a desired distance along an elongate direction of the instrument shaft 74. Such a separation can be used to approximate and/or match the kinematics of the wrist mechanism to the kinematics of actuation system components used to orient the end effector body 72 relative to the instrument shaft 74 via the two degree-of-freedom wrist. In many embodiments, the first axis 88 and the second axis 90 are separated by a desired distance along the elongate direction of the instrument shaft 74 so as to provide a two degree-of-freedom wrist with a desired combination of compactness and kinematics that approximately match the kinematics of the actuation system components used to orient the end effector body 72 relative to the instrument shaft 74. For example, if a 4 mm separation between the first axis 88 and the second axis 90 would match the kinematics of the actuation system orientation components used, the two degree-of-freedom wrist can be configured with a smaller separation (e.g., 2 mm) so as to provide a more compact wrist. In many embodiments, such a separation distance compromise can be employed without inducing any significant detrimental operating characteristics from not exactly matching the kinematics of the actuation system orientation components used. The first axis 88 and the second axis 90 can be positioned to provide a compact two degree-of-freedom wrist with desired spatial characteristics. For example, the first axis 88 and the second axis 90 can be separated to provide additional space for actuation system components and related attachment features.

The support member 76 provides a transitional fitting between the instrument shaft 74 and the first hinge point 78. The support member 76 includes a rectangular main portion 92 and a cantilevered distal portion 100. The rectangular main portion 92 has a thickness that is less than the inside diameter of the instrument shaft bore, which leaves two adjacent regions of the bore open for the routing of articulation and/or actuation components (not shown). The support-member main portion 92 includes two internal passages 94, which can be used to guide end effector control cables routed within the instrument-shaft bore. The internal passages 94 are routed between a proximal end 96 of the main portion 92 and a distal end 98 of the main portion 92 and are generally aligned with the elongate direction of the instrument shaft 74. As will be discussed further below, in many embodiments, the internal passages 94 are configured to work in conjunction with cable guide surfaces of the intermediate member to inhibit altering control cable tensions during pivoting about the first and second axes by maintaining constant control cable path lengths. The cantilevered distal portion 100 has an attachment lug that receives a single pivot shaft of the first hinge point 78. The use of a single pivot shaft is merely exemplary, and other pivot joint components can be used in place of the first hinge point 78, for example, two pivot pins aligned on the same axis can be used. The support member 76 is configured to place the first hinge point 78 (and therefore the first axis 88) at a desired location relative to the instrument shaft 74 and the end effector body 72, for example, to provide clearance between the end effector body 72 and the instrument shaft 74 necessary for a desired range of reorientation of the end effector body 72 relative to the instrument shaft 74.

The intermediate member 80 provides a transitional fitting between the first hinge point 78, the second hinge point 82, and the third hinge point 84. The intermediate member 80 includes an elongate rectangular main portion that has a thickness that is less than the inside diameter of the instrument shaft bore (e.g., similar to the thickness of main portion 92), which leaves two adjacent regions open for the routing of articulation and/or actuation components (not shown). The intermediate member 80 includes a central slot 102 configured to receive the attachment lug of the support-member distal portion 100. The central slot 102 is configured to accommodate the attachment lug of the distal portion 100 throughout a range of rotation of the intermediate member 80 about the first axis 88. The central slot 102 can also be configured to accommodate end effector control cables (not shown) that are routed through the support-member internal passages 94. The central slot 102 can also include surfaces configured to guide end effector control cables. As will be discussed further below, in many embodiments, the central-slot cable-guiding surfaces are configured to inhibit altering control cable tensions during pivoting about the first and second axes by maintaining substantially constant control cable path lengths. In many embodiments, the central-slot cable guiding surfaces work in conjunction with the internal passages 94 to maintain constant control cable path lengths during pivoting about the first and second axes. The central slot 102 also provides opposing attachment flanges that receive the single pivot shaft of the first hinge point 78. The second hinge point 82 includes a pivot shaft cantilevered from a first end of the intermediate member 80. The third hinge point 84 includes a pivot shaft cantilevered from an opposing second end of the intermediate member 80. The use of cantilevered pivot shafts is merely exemplary, and other suitable pivot joints can be used. In many embodiments, the positions and orientations of the second and third hinge points 82, 84 (and hence the position and orientation of the second axis 90) are selected so as to provide a desired position and orientation of the second axis 90 relative to the first axis 88. For example, in many embodiments, the first and second axes are non-coplanar. In many embodiments, the first and second axes are coplanar. In many embodiments, the position and/or orientation of the second axis 90 relative to the first axis 88 is selected to provide desired kinematics for the movement of the end effector body 72 relative to the instrument shaft 74.

FIG. 7 is a perspective view of the two degree-of-freedom wrist 70 of FIG. 6, illustrating the rotational degree-of-freedom between the intermediate member 80 and the support member 76 about the first axis 88, and the rotational degree-of-freedom between the end effector body (not shown) and the intermediate member 80 about the second axis 90, in accordance with many embodiments. The support member 76 is mounted to the instrument shaft 74 so as to position the first hinge point 78 as a desired location distal from the distal end of the instrument shaft 74, for example, to provide clearance between the end effector body and the instrument shaft so as to provide space for articulation of the end effector body. The intermediate-member central slot 102 is open to the side of the intermediate member 80 adjacent to the end effector body so as to accommodate routing of end effector control cables (not shown). From the view direction of FIG. 7, one internal passage 94 of the support member 76 is visible and the other internal passage 94 is hidden from view. In many embodiments, one control cable is routed through each of the two internal passages 94. Each of these two control cables is further routed through the intermediate-member central slot 102, one on each side of the first axis 88.

Figure 8A:
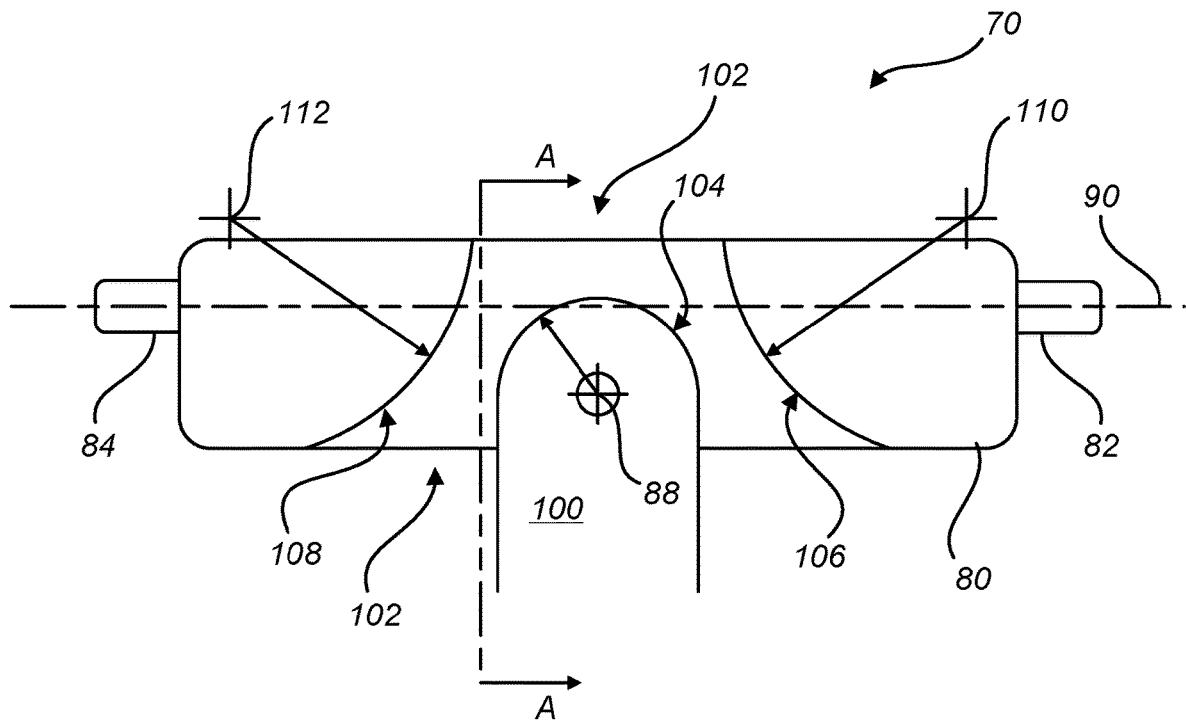
FIG. 8a is a simplified diagrammatic illustration of a support-member cable-guiding surface and intermediate-member cable-guiding surfaces, in accordance with many embodiments.

FIG. 8a is a diagrammatic cross-sectional view of the wrist 70 taken through the second axis 90 and normal to the first axis 88, and which shows illustrative support and intermediate member cable guiding surfaces. The support member distal end 100 includes a first pulley surface 104 with a curved arc shape such that the centerline of the curved arc shape is aligned with the first axis 88. Inner surfaces of the intermediate member slot 102 define a second pulley surface 106 and a third pulley surface 108 with curved arc shapes such that centerlines of the curved arc shapes (second pulley centerline 110 and third pulley centerline 112) are offset from and parallel to the first axis 88. Although the pulley surfaces illustrated have constant curvatures, this is merely exemplary and other suitable surfaces can be used. The first pulley surface 104, second pulley surface 106, and third pulley surface 108 provide smooth cable-guiding surfaces that can guide control cables for rotations of the intermediate body 80 about the first axis 88 (and therefore for rotations of the end effector body about the first axis 88). In many embodiments, the first pulley surface 104, second pulley surface 106, and third pulley surface 108 inhibit altering control cable tensions during pivoting about the first axis by maintaining constant control cable path lengths. In many embodiments, the first pulley surface 104, second pulley surface 106, and third pulley surface 108 work in conjunction with the internal passages 94 to maintain constant control cable path lengths during pivoting about the first axis.

Figure 8B:
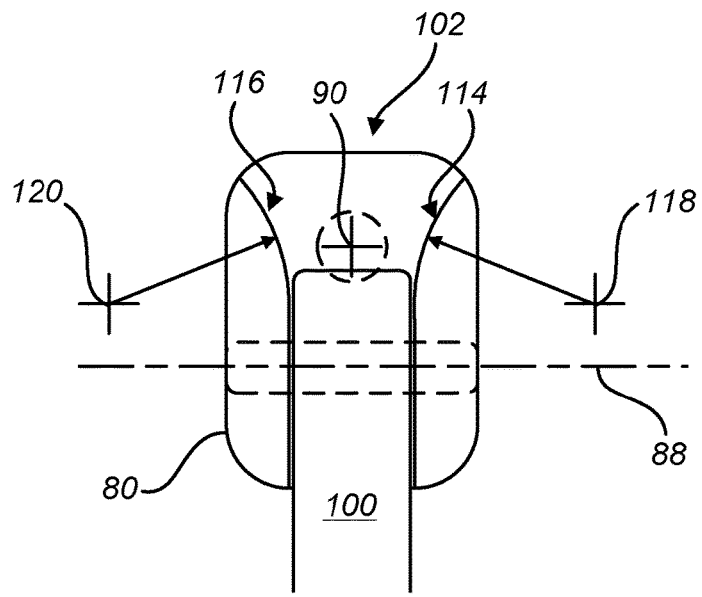
FIG. 8b is simplified diagrammatic illustration of intermediate-member cable-guiding surfaces, in accordance with many embodiments.

FIG. 8b is a simplified diagrammatic illustration of additional intermediate-member cable-guiding surfaces, in accordance with many embodiments. FIG. 8b illustrates cross section AA of FIG. 8a. Inner surfaces of the intermediate-member slot 102 further define a fourth pulley surface 114 and a fifth pulley surface 116 with curved arc shapes with centerlines of the curved arc shapes (fourth pulley centerline 118 and fifth pulley centerline 120) that are offset from and parallel to the second axis 90. Although the pulley surfaces illustrated have constant curvatures, this is merely exemplary and other suitable surfaces can be used. The fourth pulley surface 114 and the fifth pulley surface 116 provide smooth cable-guiding surfaces that can guide control cables for rotations of the end effector body relative to the intermediate body 80 about the second axis 90. In many embodiments, the fourth pulley surface 114 and the fifth pulley surface 116 inhibit altering control cable tensions during pivoting about the second axis by maintaining substantially constant control cable path lengths. In many embodiments, the fourth pulley surface 114 and the fifth pulley surface 116 work in conjunction with the internal passages 94 to maintain constant control cable path lengths during pivoting about the second axis.

Figure 9:
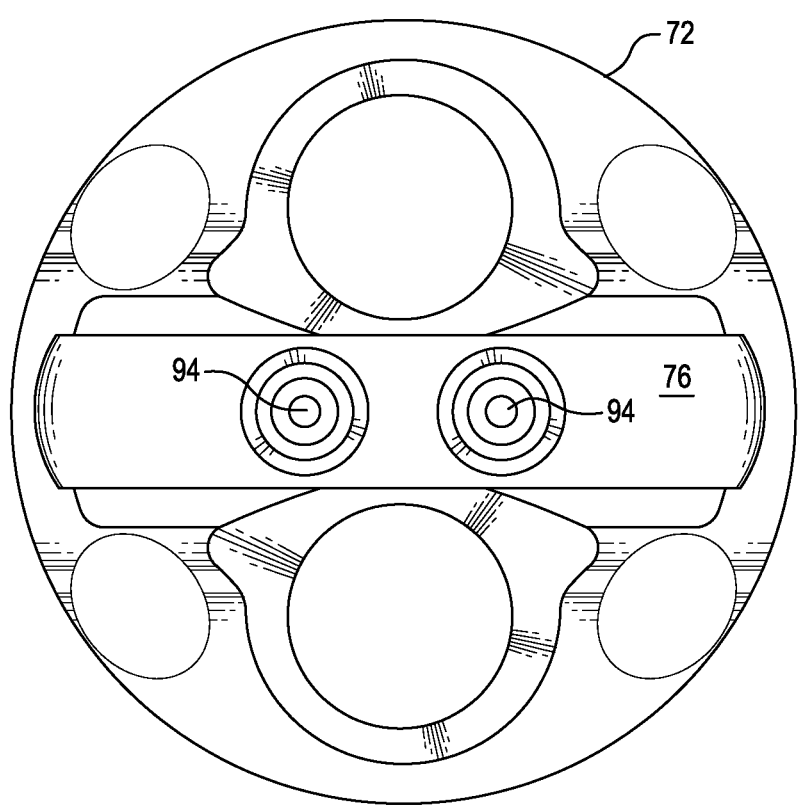
FIG. 9 is an end view of the support member of FIGS. 6 and 7, illustrating entrances to internal passages for guiding control cables, in accordance with many embodiments.

FIG. 9 is a proximal end view of the support member 76 of FIGS. 6 and 7, illustrating entrances to the internal passages 94 for guiding control cables of an actuation system, in accordance with many embodiments. The support member internal passages 94 can be used to constrain the cross-sectional position of the control cables at the distal end of the instrument shaft.

Figure 10:
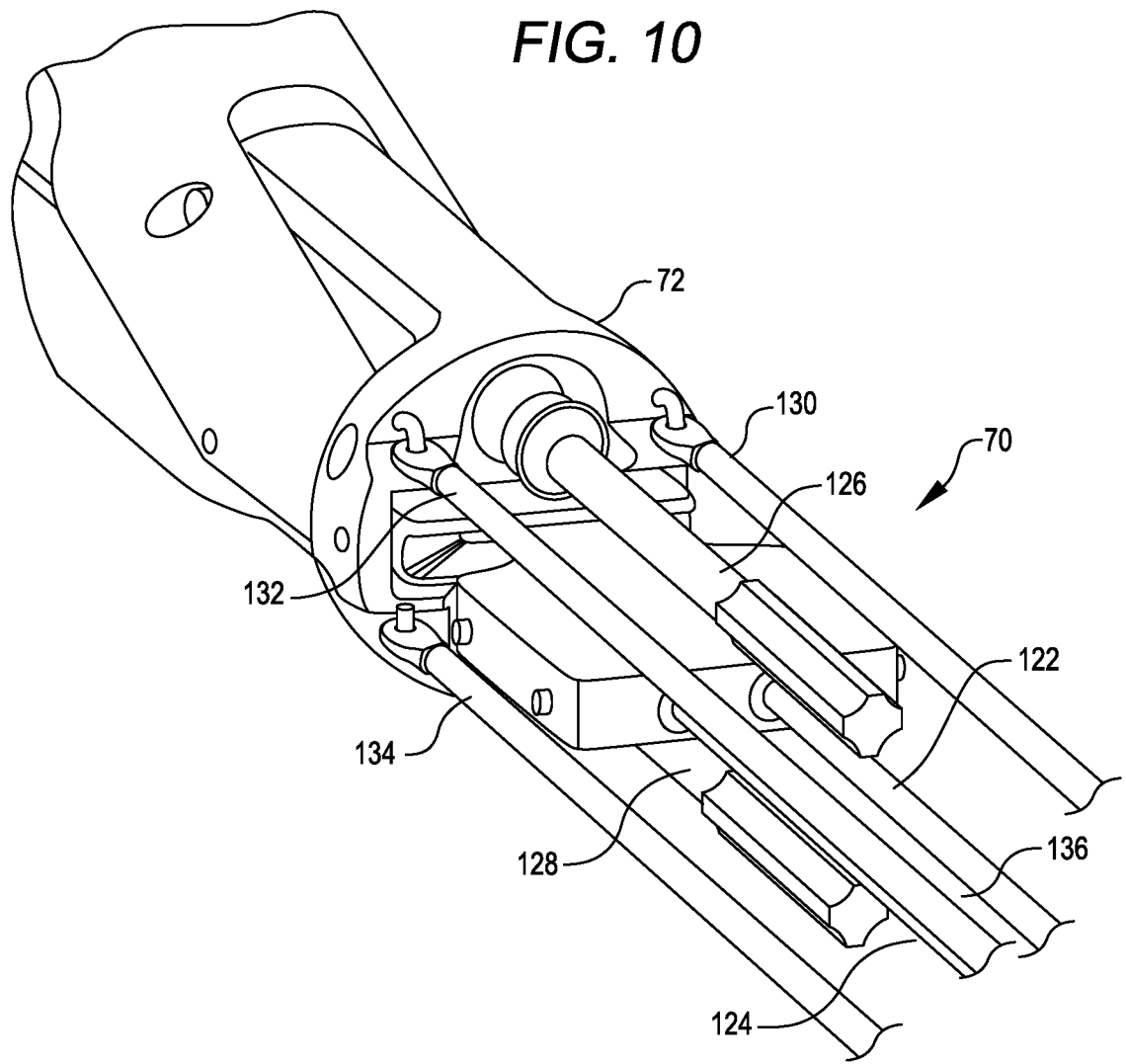
FIG. 10 is a perspective view of the two degree-of-freedom wrist of FIGS. 6, and 7, illustrating the routing of actuation system components adjacent opposite sides of the two degree-of-freedom wrist and the routing of control cables through the two degree-of-freedom wrist, in accordance with many embodiments.

FIG. 10 is a perspective view of the two degree-of-freedom wrist 70 of FIGS. 6, 7, and 8, showing an illustrative routing of actuation system components along two sides of the two degree-of-freedom wrist 70 and routing of control cables 122,124 through the two degree-of-freedom wrist 70, in accordance with many embodiments. The generally planar configuration of the two degree-of-freedom wrist, and its central location within the shaft that supports it, leaves adjacent areas open for the routing of such actuation system components. In the illustrated embodiment, these actuation systems components include a first drive shaft assembly 126 routed above the wrist, a second drive shaft assembly 128 routed below the wrist, end effector articulation pull rods 130, 132, 134, and 136 routed above and below the wrist, and control cables 122,124 routed through the wrist via the internal passages of the support member and the intermediate-member slot 102 as discussed above.

Figure 11A:
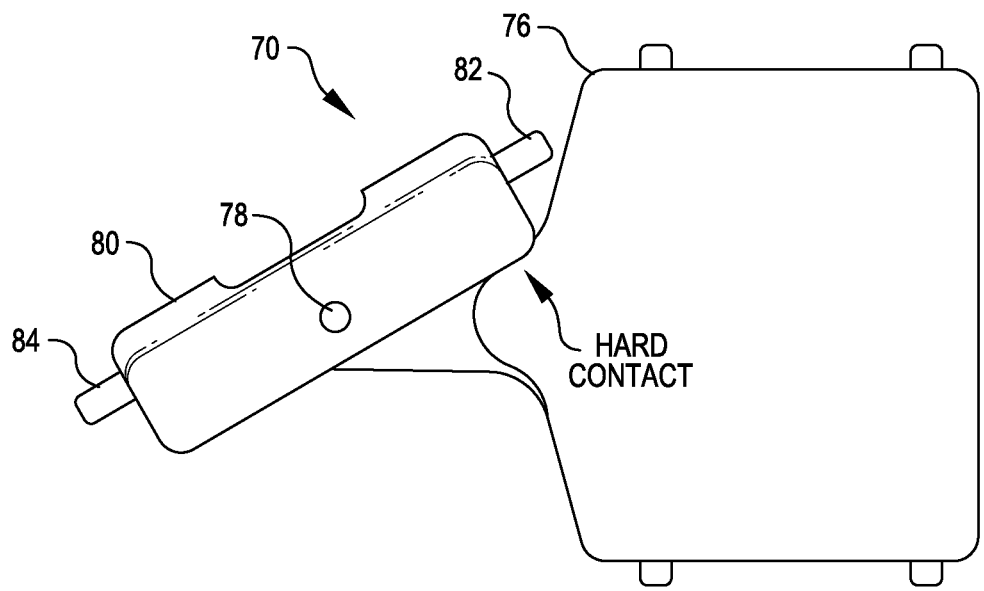
FIG. 11a is a side view illustrating an angular orientation limiting hard contact between the intermediate member and the support member of the two degree-of-freedom wrist of FIGS. 6 and 7, in accordance with many embodiments.
Figure 11B:
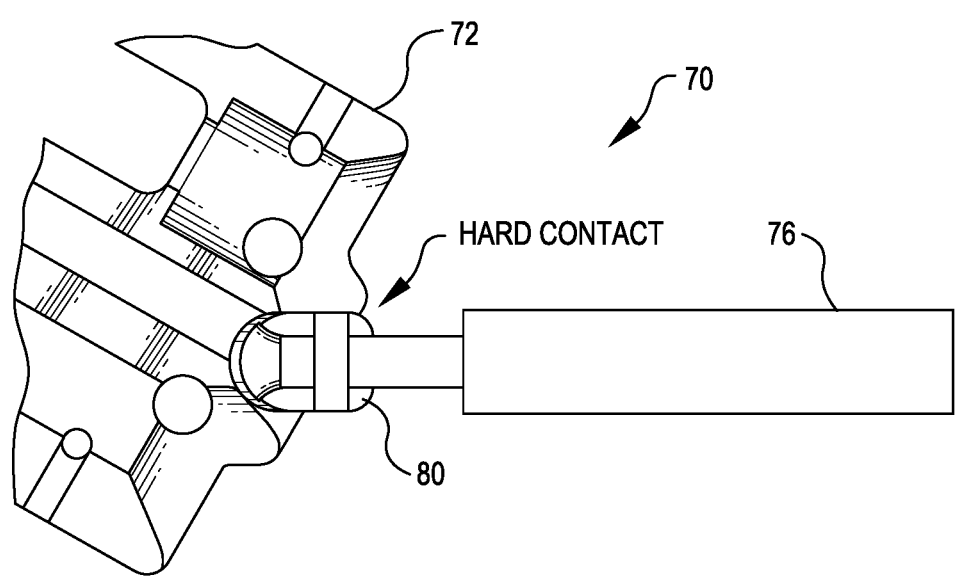
FIG. 11b is a side view illustrating an angular orientation limiting hard contact between the intermediate member of the two degree-of-freedom wrist of FIGS. 6 and 7 and an end-effector body, in accordance with many embodiments.

The two degree-of-freedom wrist 70 includes features that provide angular orientation limiting hard contact for both rotation around the first axis 88 (via the first joint 78) and rotation around the second axis 90 (via the second joint 82 and the third joint 84). Such angular orientation limiting hard contact serves to protect wrist traversing components from damage due to angular over travel. FIG. 11a illustrates an angular orientation limiting hard contact between the intermediate member 80 and the support member 76 of the two degree-of-freedom wrist 70 for rotation about the first axis 88 (via the first joint 78). A similar angular orientation limiting hard contact occurs between the intermediate member 80 and the support member 76 when the intermediate member 80 is rotated in the opposite direction about the first joint 78. FIG. 11*b* illustrates an angular orientation limiting hard contact between the intermediate member 80 of the two degree-of-freedom wrist 70 and the end-effector body 72 for rotation about the second axis 90 (via the second joint 82 and the third joint 84). A similar angular orientation limiting hard contact occurs between the intermediate member 80 and the end-effector body 72 when the end-effector body 72 is rotated in the opposite direction about the second axis 90.

Figure 12:
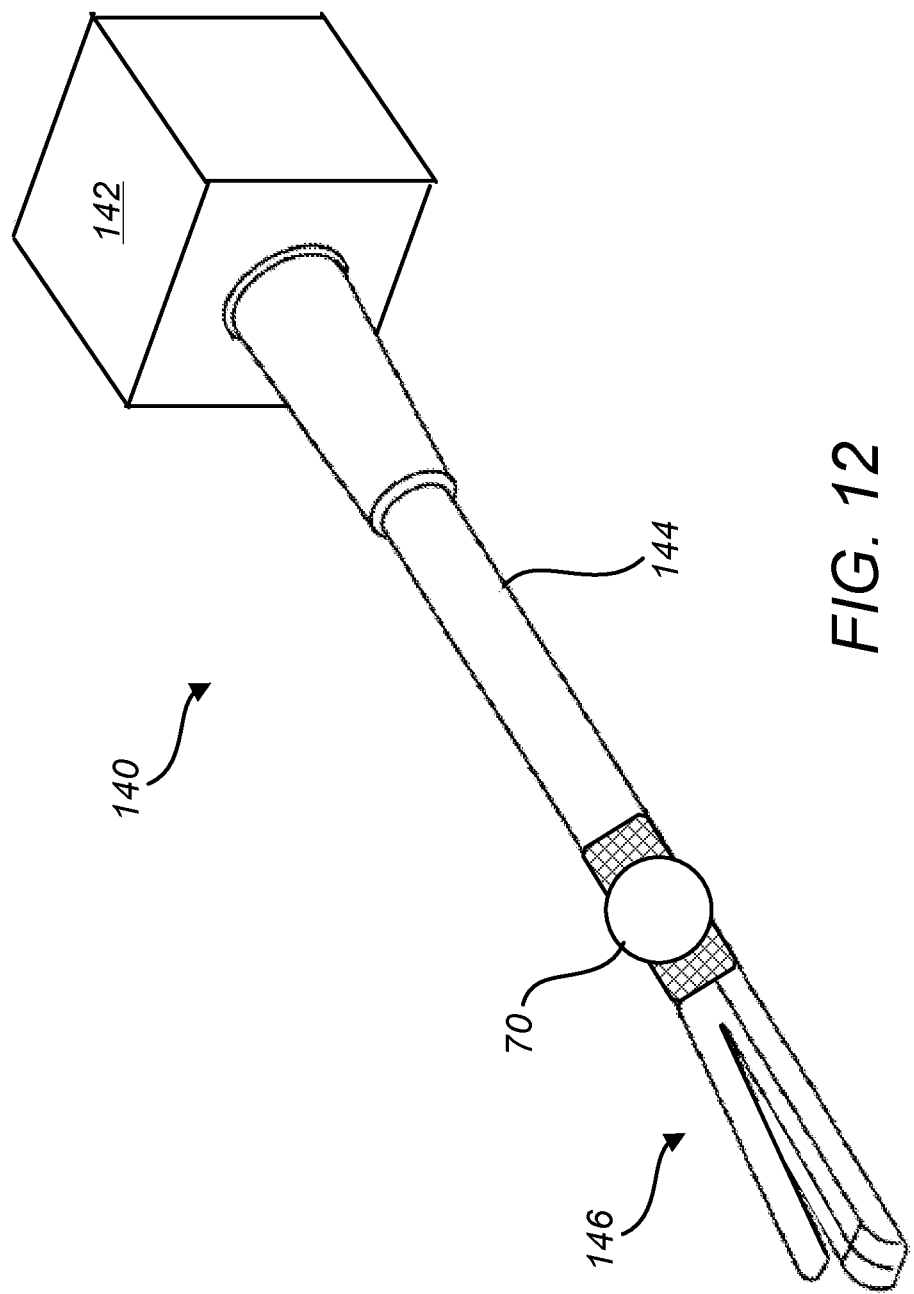
FIG. 12 is a simplified diagrammatic illustration of a surgical assembly, in accordance with many embodiments.

FIG. 12 is a simplified diagrammatic illustration of a tool assembly 140 having the two degree-of-freedom wrist 70, in accordance with many embodiments. The tool assembly 140 includes a proximal actuation assembly 142, a main shaft 144, an articulated end effector base of an end effector 146, and the two degree-of-freedom wrist 70. In many embodiments, the proximal actuation assembly 142 is operatively coupled with the end effector base so as to selectively reorient the end effector base relative to the main shaft 144 in two dimensions, and is operatively coupled with the end effector 146 so as to articulate one or more end effector features relative to the end effector base. A variety of actuation components can be used to couple the actuation assembly 142 with the end effector 146, for example, control cables, cable/hypotube combinations, drive shafts, pull rods, and push rods. In many embodiments, the actuation components are routed between the actuation assembly 142 and the end effector 146 through a bore of the main shaft 144.

The tool assembly 140 can be configured for use in a variety of applications, for example, as a hand-held device with manual and/or automated actuation used in the proximal actuation mechanism 142. As such, the tool assembly 140 can have applications beyond minimally invasive robotic surgery, for example, non-robotic minimally invasive surgery, non-minimally invasive robotic surgery, non-robotic non-minimally invasive surgery, as well as other applications where the use of a two degree-of-freedom wrist would be beneficial.

Wrist Articulation by Linked Tension Members

FIG. 13*a* is a simplified diagrammatic illustration of a surgical tool 170 with wrist articulation by linked tension members, in accordance with many embodiments. The surgical tool 170 includes a second link 172 that is pivotally coupled with a first link 174 via a two degree-of-freedom joint. The joint provides for rotational motion between the second link 172 and the first link 174 about a first axis 176 and a second axis 178. The first axis 176 is fixed relative to the first link 174, and the second axis 178 is fixed relative to the second link 172. Four attachment features 180, 182, 184, 186 are disposed on the second link 172. Each of the attachment features 180, 182, 184, 186 is coupled with a tension member 188, 190, 192, 194, respectively. The tension members 188, 190, 192, 194 are routed through a bore of the first link 174 and are coupled with an actuation mechanism 196 via control cables 198, 200, 202, 204. In many embodiments, the tension members 188, 190, 192, 194 are configured to minimize stretching under operational loading and to reduce cost (e.g., 17 inches long, 0.04-inch outside diameter, 0.02-inch inside diameter; 15.2 inches long, 0.06-inch outside diameter, 0.02-inch inside diameter). In many embodiments, the attachment features 180, 182, 184, 186, the tension members 188, 190, 192, 194, the first axis 176, and the second axis 178 are configured so that opposed axial movement of the tension members angularly orients the second link 172 relative to the first link 174 so as to inhibit changes in tension in the tension members. In the embodiment illustrated, the actuation mechanism 196 includes a first motor driven capstan 206 and a second motor driven capstan 208. A first diagonally opposed pair of control cables (e.g., control cables 198, 202) are wrapped around the first motor driven capstan 206 so that a clockwise rotation of the first motor driven capstan 206 will retract control cable 202 and extend control cable 198 by an equal amount, and a counter-clockwise rotation of the first motor driven capstan 206 will retract control cable 198 and extend control cable 202 by an equal amount. Likewise, a second diagonally opposed pair of control cables (e.g., control cables 200, 204) are wrapped around the second motor driven capstan 208 so that a clockwise rotation of the second motor driven capstan 208 will retract control cable 200 and extend control cable 204 by an equal amount, and a counter-clockwise rotation of the second motor driven capstan 208 will retract control cable 204 and extend control cable 200 by an equal amount.

FIGS. 13*b* and 13*c* diagrammatically illustrates one of the attachment features 180, 182, 184, 186. The attachment features 180, 182, 184, 186 have a curved portion 210 with a fixed center-of-curvature 212 for its curved ordinary centerline 214, and a first radius of curvature 216 about its curved ordinary centerline 214. Each of the fixed center-of-curvatures can be located on a two-dimensional plane containing the second axis 178. The curved ordinary centerlines can lie on two-dimensional planes oriented normal to the second axis 178. The four curved ordinary centerlines can be tangent to a two-dimensional plane containing the first axis 176. Each of the tension members 188, 190, 192, 194 has an attachment lug 218, 220, 222, 224 with hole axis oriented normal to the tension member length. The attachment lug holes are sized to slidingly receive a corresponding attachment feature curved portion. The attachment lugs are configured to rotate about a curved portion and/or slide along a curved portion during articulation of the second link 172 relative to the first link 174.

Figure 13D:
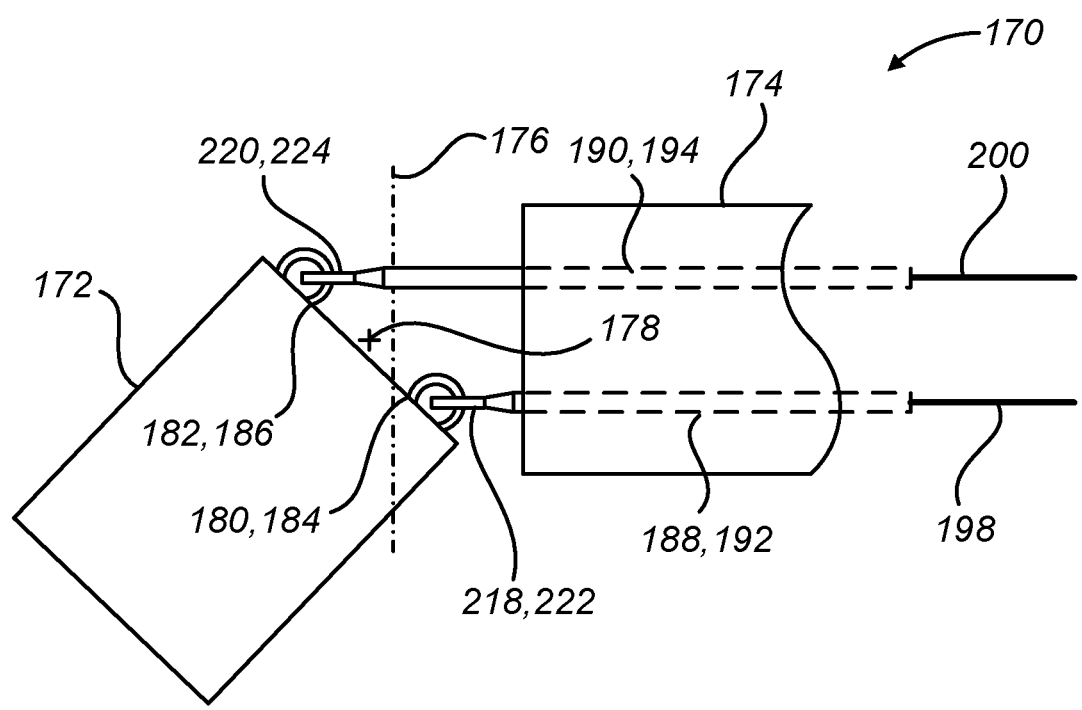
FIG. 13d is a simplified diagrammatic illustration of the surgical tool of FIG. 13a, showing the second link rotated about the second axis, in accordance with many embodiments.

When the second link 172 rotates about the second axis 178, the attachment lugs 218, 220, 222, 224 slide along a corresponding curved portion of the attachment features 180, 182, 184, 186. FIG. 13*d* is a simplified diagrammatic illustration of the surgical tool 170 of FIG. 13*a*, showing the second link 172 rotated about the second axis 178, in accordance with many embodiments. Each of the attachment lugs 218, 220, 222, 224 slides along a corresponding attachment feature curved portion so that each of the tension members is aligned with the fixed center-of-curvature for its corresponding attachment feature curved portion section. As a result, the upper tension members 190, 194 extend by the same amount that the lower tension members 188, 192 retract (as compared to the neutral second link orientation depicted in FIG. 13*a*). With such a balanced extension/retraction of the tension members, one or more pairs of the tension members can be linked and actuated by a common actuation mechanism. For example, diagonally opposed tension members can be coupled with at least one control cable, and the at least one control cable can be actuated by a motor driven capstan. Rotation of the motor driven capstan (e.g., servo controlled) can be used to simultaneously (and equally) extend a section of control cable coupled with a first of the pair of tension members and retract a section of control cable coupled with a second of the pair of tension members. Such simultaneous and equal extension/retraction of control cable can inhibit altering tension in the linked tension members, which may help to avoid any detrimental control cable slack and/or overstressing of tool components.

Figure 13E:
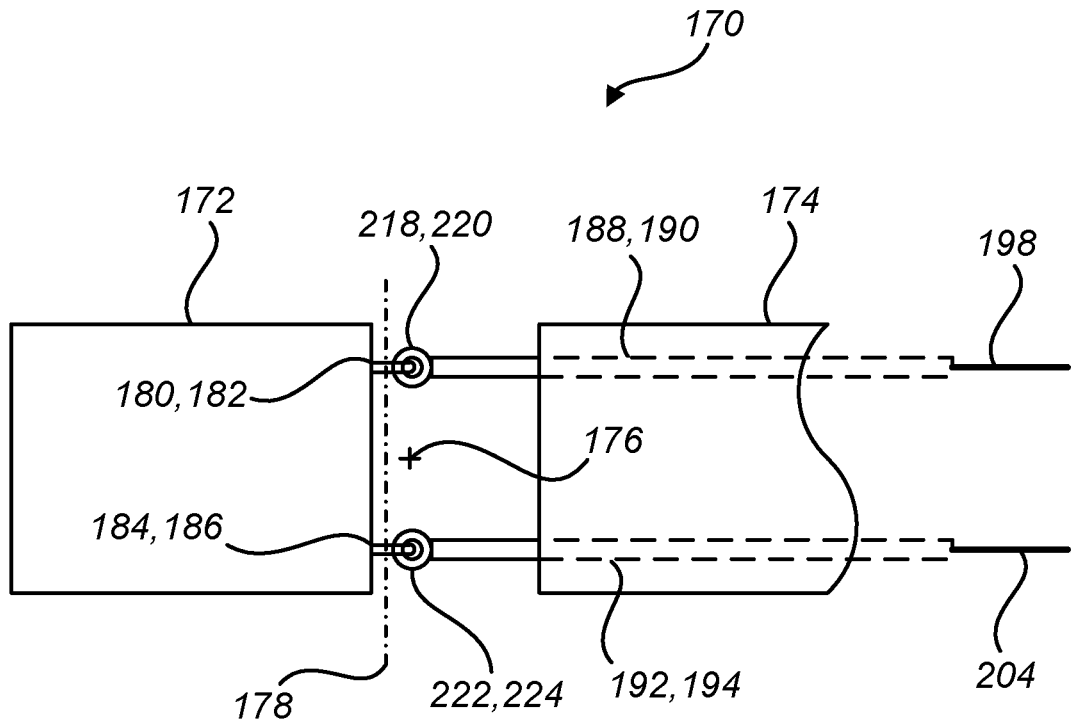
FIG. 13e is a simplified diagrammatic illustration of the surgical tool of FIGS. 13a and 13d, the view direction being parallel with a first axis of the two degree-of-freedom joint, in accordance with many embodiments.

FIG. 13e illustrates the surgical tool 170 of FIGS. 13a and 13d from a view direction parallel with the first axis 176 of the two degree-of-freedom joint, in accordance with many embodiments. As discussed above, the attachment features 180, 182, 184, 186 include curved portion sections having ordinary centerlines and fixed centers-of-curvature. Each of the ordinary centerlines is tangent to a plane containing the first axis 176 of the two degree-of-freedom joint. Each of the fixed centers-of-curvature lies in a plane containing the second axis 178 of the two degree-of-freedom joint.

Figure 13F:
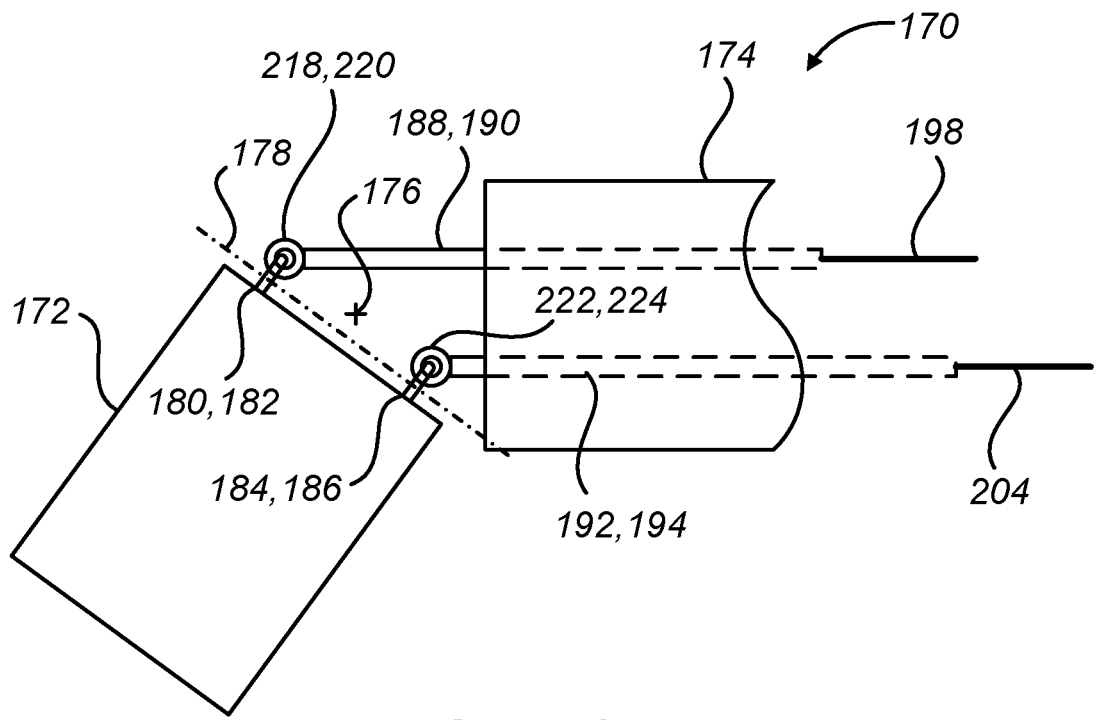
FIG. 13f is a simplified diagrammatic illustration of the surgical tool of FIGS. 13a, 13d, and 13e, showing the second link rotated about the first axis, in accordance with many embodiments.

When the second link 172 rotates about the first axis 176, the attachment lugs 218, 220, 222, 224 rotate about a corresponding attachment feature curved portion ordinary centerline. FIG. 13f is a simplified diagrammatic illustration of the surgical tool 170 of FIGS. 13a, 13d, and 13e, showing the second link 172 rotated about the first axis 176, in accordance with many embodiments. Each of the attachment lugs 218, 220, 222, 224 rotates about a corresponding curved portion ordinary centerline of the attachment features 180, 182, 184, 186 so that each of the tension members is aligned with the corresponding centerline. As a result, the upper tension members 188, 190 extend by the same amount that the lower tension members 192, 194 retract (as compared to the neutral second link orientation depicted in FIG. 13e). As discussed above, with such a balanced extension/retraction of the tension members, one or more pairs of the tension members can be linked and actuated by a common actuation mechanism. For example, a first pair of the four tension members comprising two diagonally opposed tension members 188, 194 can be actuated by a first motor driven capstan, and a second pair of the four tension members comprising the remaining two diagonally opposed tension members 190, 192 can be actuated by a second motor driven capstan. The first and second motor driven capstans can be used to articulate the second link 172 relative to the first link 174 within the range of orientations provided for by the two degree-of-freedom joint.

Figure 13G:
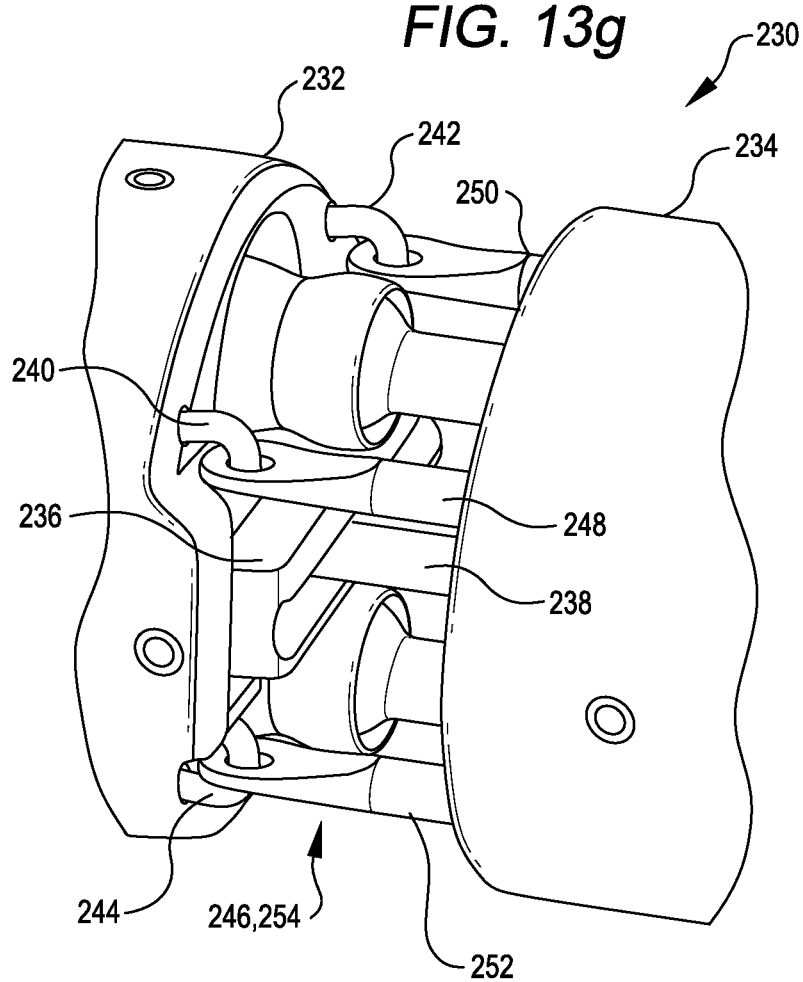
FIG. 13g is a perspective view of a surgical tool having a second link coupled with a first link via a two degree-of-freedom joint, the second link comprising curved portion attachment features that are coupled with linked tension members, in accordance with many embodiments.

FIG. 13g is a perspective partial view of a surgical tool 230 having a second link 232 coupled with a first link 234 via a two degree-of-freedom joint, in accordance with many embodiments. The two degree-of freedom joint illustrated includes an intermediate member 236 that is pivotally coupled to rotate about a first axis relative to a support member 238. The second link 232 is pivotally coupled with the intermediate member 236 so as to rotate about a second axis relative to the intermediate member 236. The second link 232 comprises four attachment features 240, 242, 244, (246 hidden from view), which comprise curved portion sections. Four tension members 248, 250, 252, (254 hidden from view) are coupled with the four attachment features 240, 242, 244, 246.

Figure 13H:
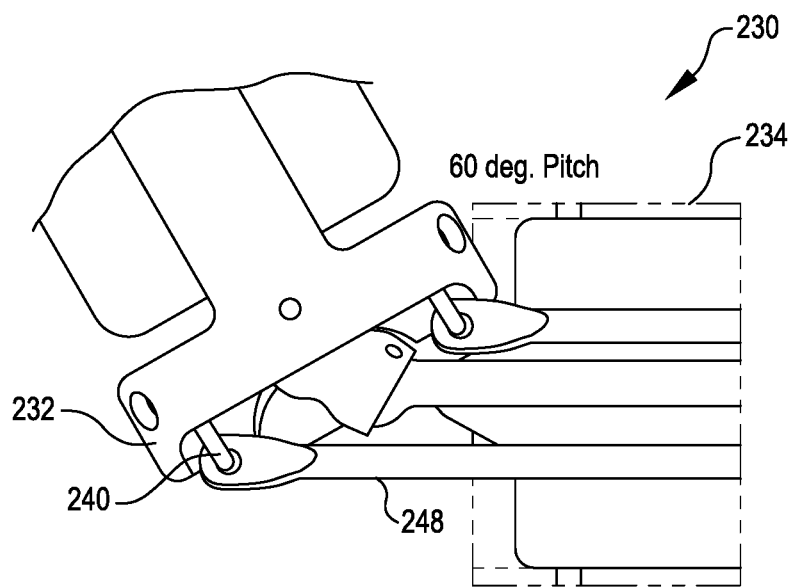
FIG. 13h is a side view of the surgical tool of FIG. 13g, showing a 60 degree orientation of the second link about a first axis of the two degree-of-freedom joint, in accordance with many embodiments.
Figure 13I:
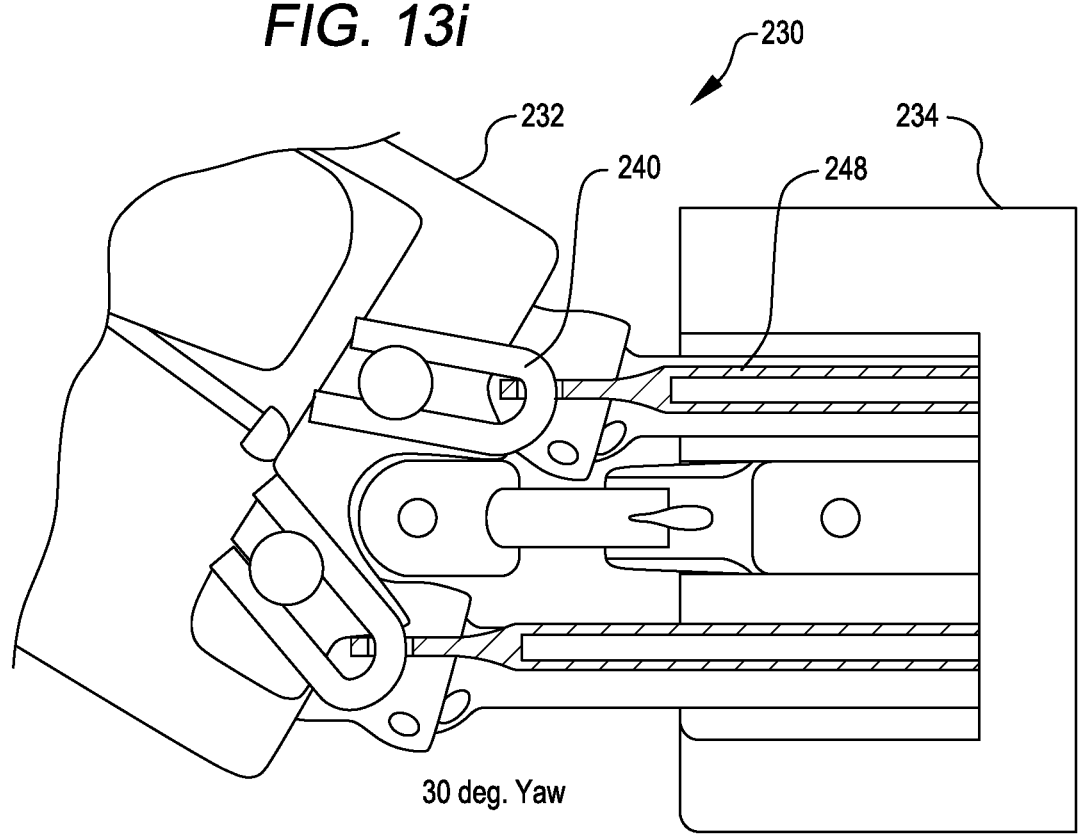
FIG. 13i is a side view of the surgical tool of FIGS. 13g and 13h, showing a 30 degree orientation of the second link about a second axis of the two degree-of-freedom joint, in accordance with many embodiments.

The surgical tool 230 illustrated is configured similar to the surgical tool 170 discussed above and illustrated in FIGS. 13a, 13d, 13e, and 13f. Accordingly, the above discussion regarding the surgical tool 170 applies to the surgical tool 230 illustrated in FIG. 13g, which further illustrates wrist articulation via linked tension members. FIG. 13h is a side view of the surgical tool 230 of FIG. 13g, showing a 60 degree orientation of the second link 232 about the first axis of the two degree-of-freedom joint, in accordance with many embodiments. From the aligned orientation illustrated in FIG. 13g to the orientation illustrated in FIG. 13h, the tension member attachment lugs have pivoted around the ordinary centerlines of the curved portion sections of the attachment features, thereby maintaining the alignment between the tension members and the ordinary centerlines of the curved portion sections. FIG. 13i is a side view of the surgical tool 230 of FIG. 13g, showing a 30 degree orientation of the second link about a second axis of the two degree-of-freedom joint, in accordance with many embodiments. From the aligned orientation illustrated in FIG. 13g to the orientation illustrated in FIG. 13i, the tension member attachment lugs have slid along the curved portion sections of the attachment features, thereby maintaining the alignment between the tension members and the fixed center-of-curvatures for the curved portion sections.

Figure 14A:
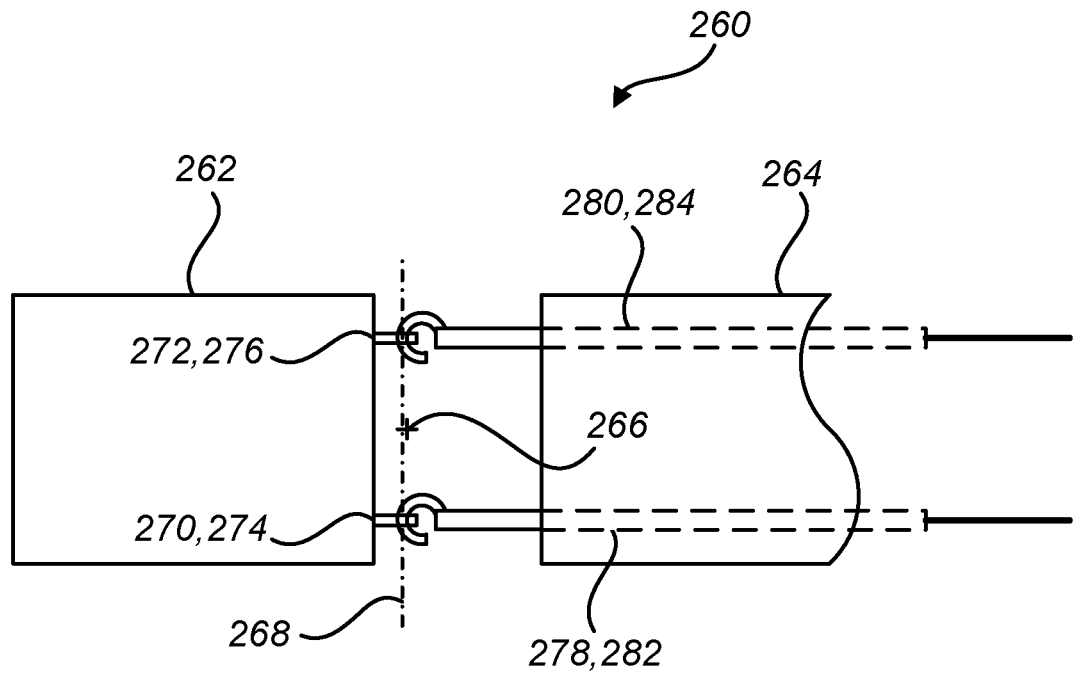
FIG. 14a is a simplified diagrammatic illustration of a surgical tool having a second link coupled with a first link via a two degree-of-freedom joint, the second link comprising attachment lugs that are coupled with linked tension members having curved portion ends, the view direction being parallel with a second axis of the two degree-of-freedom joint, in accordance with many embodiments.

FIG. 14a is a simplified diagrammatic illustration of a surgical tool 260 with wrist articulation by linked tension members, in accordance with many embodiments. A surgical tool 260 includes a second link 262 that is pivotally coupled with a first link 264 via a two degree-of-freedom joint. The joint provides for rotational motion between the second link 262 and the first link 264 about a first axis 266 and a second axis 268. The first axis 266 is fixed relative to the first link 264, and the second axis 268 is fixed relative to the second link 262. Four attachment features 270, 272, 274, 276 are disposed on the second link 262. Each of the attachment features 270, 272, 274, 276 is coupled with a tension member 278, 280, 282, 284, respectively. The tension members 278, 280, 282, 284 are routed through a bore of the first link 264 and are coupled with an actuation mechanism (not shown; e.g., an actuation mechanism associated with actuating a teleoperated surgical instrument in a telerobotic surgical system as described above). In many embodiments, the attachment features 270, 272, 274, 276, the tension members 278, 280, 282, 284, the first axis 266, and the second axis 268 are configured so that opposed axial movement of the tension members angularly orients the second link 262 relative to the first link 264 so as to inhibit changes in tension in the tension members.

Each of the attachment features 270, 272, 274, 276 includes an attachment lug with a hole axis oriented parallel to the second axis 268. Each of the tension members 278, 280, 282, 284 can comprise a section of curved portion having a first radius of curvature about its ordinary centerline and a fixed center-of-curvature for its curved centerline. The curved ordinary centerlines can lie on two-dimensional planes oriented normal to the first axis 266. The attachment feature lug holes are sized to slidingly receive a tension member curved portion. The attachment feature lugs are configured to rotate about a tension member curved portion and/or slide along a tension member curved portion during articulation of the second link 262 relative to the first link 264.

Figure 14B:
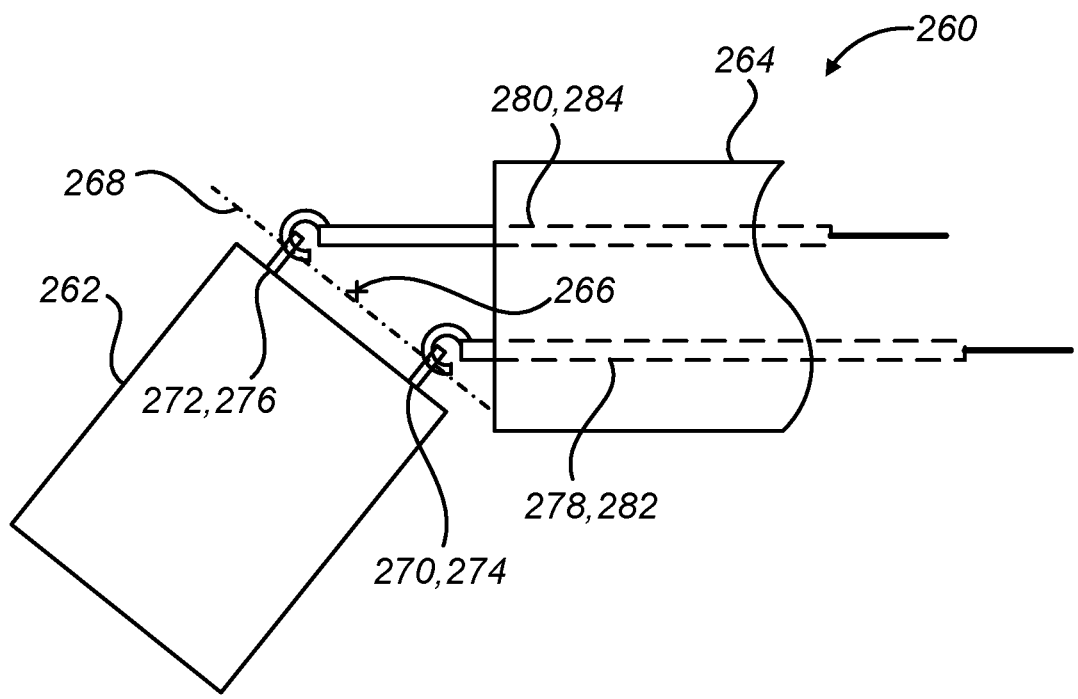
FIG. 14b is a simplified diagrammatic illustration of the surgical tool of FIG. 14a, showing the second link rotated about the second axis, in accordance with many embodiments.

When the second link 262 rotates about the second axis 268, each of the curved portions of the tension members slides against a corresponding attachment feature lug. FIG. 14b is a simplified diagrammatic illustration of the surgical tool 260 of FIG. 14a, showing the second link 262 rotated about the first axis 266, in accordance with many embodiments. Each of the curved portions of the tension members slides against a corresponding attachment feature lug. As a result, the upper tension members 280, 284 extend by the same amount that the lower tension members 278, 282 retract (as compared to the neutral second link orientation depicted in FIG. 14a). This provides a balanced extension/retraction of the tension members, similar to the surgical tool 170 discussed above. Accordingly, additional aspects and benefits of such a balanced extension/retraction of the tension members discussed above with regard to the surgical tool 170 applies to the surgical tool 260, and they will not be repeated here.

Figure 14C:
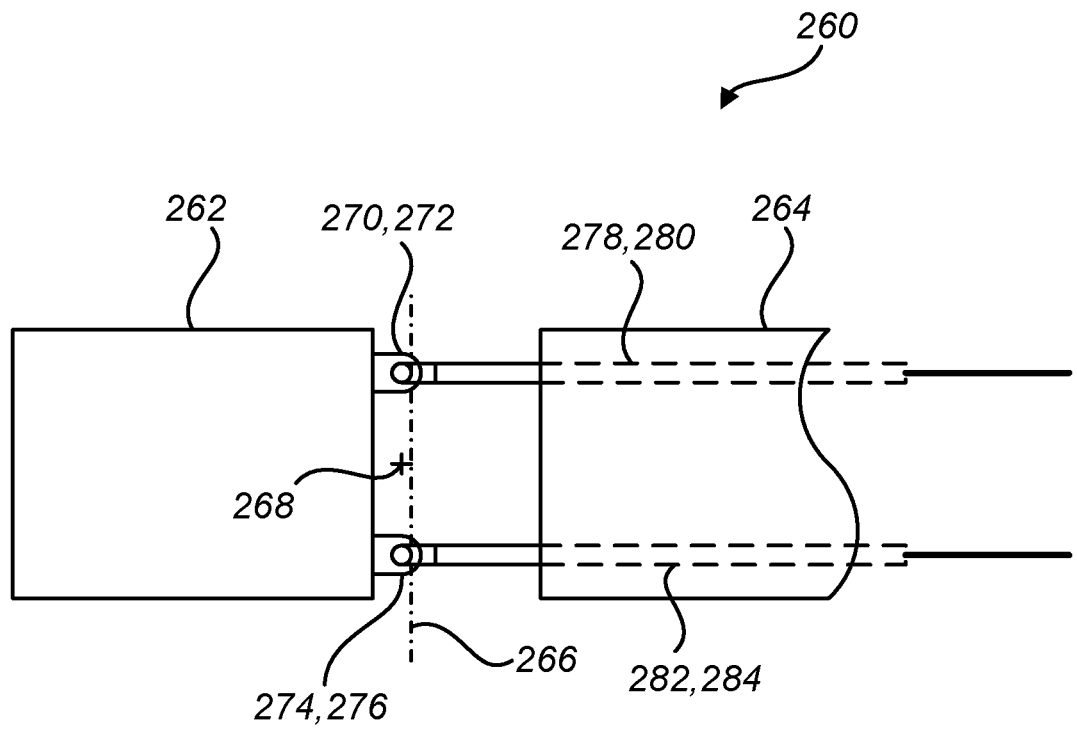
FIG. 14c is a simplified diagrammatic illustration of the surgical tool of FIGS. 14a and 14b, the view direction being parallel with a first axis of the two degree-of-freedom joint, in accordance with many embodiments.

FIG. 14c illustrates the surgical tool 260 of FIGS. 14a and 14b from a view direction parallel with the second axis 268 of the two degree-of-freedom joint, in accordance with many embodiments. As discussed above, each of the attachment features 270, 272, 274, 276 include an attachment lug with a hole axis oriented parallel to the second axis 268. Each of the tension members includes a curved portion section having an ordinary centerline and a fixed center-of-curvature.

Figure 14D:
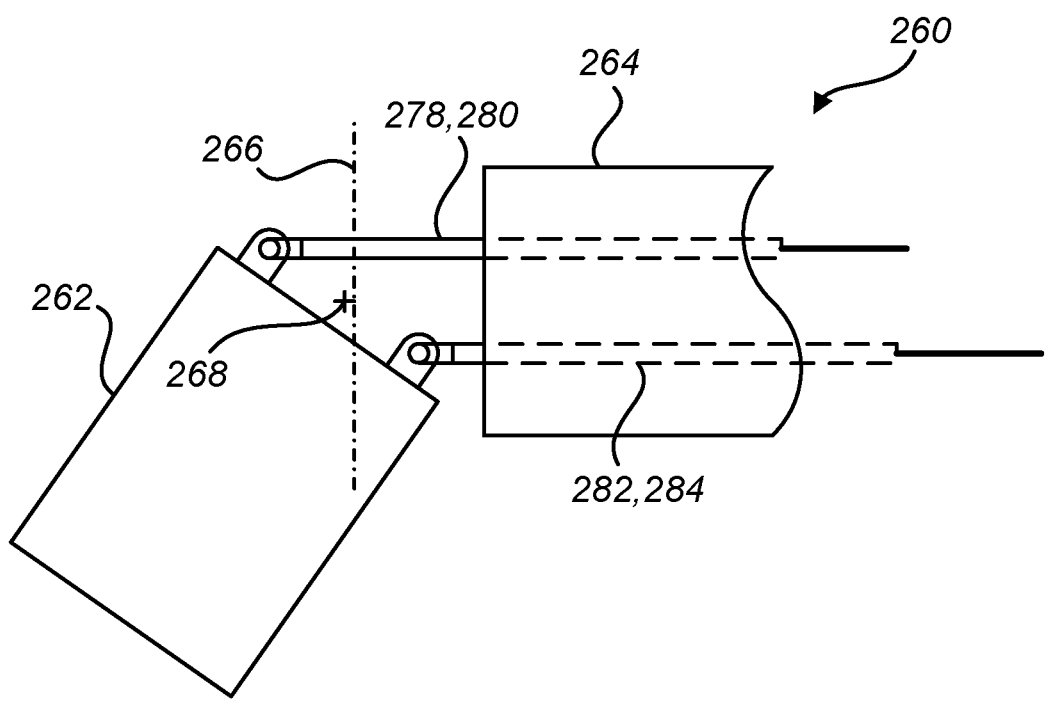
FIG. 14d is a simplified diagrammatic illustration of the surgical tool of FIGS. 14a, 14b, and 14c, showing the second link rotated about the first axis, in accordance with many embodiments.

When the second link 262 rotates about the second axis 268, the tension member curved portions pivot within the attachment feature lugs. FIG. 14d is a simplified diagrammatic illustration of the surgical tool 260 of FIGS. 14a, 14b, and 14c, showing the second link 262 rotated about the second axis 268, in accordance with many embodiments. Each of the tension member curved portions pivots within a corresponding attachment feature lug hole so that each of the tension members remains aligned with the corresponding attachment feature lug hole. As a result, the upper tension members 278, 280 extend by the same amount that the lower tension members 282, 284 retract (as compared to the neutral second link orientation depicted in FIG. 14c). As discussed above, with such a balanced extension/retraction of the tension members, one or more pairs of the tension members can be linked and actuated by a common actuation mechanism. Accordingly, additional aspects and benefits of such a balanced extension/retraction of the tension members discussed above with regard to the surgical tool 170 applies to the surgical tool 260, and will not be repeated here.

FIG. 14e is a partial perspective view of a surgical tool 290 having a second link 292 coupled with a first link (not shown) via a two degree-of-freedom joint, in accordance with many embodiments. The two degree-of freedom joint illustrated includes an intermediate member 294 that is pivotally coupled to rotate about a first axis relative to a support member 296. The second link 292 is pivotally coupled to rotate about a second axis relative to the intermediate member 294. The second link 292 comprises four attachment features 298, 300, 302, (304 hidden from view), each of which comprise an attachment lug. Four tension members 306, 308, 310, 312 are coupled with the four attachment features 298, 300, 302, 304. Each of the four tension members 306, 308, 310, 312 comprises a curved portion section slidingly received by a corresponding attachment feature lug. The surgical tool 290 illustrated is configured similar to the surgical tool 260 discussed above and illustrated in FIGS. 14a, 14b, 14c, and 14d. Accordingly, the above discussion regarding the surgical tool 260 applies to the surgical tool 290 illustrated in FIG. 14e, which further illustrates wrist articulation via linked tension members.

Figure 15:
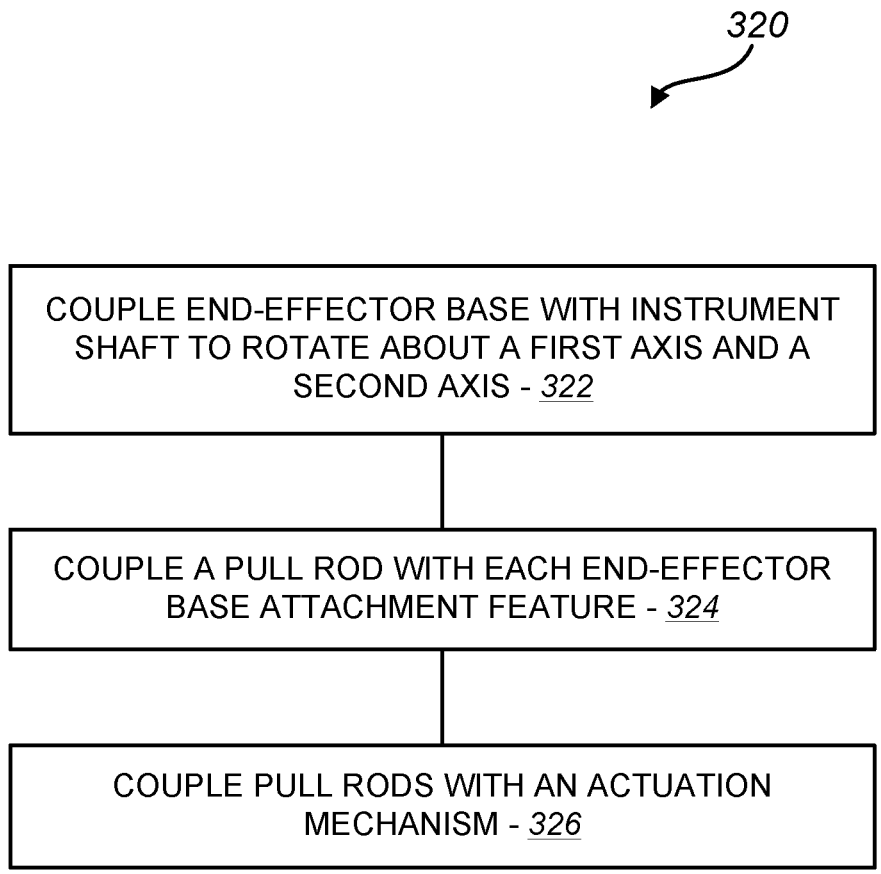
FIG. 15 is a simplified flowchart of a method for manufacturing a surgical tool, in accordance with many embodiments.

FIG. 15 is a simplified flowchart of a method 320 for manufacturing a surgical tool, in accordance with many embodiments. In act 322, a second link is coupled with a first link to rotate about first and second axes. For example, a two degree-of-freedom joint mechanism can be used to couple the second link to the first link. The two degree-of-freedom joint can include an intermediate member that is pivotally coupled with the second link to rotate relative to the first link about a first axis. The second link can be pivotally coupled with the intermediate member to rotate relative to the intermediate member about a second axis. The first link can have a distal end, a proximal end, and a first link axis defined there between. The first link can have an axial bore. The first and second axes can be nonparallel to the first link axis. The first axis can be nonparallel to the second axis. The second link can comprise four attachment features. Each of the attachment features can be offset from the first and second axes when viewed along the first link axis. One of the attachment features can be disposed in each quadrant defined by the first and second axes when viewed along the first link axes.

In act 324, a tension member is coupled with each of the second link attachment features. Each of the tension members can extend distally from within the bore of the first link to one of the attachment features of the second link so that axial movement of the tension members angularly orients the second link relative to the first link about the axes. Interface surfaces between the tension members and the attachment features can vary a position of the tension members relative to the second link in correlation with the angular orientation of the second link relative to the first link so as to inhibit changes in tension of the tension members.

In act 326, each of the tension members is coupled with an actuation mechanism operable to control the angular orientation of the second link relative to the first link in two dimensions by actuating the tension members. For example, a first of the four tension members can be coupled with a first control cable, and a second of the tension members can be coupled with a second control cable. The first and the second tension members can be diagonally opposed tension members. The first and second control cables can be coupled with a first capstan of the actuation mechanism. A third of the four tension members can be coupled with a third control cable, and a fourth of the tension members can be coupled with a fourth control cable. The third and the fourth tension members can be diagonally opposed tension members. The third and fourth control cables can be coupled with a second capstan of the actuation mechanism.

Figure 16:
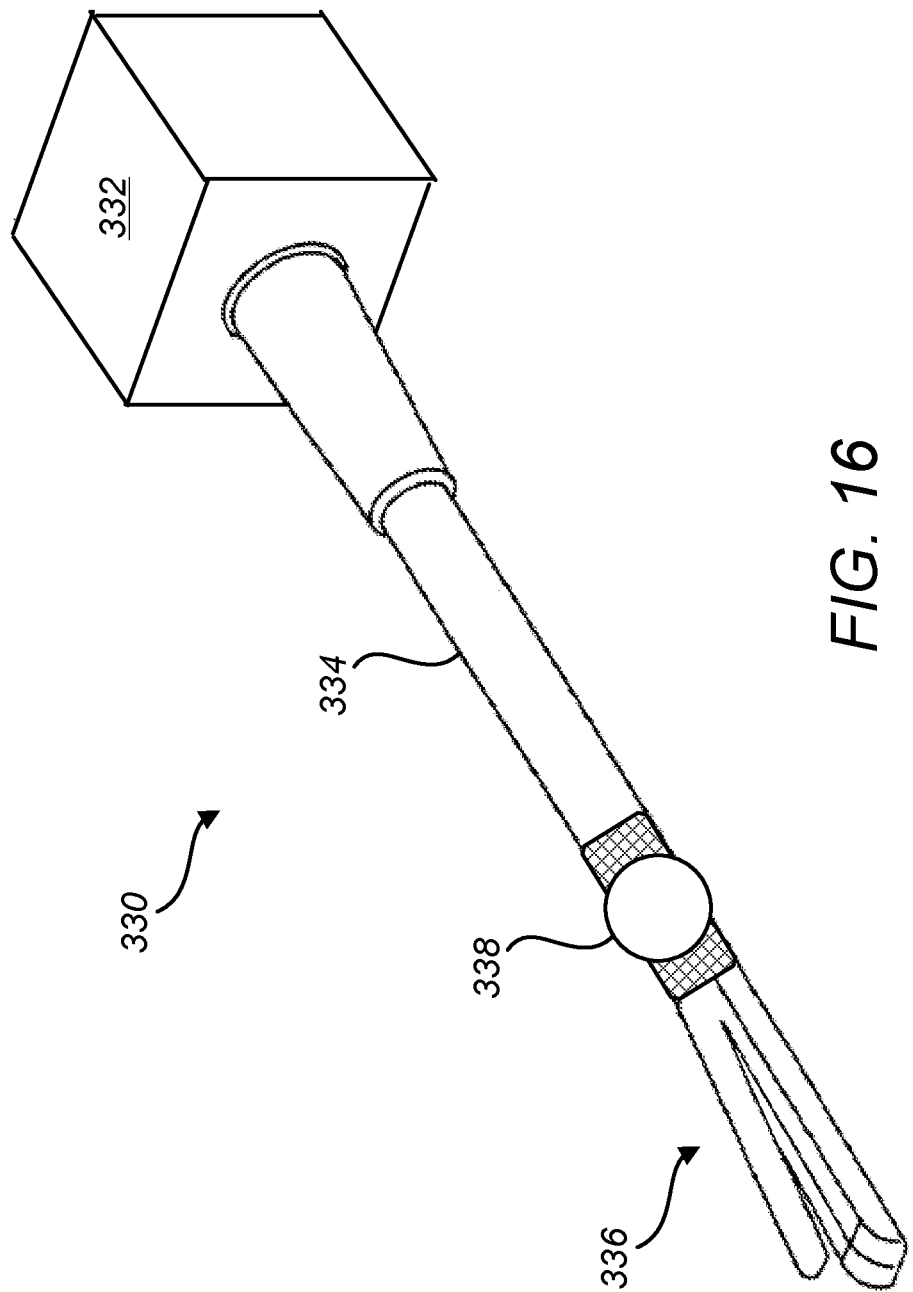
FIG. 16 is a simplified diagrammatic illustration of a surgical assembly, in accordance with many embodiments.

FIG. 16 is a simplified diagrammatic illustration of a tool assembly 330 having a wrist articulated by linked tension members, in accordance with many embodiments. The tool assembly 330 includes a proximal actuation assembly 332, a main shaft 334, an articulated end effector base of an end effector 336, and a two degree-of-freedom wrist 338. In many embodiments, the proximal actuation assembly 332 is operatively coupled with the end effector base so as to selectively reorient the end effector base relative to the main shaft 334 in two dimensions via linked tension members as described above with regard to the surgical tools 170, 260, and is operatively coupled with the end effector 336 so as to articulate one or more end effector features relative to the end effector base. A variety of actuation components can be used to couple the actuation assembly 332 with the end effector 336, for example, control cables, drive shafts, and the above described linked tension members and corresponding end effector base attachment features. In many embodiments, the actuation components are routed between the actuation assembly 332 and the end effector 336 through a bore of the main shaft 334.

The tool assembly 330 can be configured for use in a variety of applications, for example, as a hand held device with manual and/or automated actuation used in the proximal actuation mechanism 332. As such, the tool assembly 330 can have applications beyond minimally invasive robotic surgery, for example, non-robotic minimally invasive surgery, non-minimally invasive robotic surgery, non-robotic non-minimally invasive surgery, as well as other applications where the use of a two degree-of-freedom joint articulated by linked tension members would be beneficial.

Mechanisms for Transmitting Torque Through an Angle

FIG. 17 is a simplified diagrammatic illustration of a tool assembly 370 having a mechanism 372 for transmitting torque through an angle, in accordance with many embodiments. The tool assembly 370 includes a proximal torque source 374, a main shaft 376, an articulated end effector base of an end effector 378, and the torque transmitting mechanism 372. The torque transmitting mechanism 372 includes a drive shaft 380, a driven shaft 382, and a coupling member 384 coupled with both the drive shaft 380 and the driven shaft 382 such that a rotation of the drive shaft 380 produces a corresponding rotation of the driven shaft 382. In many embodiments, the drive shaft 380 is mounted for rotation relative to the main shaft 376 and is routed through a bore (centerline or offset) of the main shaft 376. In many embodiments, the torque transmitting mechanism 372 is configured so that the speed of rotation of the driven shaft 382 substantially matches the speed of rotation of the drive shaft 380 at any relative angular orientation between the shafts. In operation, the proximal torque source 374 rotates the drive shaft 380, which rotates the coupling member 384, which rotates the driven shaft 382, thereby transmitting torque through an angle between the main shaft 376 and the end effector 378. In many embodiments, the driven shaft 382 actuates a shaft driven mechanism of the end effector 378. For example, an end effector shaft driven mechanism can articulate a clamping jaw relative to the articulated end effector base and/or can actuate a surgical device (e.g., a stapling device, a cutter device, a cautery device). Such shaft driven mechanisms are merely exemplary. The driven shaft can be used to actuate other suitable shaft driven mechanisms. Additionally, while the tool assembly 370 is shown with one torque transmitting mechanism 372, this is merely exemplary. One or more torque transmitting mechanisms 372 can be used, for example, to transfer torque from the proximal torque source 374 to a corresponding one or more end effector mechanisms.

The tool assembly 370 can be configured for use in a variety of applications, for example, as a hand held device with manual and/or automated actuation used in the proximal torque source 374. As such, the tool assembly 370 can have applications beyond minimally invasive robotic surgery, for example, non-robotic minimally invasive surgery, non-minimally invasive robotic surgery, non-robotic non-minimally invasive surgery, as well as other applications where the use of the disclosed mechanisms for transmitting torque through an angle would be beneficial.

FIG. 18 is a side view of a mechanism 390 for transmitting torque through an angle, in accordance with many embodiments. The torque transmitting mechanism 390 includes a drive shaft 392, a coupling member 394, a driven shaft 396, a first coupling pin 398, and a second coupling pin 400. FIG. 18 illustrates the torque transmitting mechanism 390 in an inline configuration.

The drive shaft 392 is axially and rotationally coupled with the coupling member 394. The drive shaft 392 has a distal end 402 that is received within a first receptacle 404 of the coupling member 394. The drive shaft distal end 402 comprises a transverse slot 406. The first coupling pin 398 mates with the coupling member 394 so as to cross the first receptacle 404. The first coupling pin 398 is received by the drive shaft transverse slot 406. The drive shaft distal end 402 and the coupling member first receptacle 404 can have a complementary shaped interfacing surface(s), for example, a spherical surface(s). Interaction between the first coupling pin 398 and the drive shaft transverse slot 404 axially and rotationally couples the drive shaft 392 and the coupling member 394. Additionally, interaction between interfacing surfaces of the drive shaft distal end 402 and the coupling member first receptacle 404 can further restrain the drive shaft 392 relative to the coupling member 394.

Similarly, the driven shaft 396 is axially and rotationally coupled with the coupling member 394. The driven shaft 396 has a proximal end 408 that is received within a second receptacle 410 of the coupling member 394. The driven shaft proximal end 408 comprises a transverse slot 412. The second coupling pin 400 mates with the coupling member 394 so as to cross the second receptacle 410. The second coupling pin 400 is received by the driven shaft transverse slot 412. The driven shaft proximal end 408 and the coupling member second receptacle 410 can have a complementary shaped interfacing surface(s), for example, a spherical surface(s). Interaction between the second coupling pin 400 and the driven shaft transverse slot 412 axially and rotationally couples the driven shaft 396 and the coupling member 394. Additionally, interaction between interfacing surfaces of the driven shaft proximal end 408 and the coupling member second receptacle 410 can further restrain the driven shaft 396 relative to the coupling member 394.

Figure 19A:
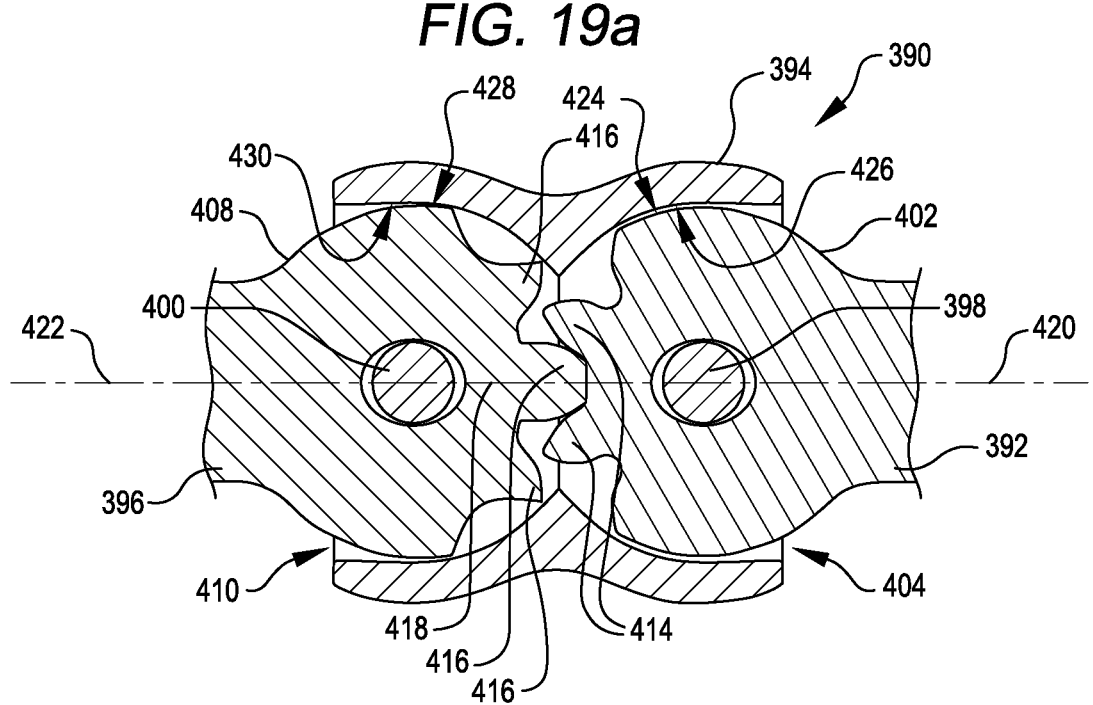
FIG. 19a is a cross-sectional view of the mechanism of FIG. 18, illustrating engagement between meshing spherical gear teeth of the drive shaft and the driven shaft for the inline configuration, in accordance with many embodiments.

FIG. 19a is a cross-sectional view of the torque transmitting mechanism 390 of FIG. 18, illustrating engagement between spherical gear teeth 414 of the drive shaft 392 and mating spherical gear teeth 416 of the driven shaft 396, in accordance with many embodiments. The gear teeth are termed "spherical" because they are in the general form of geometric small circles on a sphere's surface. The cross section illustrated includes the centerlines of the drive shaft 392, the driven shaft 396, and the coupling member 394, respectively, and is taken along a view direction parallel to the first coupling pin 398 and the second coupling pin 400. In the inline configuration illustrated, the coupling member 394, the drive shaft 392, and the driven shaft 396 are aligned. The coupling member 394 rotates about a coupling member axis 418. The coupling member axis 418 is a longitudinal centerline between the two receptacles 404, 410. The drive shaft 392 rotates about a drive axis 420. The driven shaft 396 rotates about a driven axis 422. The drive shaft 392 is constrained to pivot about the first coupling pin 398 (and thereby is constrained to pivot relative to the coupling member 394). Likewise, the driven shaft 396 is constrained to pivot about the second coupling pin 400 (and thereby is constrained to pivot relative to the coupling member 394). The additional constraint between the drive shaft 392 and the driven shaft 396 provided by the engagement between the drive shaft gear teeth 414 and the driven shaft gear teeth 416 ties the relative angular orientation between the drive shaft 392 and the coupling member 394 to the relative angular orientation between the driven shaft 396 and the coupling member 394.

FIG. 19a also illustrates a drive shaft outer spherical surface 424 that interfaces with an inner spherical surface 426 of the coupling member first receptacle 404. Similarly, a driven shaft outer spherical surface 428 interfaces with an inner spherical surface 430 of the coupling member second receptacle 410. As discussed above, the constraint provided by the first coupling pin 398 axially and rotationally couples the drive shaft 392 and the coupling member 394, and the constraint provided by the second coupling pin 400 axially and rotationally couples the driven shaft 396 and the coupling member 394. Additionally, the constraint provided by the interfacing spherical surfaces can further constrain the drive shaft 392 and the driven shaft 396 relative to the coupling member 394.

Figure 19B:
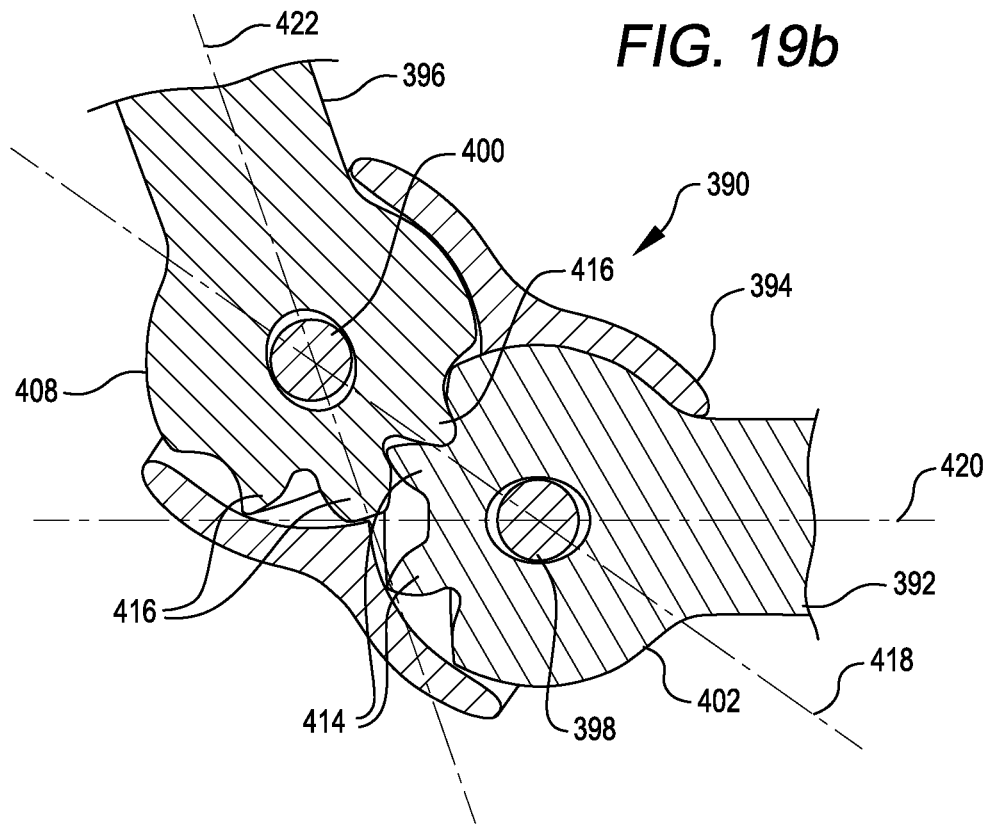
FIG. 19b is a cross-sectional view of the mechanism of FIGS. 18 and 19a, illustrating engagement between the meshing spherical gear teeth of the drive shaft and the driven shaft for an angled configuration, in accordance with many embodiments.

FIG. 19b is a cross-sectional view of the torque transmitting mechanism 390 of FIGS. 18 and 19a, illustrating engagement between the drive shaft gear teeth 414 and the driven shaft gear teeth 416 for an angled configuration, in accordance with many embodiments. The cross section illustrated includes the drive axis 420, the driven axis 422, and the coupling member axis 418, and is taken along a view direction parallel to the first coupling pin 398 and the second coupling pin 400.

In the angled configuration illustrated, the driven axis 422 deviates from the drive axis 420 by 70 degrees. The constraint provided by engagement between the drive shaft gear teeth 414 and the driven shaft gear teeth 416 results in the 70 degrees being equally distributed amongst a 35 degree deviation between the drive axis 420 and the coupling axis 418, and a 35 degree deviation between the coupling axis 418 and the driven axis 422. By constraining the coupling member to be oriented at an equivalent relative angle to both the drive shaft and the driven shaft, any rotational speed differences between the drive shaft and the coupling member are effectively canceled when the rotation of the coupling member is transferred to the driven shaft, thereby substantially eliminating any rotational speed differences between the drive shaft and the driven shaft.

The drive shaft gear teeth 414 and the driven shaft gear teeth 416 are spherically oriented so as to provide the above described constraint between the drive shaft 392 and the driven shaft 396 for any angular orientation of the torque transmitting mechanism 390. For an angled configuration, rotation of the drive shaft 392 and a corresponding rotation of the driven shaft 396 causes different portions of the drive shaft distal end 402 and the driven shaft proximal end 408 to be intersected by the coupling axis 418. The use of spherical gear teeth allows this movement of the shafts while still providing the angular constraint necessary to orient the coupling member relative to the drive shafts.

Figure 19C:
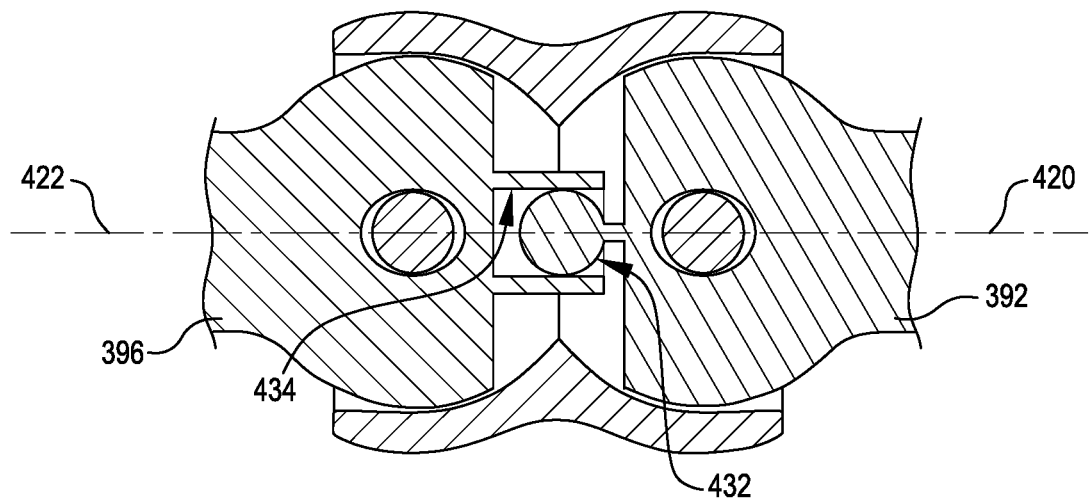
FIG. 19c illustrates an alternate shaft angle constraint configuration, in accordance with many embodiments.

Other suitable shaft angle constraint configurations can also be used. For example, as illustrated in FIG. 19c, a drive shaft feature (e.g., a feature comprising a spherical surface 432 cantilevered from the drive shaft distal end) can engage with a driven shaft feature (e.g., a feature comprising a cylindrical bore 434 receiving the cantilevered drive shaft feature comprising a spherical surface cantilevered from the driven shaft proximal end). While the use of some shaft angle constraints may result in some level of variation between a relative angle between the drive axis 420 and the coupling axis 418, and a relative angle between the coupling axis 418 and the driven axis 422, the resulting rotational speed variations between the drive shaft 392 and the driven shaft 396 may be acceptable in some applications.

Other spherical gear tooth profiles can be used to provide a suitable shaft angle constraint. For example, the drive shaft distal end 402 can comprise a gear tooth surface that extends around the drive axis 420 and the driven shaft proximal end 408 can comprise a complementary gear tooth surface that extends around the driven axis 422 so that the drive shaft gear tooth surface engages the driven shaft gear tooth surface so as to provide the shaft angle constraint. The drive shaft gear tooth surface can be defined by a drive shaft gear tooth profile extending radially from the drive axis 420 and the driven shaft gear tooth surface can be defined by a driven shaft gear tooth profile extending radially from the driven axis 422 so as to provide a shaft angle constraint that maintains substantial equivalence between the drive/coupler angle and the driven/coupler angle. The drive shaft gear tooth surface can comprise a revolute surface defined by rotating the drive shaft gear tooth profile about the drive axis 420 and the driven shaft gear tooth surface can comprise a revolute surface defined by rotating the driven shaft gear tooth profile about the driven axis 422. For example, in FIG. 19c, the cantilevered spherical surface 432 includes a gear tooth profile (its circular cross section) that extends radially from the drive axis and a revolute surface defined by rotating its gear tooth profile about the drive axis 420. The cylindrical bore surface 434 includes a complementary gear tooth surface (its straight line cross section) that extends radially from the driven axis 422 and a revolute surface defined by rotating its gear tooth profile about the drive axis 422. Other gear tooth profiles can be configured in a like fashion, for example, gear tooth profiles intermediate in shape between the gear tooth profile illustrated in FIG. 19a and the gear tooth profile illustrated in FIG. 19c.

Figure 19D:
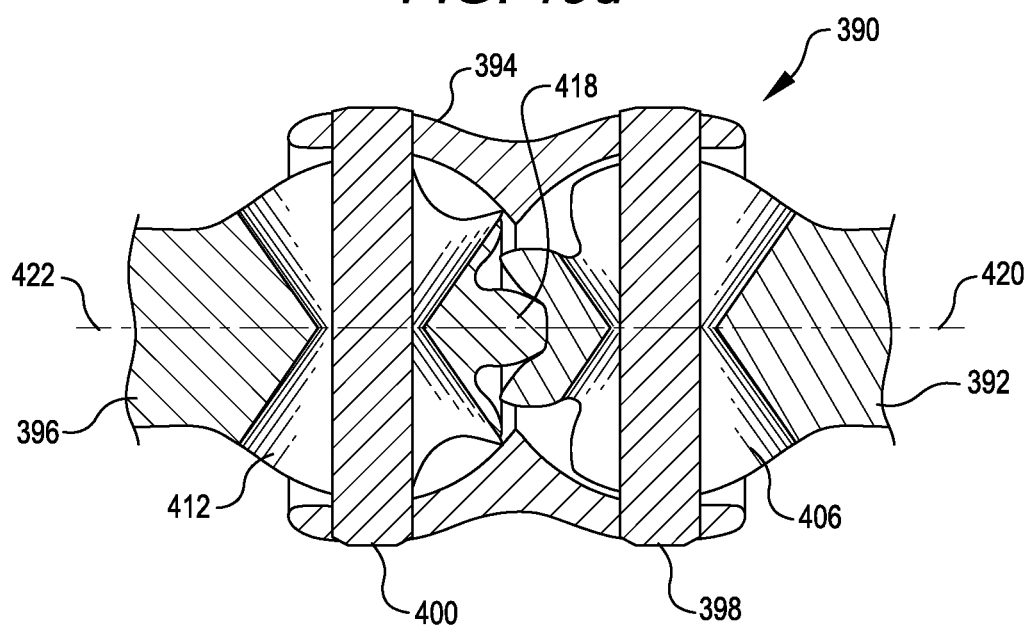
FIG. 19d is a cross-sectional view of the mechanism of FIGS. 18, 19a, and 19b, illustrating the configuration of pin receiving transverse slots in the drive shaft and the driven shaft, in accordance with many embodiments.

FIG. 19d is a cross-sectional view of the torque transmitting mechanism 390 of FIGS. 18, 19a, and 19b, illustrating the configuration of the drive shaft transverse slot 406 and the similar driven shaft transverse slot 412, in accordance with many embodiments. The drive shaft transverse slot 406 is configured to accommodate the first coupling pin 398 throughout a range of angles between the drive axis 420 and the coupling axis 418. Likewise, the driven shaft transverse slot 412 is configured to accommodate the second coupling pin 400 throughout a range of angles between the driven axis 422 and the coupling axis 418. When the torque transmitting mechanism 390 is operated in an angled configuration, the position of the first coupling pin 398 within the drive shaft transverse slot 406 will undergo a single oscillation cycle for each 360 degree rotation of the drive shaft 392. Likewise, the position of the second coupling pin 400 within the driven shaft transverse slot 412 will undergo a single oscillation cycle for each 360 degree rotation of the driven shaft 396.

Figure 20:
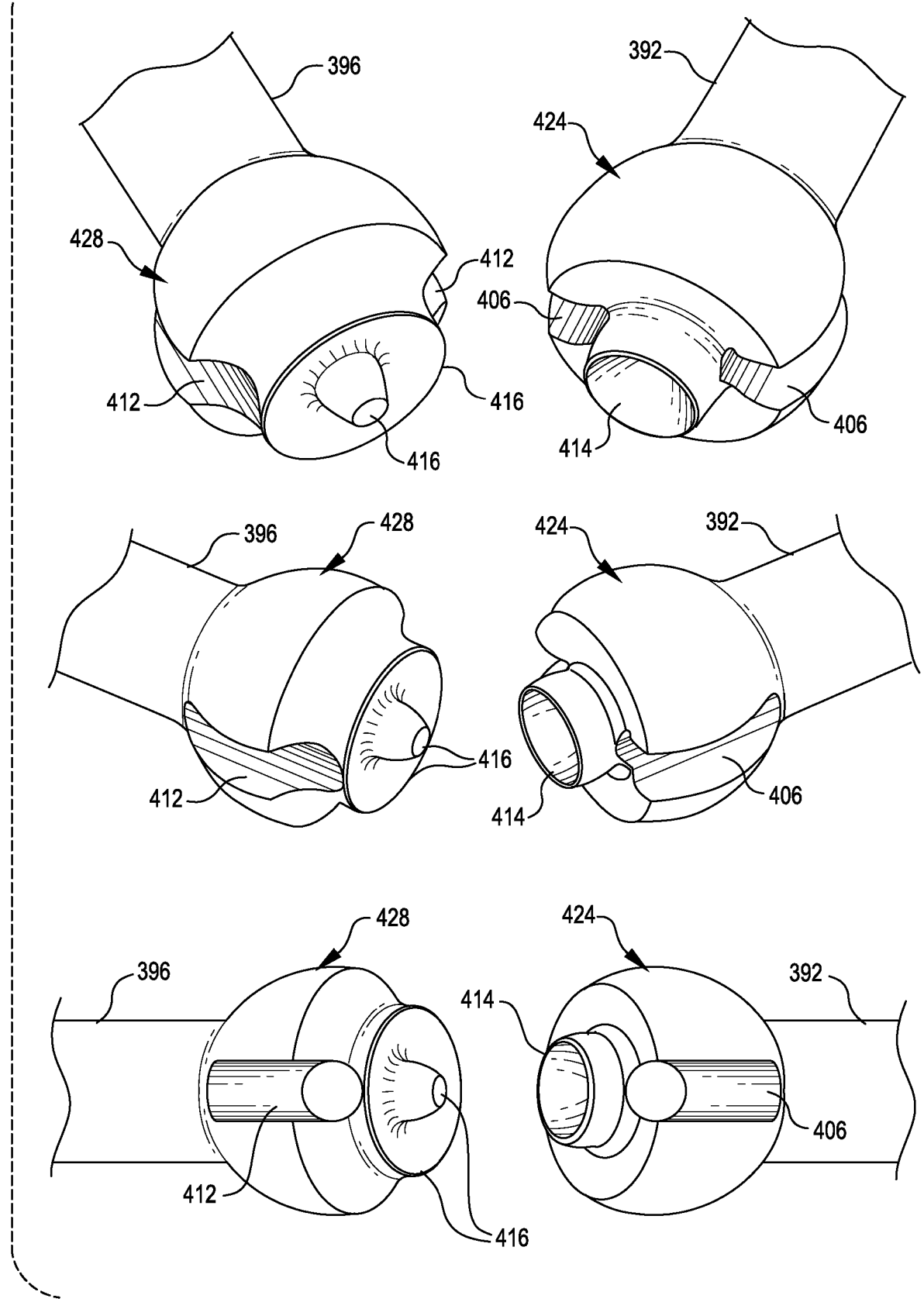
FIG. 20 is an assortment of perspective views of the drive and driven shafts of FIGS. 18, 19a, 19b, and 19d.

FIG. 20 presents an assortment of perspective views of the drive shaft 392 and the driven shaft 396. These perspective views show details of the drive and driven shafts from different viewing directions, for example, the spherical gear teeth 414 of the drive shaft 392, the spherical gear teeth 416 of the driven shaft 396, the drive shaft transverse slot 406, the driven shaft transverse slot 412, the drive shaft outer spherical surface 424, and the driven shaft outer spherical surface 428.

Figure 21A:
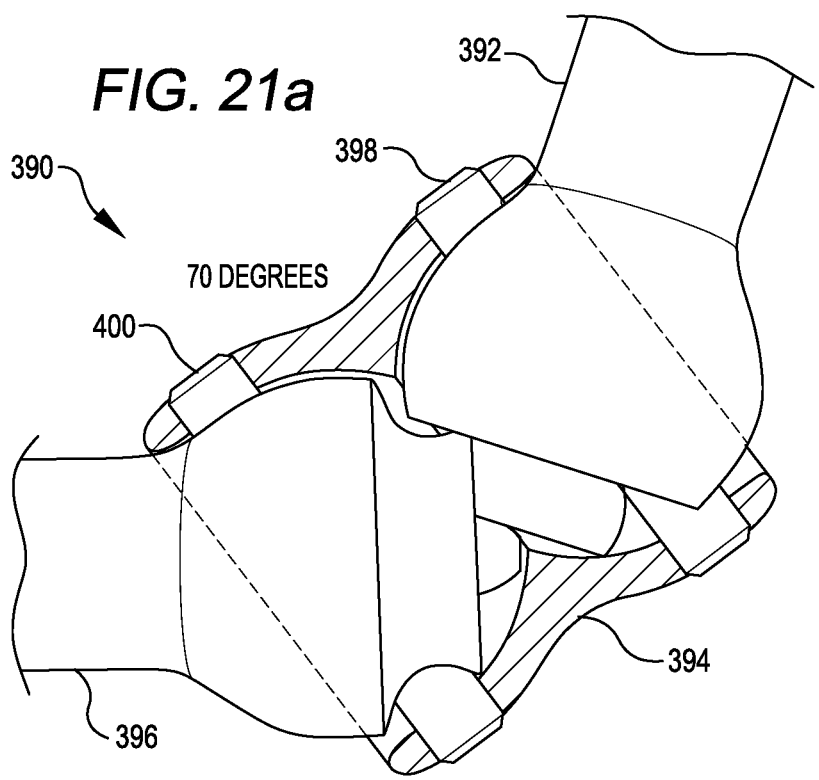
FIG. 21a is a side view of the mechanism of FIGS. 18, 19a, 19b, and 19c along a view direction normal to the coupling pins, in accordance with many embodiments.
Figure 21B:
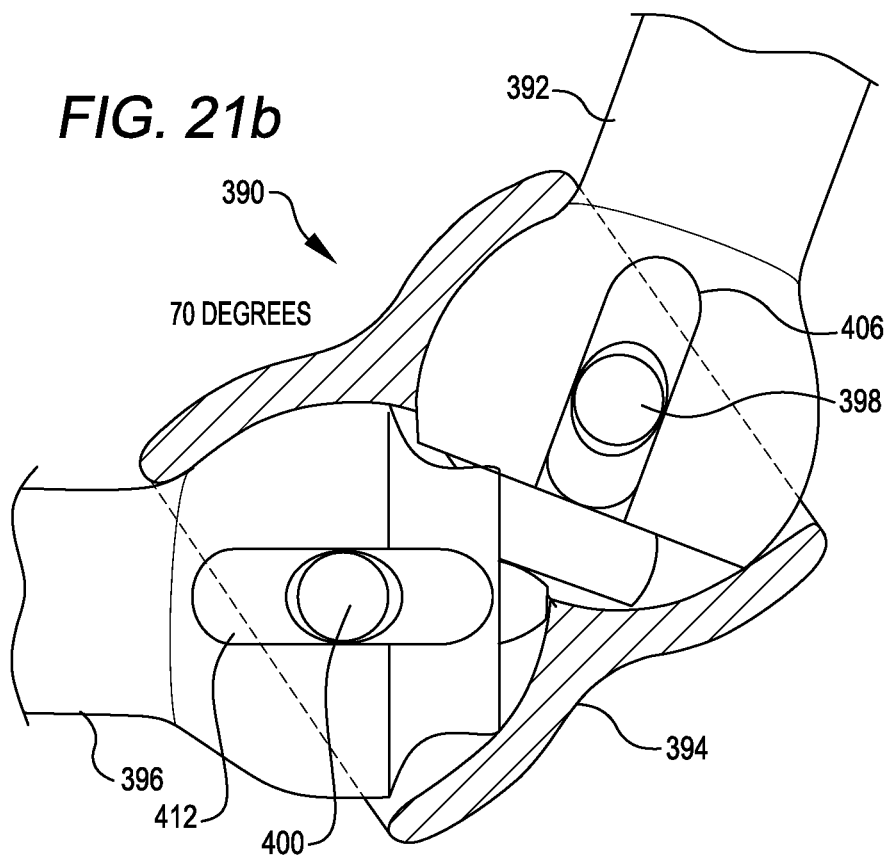
FIG. 21b is a side view of the mechanism of FIGS. 18, 19a, 19b, 19c, and 21a along a view direction parallel to the coupling pins, in accordance with many embodiments.

The oscillation of the coupling pins 398, 400 within the transverse slots 406, 412 can be described with reference to FIGS. 21a and 21b. FIG. 21a is a view of the torque transmitting mechanism 390 along a view direction normal to the coupling pins 398, 400. FIG. 21b is a view of the torque transmitting mechanism 390 along a view direction parallel to the coupling pins 398, 400. In FIGS. 21a and 21b, the coupling member 394 is transparent to illustrate interactions between mechanism components. In the position shown in FIG. 21a, to accommodate the angle between the drive shaft 392 and the coupling member 394, the first coupling pin 398 is canted within the drive shaft transverse slot (this can be visualized by considering the slot shape illustrated in FIG. 19d in conjunction with the shaft angles illustrated in FIG. 21a). In FIG. 21b, the coupling member 394 has an angular orientation that is 90 degrees from the coupling member orientation of FIG. 21a, thereby aligning the coupling pins 398, 400 with the view direction. For the orientation shown in FIG. 21b, the coupling pins 398, 400 are not canted within the transverse slots 406, 412 (similar to FIG. 19d). During a 360 degree revolution of the torque transmitting mechanism 390, the position of the coupling pins 398, 400 within the transverse slots 406, 412 will complete an oscillation cycle.

In the torque transmitting mechanism 390, with respect to each other, the rotating shafts and the coupling each have a "yaw" degree-of-freedom (DOF) around the associated pin's longitudinal centerline and a "pitch" DOF around a line perpendicular to the pin's longitudinal centerline. The two "yaw" axes are parallel, and the "pitch" axes are constrained by engagement between the rotating shaft to each be one-half the total angle between the driving and driven shafts.

Figure 22A:
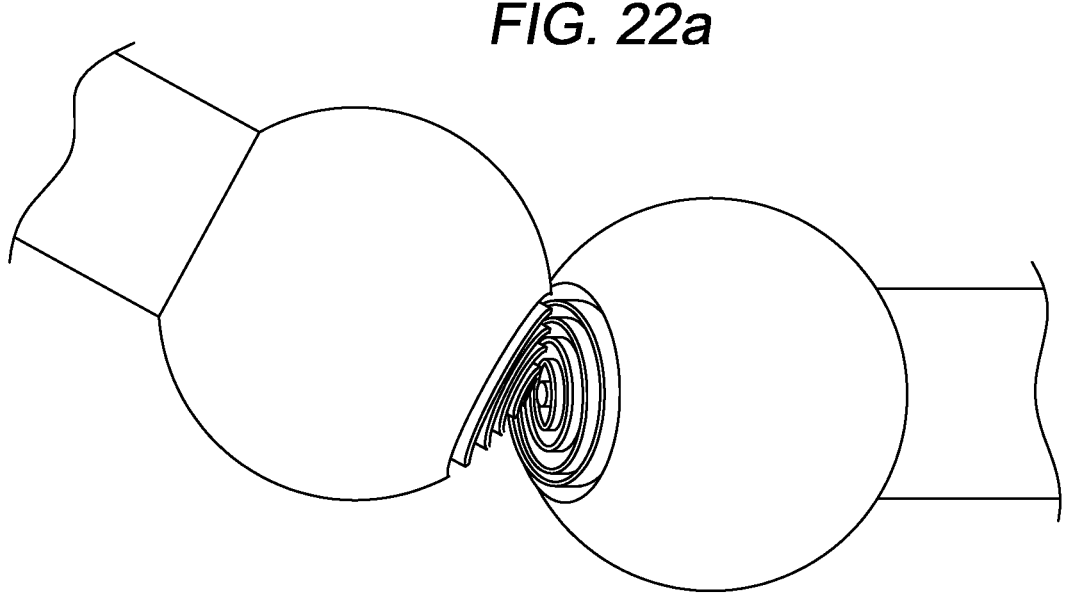
FIG. 22a is a perspective view of drive and driven shafts having multiple rows of spherical gear teeth configured to provide shaft angle constraint, in accordance with many embodiments.
Figure 22B:
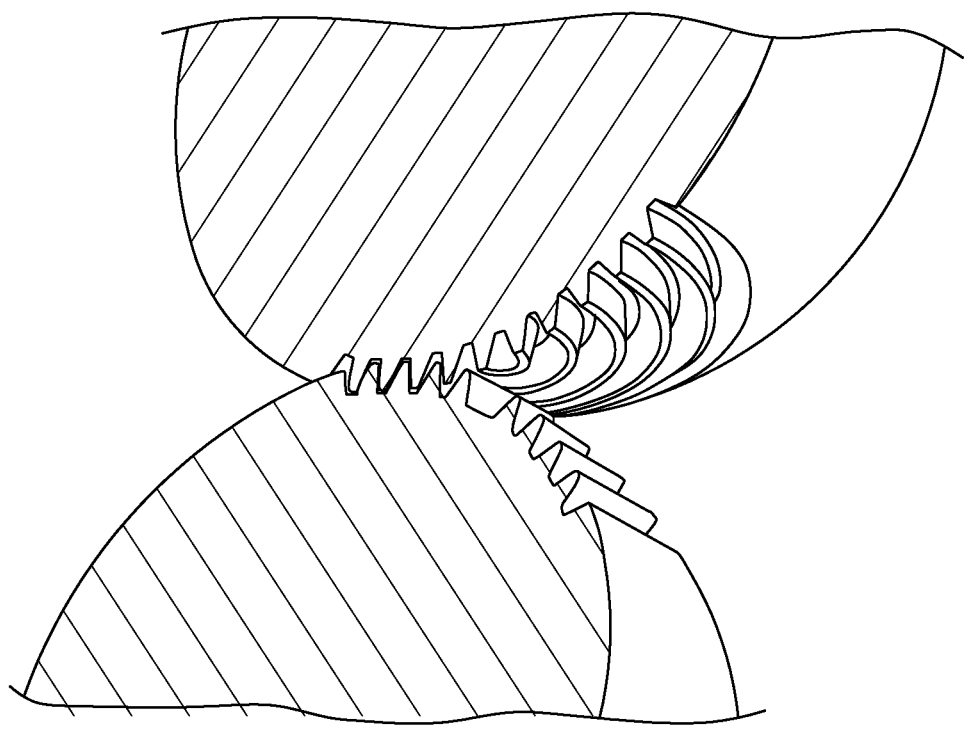
FIG. 22b is a cross-sectional/perspective view of the drive and driven shafts of FIG. 22a, illustrating gear teeth cross-sections and the spherical arrangement of the gear teeth.

Multiple rows of spherical gear teeth can be used to couple the drive and driven shafts so as to provide shaft angle constraint. For example, FIG. 22a illustrates multiple rows of interfacing spherical gear teeth. FIG. 22b illustrates the cross-sectional profile and spherical arrangement of the gear teeth of FIG. 22a.

Figure 23A:
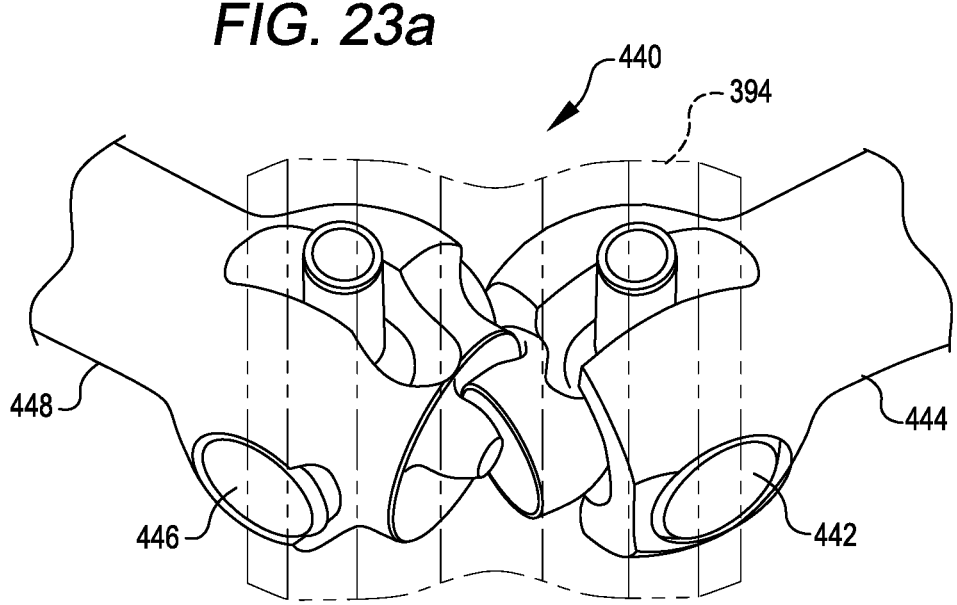
FIG. 23a is a side view of a mechanism for transmitting torque through an angle having a double cross pin design, in accordance with many embodiments.

FIG. 23a is a side view of a mechanism 440 for transmitting torque through an angle, in accordance with many embodiments. The torque transmitting mechanism 440 is similar to the mechanism 390 described above, but has a double cross pin configuration. For example, the mechanism 440 uses the same coupling member 394 and the same coupling pins 398, 400 as the mechanism 390, but incorporates a drive shaft cross pin 442 to couple a drive shaft 444 with the coupling pin 398, and a driven shaft cross pin 446 to couple a driven shaft 448 with the coupling pin 400. In FIG. 23a, a "see through" coupling member 394 is shown to better illustrate details of the double cross pin configuration.

Figure 23B:
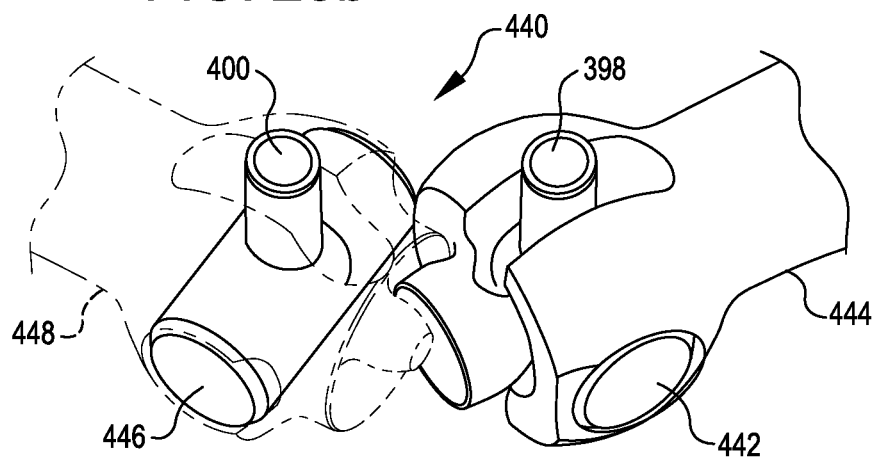
FIG. 23b is a side view of the mechanism of FIG. 23a without the coupling element.

FIG. 23b shows the mechanism 440 with the coupling member 394 removed and a "see through" driven shaft 448 to better illustrate the driven shaft cross pin 446. The driven shaft cross pin 446 is received within a bore of the driven shaft 448 and is rotatable within the driven shaft bore. The coupling pin 400 is received within a bore of the driven shaft cross pin 446. Relative rotation between the driven shaft 448 and the coupling member 394 about the centerline of the coupling pin 400 occurs via rotation of the coupling pin 400 relative to the coupling member 394 and/or rotation of the coupling pin 400 relative to the driven shaft cross pin 446. Similarly, the drive shaft cross pin 442 is received within a bore of the drive shaft 444 and it is rotatable within the drive shaft bore. The coupling pin 398 is received within a bore of the drive shaft cross pin 442. Relative rotation between the drive shaft 444 and the coupling member 394 about the centerline of the coupling pin 398 occurs via rotation of the coupling pin 398 relative to the coupling member 394 and/or rotation of the coupling pin 398 relative to the drive shaft cross pin 442.

Figure 23C:
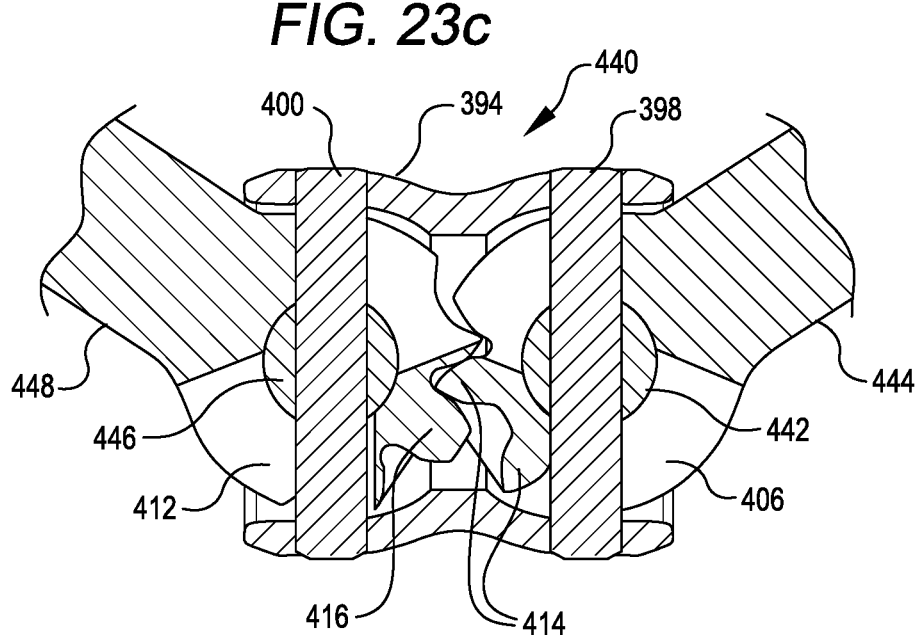
FIG. 23c is a cross-sectional view of the mechanism of FIGS. 23a and 23b.

FIG. 23c is a cross-sectional view of the mechanism 440 of FIGS. 23a and 23b taken through the centerlines of the coupling pins 398, 400. The drive shaft transverse slot 406 is configured to accommodate the coupling pin 398 throughout a range of angles between the drive shaft 444 and the coupling member 394 that occurs via rotation of the drive shaft 444 relative to the centerline of the drive shaft cross pin 442. Similarly, the driven shaft transverse slot 412 is configured to accommodate the coupling pin 400 throughout a range of angles between the driven shaft 448 and the coupling member 394 that occurs via rotation of the driven shaft 448 relative to the centerline of the driven shaft cross pin 446. As can be seen by comparing FIG. 23c to FIG. 19d, the double cross pin configuration of the mechanism 440 provides for reduced mechanism free-play along the drive and driven shafts as compared to the single cross pin configuration of the mechanism 390. Such reduced free-play may provide more consistent coupling between the drive shaft gear teeth 414 and the driven shaft gear teeth 416.

Figure 23D:
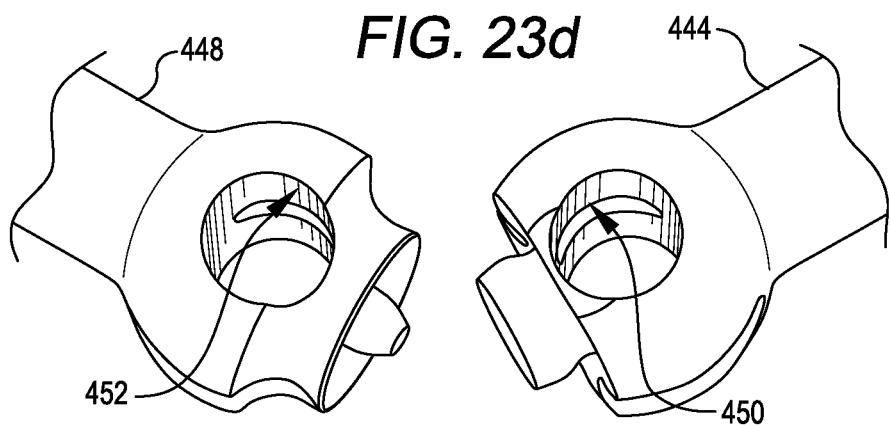
FIG. 23d is a perspective view of the drive and driven shafts of FIGS. 23a, 23b, and 23c, showing a cross pin receiving bore in each of the drive and driven shafts.
Figure 23E:
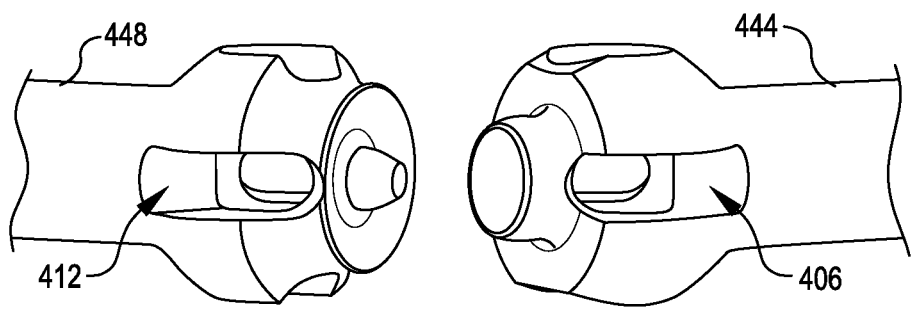
FIG. 23e is a perspective view of the drive and driven shafts of FIGS. 23a, 23b, 23c, and 23d, illustrating the configuration of pin receiving transverse slots in each of the drive and driven shafts.

FIG. 23d shows the cross pin receiving bore 450 of the drive shaft 444 and the similar cross pin receiving bore 452 of the driven shaft 448. FIG. 23e shows the drive shaft transverse slot 406 and the driven shaft transverse slot 412.

Figure 24A:
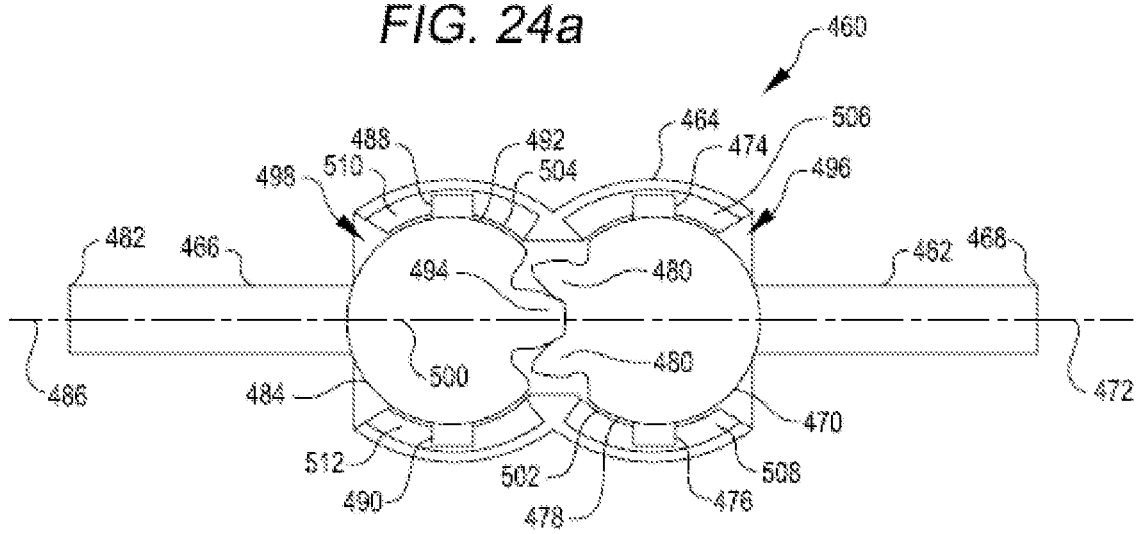
FIG. 24a is a simplified diagrammatic illustration of a mechanism for transmitting torque through an angle in which protrusions interacting with slots transfer rotational motion between a drive shaft and a coupling member and between the coupling member and a driven shaft, in accordance with many embodiments.

FIG. 24a is a simplified diagrammatic illustration of a mechanism 460 for transmitting torque through an angle in which shaft protrusions interact with coupling member slots to transfer rotational motion, in accordance with many embodiments. The torque transmitting mechanism 460 includes the drive shaft 462, a coupling member 464, and a driven shaft 466.

The drive shaft 462 is configured to axially and rotationally couple with the coupling member 464. The drive shaft 462 has a proximal end 468, a distal end 470, and a drive axis 472 defined there between. The drive shaft 462 includes a first cylindrical protrusion 474 protruding from the drive shaft distal end 470 and a second cylindrical protrusion 476 protruding from an opposing side of the drive shaft distal end 470. The drive shaft distal end 470 has a spherical surface 478 and spherical gear teeth 480.

Similarly, the driven shaft 466 is configured to axially and rotationally couple with the coupling member 464. The driven shaft 466 has a distal end 482, a proximal end 484, and a driven axis 486 defined there between. The driven shaft 466 includes a third cylindrical protrusion 488 protruding from the driven shaft proximal end 484 and a fourth cylindrical protrusion 490 protruding from an opposing side of the driven shaft proximal end 484. The driven shaft proximal end 484 has a spherical surface 492 and spherical gear teeth 494.

The coupling member 464 is configured to axially couple with both the drive shaft distal end 470 and the driven shaft proximal end 484. The coupling member 464 has a tubular structure defining a drive receptacle 496, a driven receptacle 498, and a coupling axis 500 defined there between. The drive receptacle 496 is shaped to interface with the drive shaft distal end 470 so as to create a ball joint constraint between the drive shaft distal end 470 and the drive receptacle 496. For example, the drive receptacle 496 can include one or more surfaces configured to interface with the drive shaft distal end spherical surface 478. In many embodiments, the drive receptacle 496 includes a spherical surface 502 configured to interface with the drive shaft distal end spherical surface 478. Similarly, the driven receptacle 498 is shaped to interface with the driven shaft proximal end 484 so as to create a ball joint constraint between the driven shaft proximal end 484 and the driven receptacle 498. For example, the driven receptacle 498 can include one or more surfaces configured to interface with the driven shaft proximal end spherical surface 492. In many embodiments, the driven receptacle 498 includes a spherical surface 504 configured to interface with the driven shaft proximal end spherical surface 492. As described in more detail below, the coupling member 464 can include one or more separate pieces, for example, two pieces.

The coupling member 464 is also configured to rotationally couple with both the drive shaft distal end 470 and the driven shaft proximal end 484. The coupling member first receptacle 496 includes a first slot 506 and a second slot 508. The first slot 506 and the second slot 508 are configured to receive the first protrusion 474 and the second protrusion 476, respectively, and accommodate the protrusions 474, 476 throughout a range of angles between the drive shaft 462 and the driven shaft 466 (as illustrated in FIG. 24d). Similarly, the coupling member second receptacle 498 includes a third slot 510 and a fourth slot 512. The third slot 510 and the fourth slot 512 are configured to receive the third protrusion 488 and the fourth protrusion 490, respectively, and accommodate the protrusions 488, 490 throughout a range of angles between the drive shaft 462 and the driven shaft 466. Interaction between the drive shaft protrusions 474, 476 and the first receptacle slots 506, 508 transfers rotational motion from the drive shaft 462 to the coupling member 464. Similarly, interaction between the second receptacle slots 510, 512 and the driven shaft protrusion 488, 490 transfers rotational motion from the coupling member 464 to the driven shaft 466.

The torque transmitting mechanism 460 uses engagement between the drive shaft distal end 470 and the driven shaft proximal end 484 to control the relative angular orientations of the drive shaft 462, the coupling member 464, and the driven shaft 466. Engagement features, for example, the spherical gear teeth 480, 494, can be used to control the relative orientations of the drive shaft 462, the coupling member 464, and the driven shaft 466. While the shaft angle constraint between the drive shaft 462 and the driven shaft 466 is provided by meshing spherical gear teeth 480, 494 in the torque transmitting mechanism 460, the use of spherical gear teeth is merely exemplary. Other suitable shaft angle constraints can also be used, for example, the shaft angle constraints for the torque transmitting mechanism 390 discussed above can also be used in the torque transmitting mechanism 460. Additionally, the gear tooth definitions applicable to the above discussed torque transmitting mechanism 390 are also applicable to the torque transmitting mechanism 460.

Figure 24B:
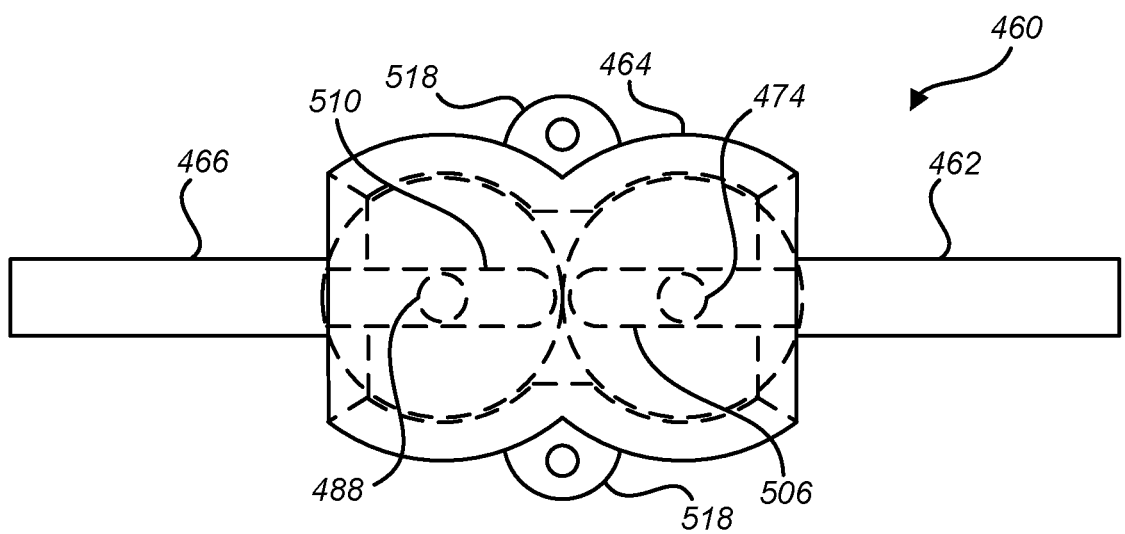
FIG. 24b is a view of the mechanism of FIG. 24a along a view direction parallel to the protrusions, in accordance with many embodiments.

FIG. 24b is a view of the torque transmitting mechanism 460 of FIG. 24a along a view direction parallel to the protrusions, in accordance with many embodiments. Hidden lines illustrate the first protrusion 474 within the first slot 506 and the third protrusion 488 within the third slot 510. The elongated shape of the slots enables the drive shaft 462 and the driven shaft 466 to pivot relative to the coupling member 464 while providing for the transfer of rotational motion between the drive shaft 462 and the coupling member 464, and between the coupling member 464 and the driven shaft 466.

Figure 24C:
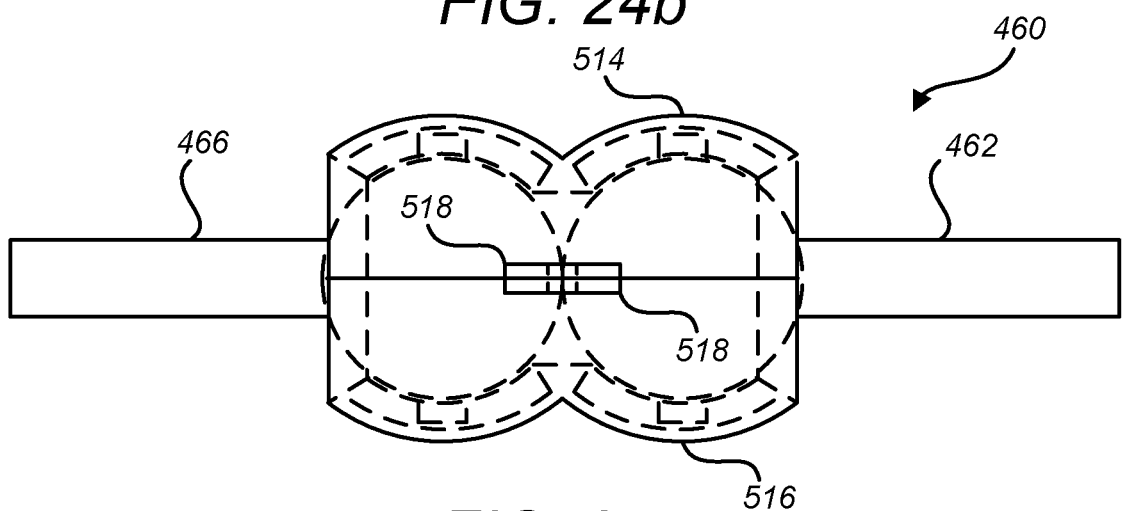
FIG. 24c is a view of the mechanism of FIGS. 24a and 24b along a view direction normal to the protrusions, illustrating details of a two piece coupling member, in accordance with many embodiments.
Figure 24D:
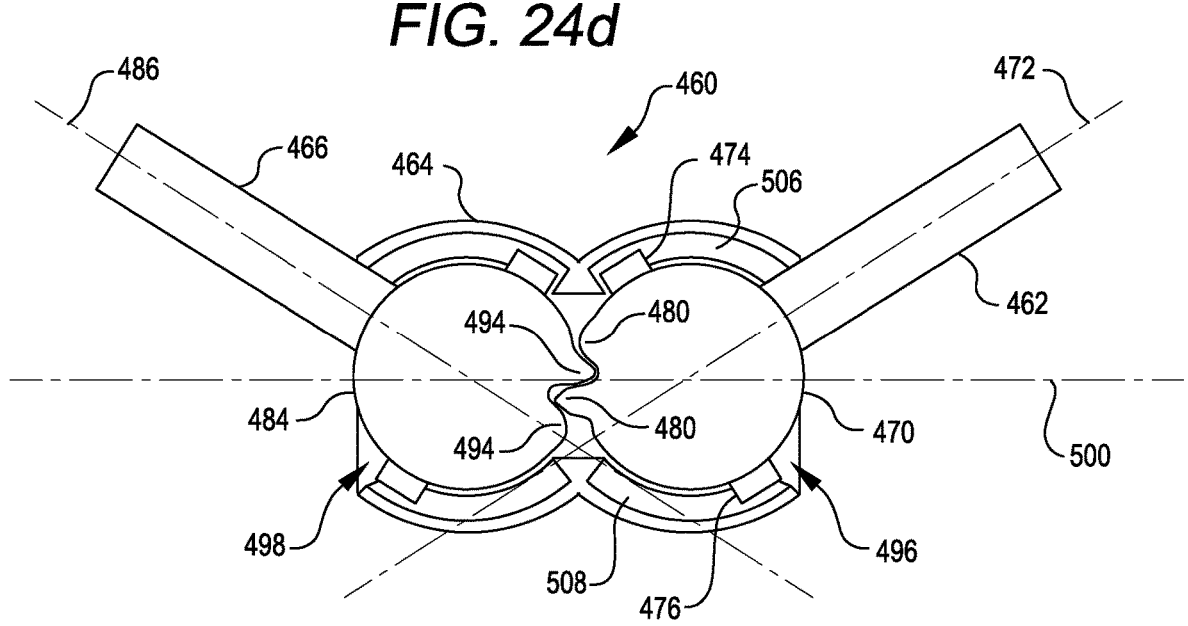
FIG. 24d illustrates the mechanism of FIGS. 24a, 24b, and 24c in an angled configuration, in accordance with many embodiments.

FIG. 24c is a view of the torque transmitting mechanism 460 of FIGS. 24a and 24b along a view direction normal to the protrusions, illustrating details of a two piece coupling member 464, in accordance with many embodiments. The coupling member 464 includes a first piece 514 and a second piece 516. The first piece 514 and the second piece 516 include attachment flanges 518 having fastener holes for attachment fasteners (not shown). Although the coupling member 464 is shown as including the first piece 514 and the second piece 516 that are shown as being joined via attachment flanges 518, this approach is merely exemplary and other suitable approaches can be used. For example, the coupling member 464 can be split into a central tubular piece and two adjoining end caps that can be assembled to the central tubular piece after the drive shaft 462 and the driven shaft 466 are positioned relative to the central tubular piece.

FIG. 24d illustrates the torque transmitting mechanism 460 of FIGS. 24a, 24b, and 24c in an angled configuration, in accordance with many embodiments. The spherical gear teeth 480, 494, in conjunction with the positional constraint provided by the interface between the drive shaft distal end 470 and the coupling member first receptacle 496, and the positional constraint provided by the interface between the driven shaft proximal end 484 and the coupling member second receptacle 498, constrain the torque transmitting mechanism 460 so that the angle between the drive axis 472 and the coupling axis 500 is substantially equivalent to the angle between the coupling axis 500 and the driven axis 486. In operation, rotation of the drive shaft 462 about the drive axis 472 produces rotation of the coupling member 464 about the coupling axis 500 via interaction between the first protrusion 474 and the first slot 506, and interaction between the second protrusion 476 and the second slot 508. In operation, the position of the protrusions 474, 476 within the slots 506, 508 oscillates in a manner similar to the oscillation of the coupling pins 398, 400 discussed above with reference to the torque transmitting mechanism 390 of FIG. 18 through FIG. 21b. Similarly, rotation of the coupling member 464 about the coupling axis 500 produces rotation of the driven shaft 466 about the driven axis 486.

Figure 25A:
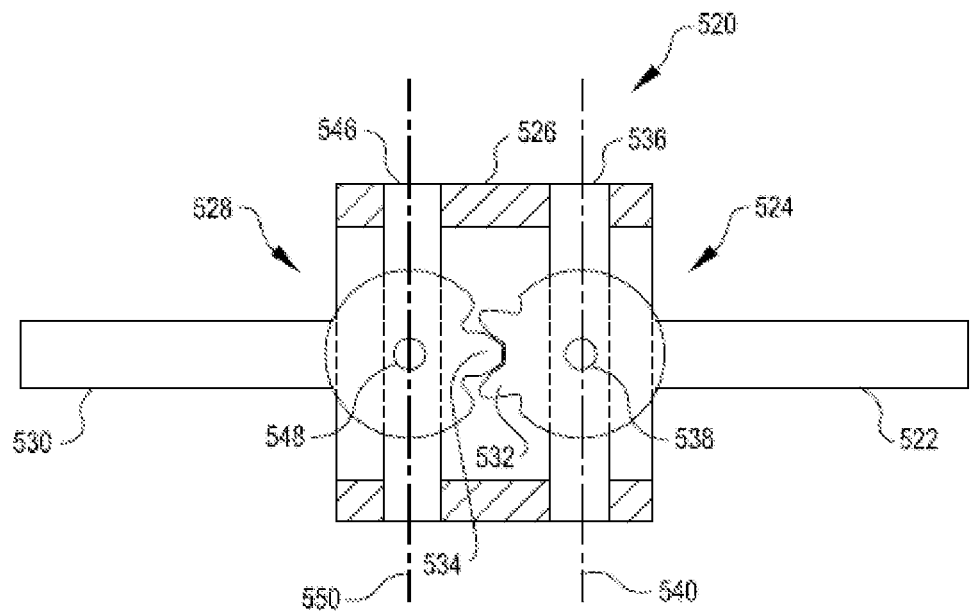
FIGS. 25a and 25b are simplified diagrammatic illustrations of a mechanism for transmitting torque through an angle in which modified U-joint coupling members transfer rotational motion between a drive shaft and a coupling member and between the coupling member and a driven shaft, in accordance with many embodiments.
Figure 25B:
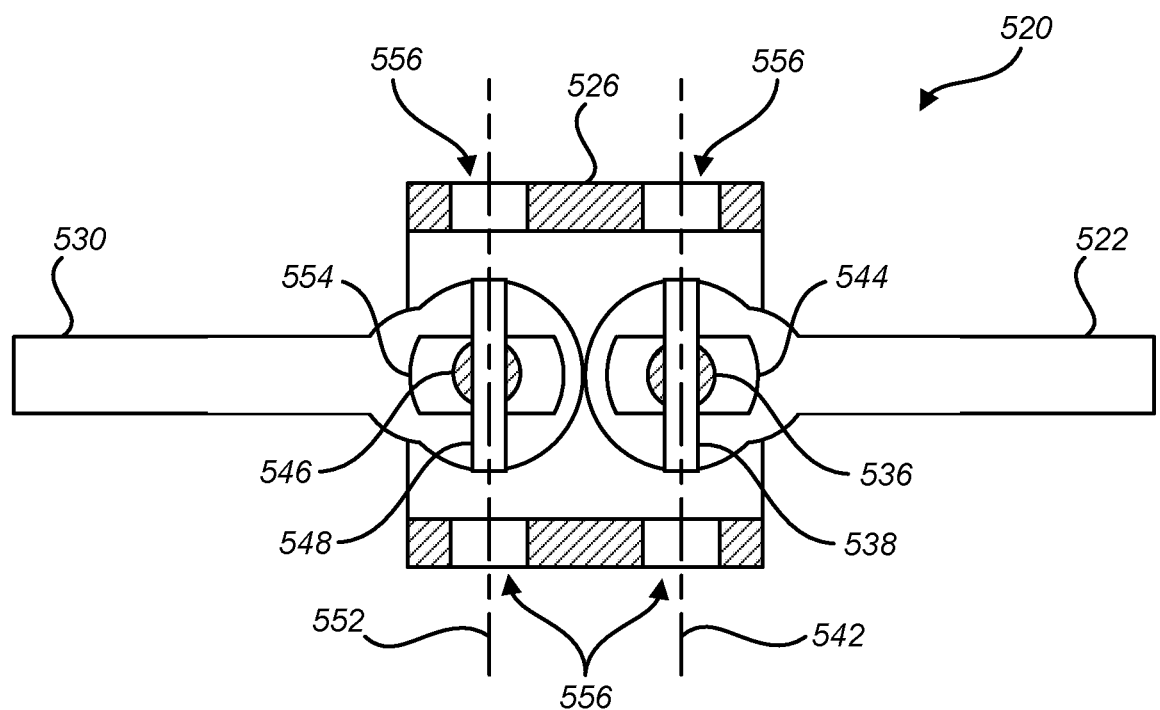

FIGS. 25a and 25b are simplified diagrammatic illustrations of a mechanism 520 for transmitting torque through an angle in which modified U-joint coupling members transfer rotational motion between a drive shaft and a coupling member and between the coupling member and a driven shaft, in accordance with many embodiments. The torque transmitting mechanism 520 includes a drive shaft 522, a first modified U-joint coupling 524, a coupling member 526, a second modified U-joint coupling 528, and a driven shaft 530. As with the above described embodiments, the torque transmitting mechanism 520 employs drive shaft and driven shaft engagement features (e.g., spherical gear teeth 532, 534) to constrain the relative orientations of the drive shaft 522, the coupling member 526, and the driven shaft 530.

The modified U-joint couplings 524, 528 axially and rotationally couple the drive shaft 522 to the coupling member 526, and the coupling member 526 to the driven shaft 530, respectively. The first modified U-joint coupling 524 includes a first pin 536 and a second pin 538. The first pin 536 is mounted for rotation relative to the coupling member 526 about a first pin axis 540. The second pin 538 is oriented transverse to the first pin 536 and is coupled with the first pin 536. The drive shaft 522 is coupled with the second pin 538 to rotate about a second pin axis 542. The second pin axis 542 itself rotates about the first pin axis 540. The drive shaft 522 includes an opening 544 configured to accommodate the first pin 536. Similarly, the second modified U-joint coupling 528 includes a third pin 546 and a fourth pin 548. The third pin 546 is mounted for rotation relative to the coupling member 526 about a third pin axis 550. The fourth pin 548 is oriented transverse to the third pin 546 and is coupled with the third pin 546. The driven shaft 530 is coupled with the fourth pin 548 to rotate about a fourth pin axis 552. The fourth pin axis 552 itself rotates about the third pin axis 550. The driven shaft 530 includes an opening 554 configured to accommodate the third pin 546. The coupling member 526 can include openings 556 that provide for installation of the second pin 538 and the fourth pin 548.

In operation, the torque transmitting mechanism 520 functions similarly to the torque transmitting mechanisms 390, 460 set forth above. The drive shaft and driven shaft engagement features (e.g., spherical gear teeth 532, 534) constrain the relative orientations of the drive shaft 522, the coupling member 526, and the driven shaft 530 so that relative angles between the drive shaft 522 and the coupling member 526, and between the coupling member 526 and the driven shaft 530 are substantially equal. In operation, rotation of the drive shaft 522 produces rotation of the coupling member 526 via the first modified U-joint coupling 524. Similarly, rotation of the coupling member 526 produces rotation of the driven shaft 530 via the second modified U-joint coupling 528.

Combined Features

FIG. 26 illustrates a compact wrist 600 having a two degree-of-freedom wrist that is articulated by linked tension members as disclosed herein, as well as the use of double universal joints as disclosed herein to transmit torque through an angle across the two degree-of-freedom wrist. The compact wrist 600 integrates a two degree-of-freedom wrist, wrist articulation by linked tension members, and torque transmission through an angle by double universal joints. While all three of these aspects are included in the compact wrist 600, a wrist can utilize any of the aspects disclosed herein individually or in any suitable combination. A benefit of these three combined aspects is an ability to transmit off-centerline torque through a two degree-of-freedom wrist mechanism with a large angular displacement capability (e.g., up to about 60 degrees in any direction) and relatively short length. In a minimally invasive surgical environment (e.g., during bowel surgery), such a short length wrist mechanism allows a surgical end effector that requires the transmitted torques for operation to be maneuvered (pitched, yawed, rolled) in tight spaces, so that the lateral distance between the articulated end effector and the distal end of the supporting shaft is minimized. The descriptions above have concentrated on describing particular aspects and features. It should be understood, however, that various aspects and features may be combined whenever practical. That is, particular aspects and features described above with reference to one embodiment may be incorporated into one or more other embodiments, even though such alternate embodiments are not specifically shown.

It is understood that the examples and embodiments described herein are for illustrative purposes and that various modifications or changes in light thereof will be suggested to persons skilled in the art and are to be included within the spirit and purview of this application and the scope of the appended claims. Numerous different combinations are possible, and such combinations are considered to be part of the present invention.

What is claimed is:

1. A method of articulating and actuating an end effector of a surgical tool, the method comprising:
    supporting an end effector base of the end effector by an elongate shaft of the surgical tool via a wrist assembly of the surgical tool, wherein the end effector base is pivotally coupled with the elongate shaft via the wrist assembly, and wherein the wrist assembly is configured to accommodate rotation of the end effector base relative to the elongate shaft about a first axis and a second axis perpendicular to the first axis;
    controlling orientation of the end effector base relative to the elongate shaft via four elongated tension members, wherein each of the four elongated tension members interfaces with the end effector base, and wherein the four elongated tension members extend distally within the elongate shaft and are arranged in a first diagonally opposed pair and a second diagonally opposed pair; and
    rotating an input shaft of the end effector around an input shaft axis by rotating a drive shaft of the surgical tool around a drive shaft axis, wherein the drive shaft extends distally within the elongate shaft and is coupled with the input shaft by a constant speed coupling assembly configured so that a rate of rotation of the drive shaft and a rate of rotation of the input shaft are equal when the end effector base is pivoted relative to the elongate shaft.

2. The method of claim 1, wherein controlling orientation of the end effector base relative to the elongate shaft via four elongated tension members comprises controlling articulation of the four elongated tension members to selectively orient the end effector base relative to the elongate shaft about each of the first axis and the second axis.

3. The method of claim 2, wherein controlling articulation of the four elongated tension members comprises:
    controlling articulation of a first capstan, wherein the first diagonally opposed pair is drivingly coupled with the first capstan; and
    controlling articulation of a second capstan, wherein the second diagonally opposed pair is drivingly coupled with the second capstan.

4. The method of claim 2, wherein the first capstan and the second capstan are actuated by a surgical robot.

5. The method of claim 1, wherein each of the four elongated tension members is under tension for all orientations of the end effector base relative to the elongate shaft.

6. The method of claim 1, wherein the first axis and the second axis are non-intersecting.

7. The method of claim 1, wherein the second axis is perpendicular to the first axis.

8. The method of claim 1, wherein:
    the constant speed coupling assembly comprises a coupling member and a first coupling pin;
    the coupling member comprises a coupling member first end receptacle;
    the first coupling pin crosses the coupling member first end receptacle;
    the drive shaft comprises a drive shaft distal end outer surface that interfaces with the coupling member first end receptacle; and
    the drive shaft comprises a drive shaft distal end slot that receives the first coupling pin throughout a range of angles between the input shaft axis and the drive shaft axis.

9. The method of claim 8, wherein:
    the constant speed coupling assembly comprises a first cross pin that couples the drive shaft with the first coupling pin; and
    the first cross pin is oriented transverse to the first coupling pin and mounted for rotation relative to the drive shaft.

10. The method of claim 9, wherein:
    the coupling member comprises a coupling member second end receptacle; and
    the constant speed coupling assembly comprises a second coupling pin that crosses the coupling member second end receptacle.

11. The method of claim 1, wherein the end effector comprises a surgical stapler that is actuated via rotating the input shaft.

* * * * *